US008609698B2

(12) United States Patent
Thede et al.

(10) Patent No.: US 8,609,698 B2
(45) Date of Patent: *Dec. 17, 2013

(54) SUBSTITUTED DIPYRIDYL-DIHYDROPYRAZOLONES AND USE THEREOF

(75) Inventors: Kai Thede, Berlin (DE); Ingo Flamme, Reichshof (DE); Felix Oehme, Wuppertal (DE); Jens-Kerim Ergüden, Wülfrath (DE); Friederike Stoll, Düsseldorf (DE); Hanno Wild, Wuppertal (DE); Peter Kolkhof, Wuppertal (DE); Hartmut Beck, Köln (DE); Mario Jeske, Solingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 566 days.

This patent is subject to a terminal disclaimer.

(21) Appl. No.: 12/447,207

(22) PCT Filed: Oct. 16, 2007

(86) PCT No.: PCT/EP2007/008951
§ 371 (c)(1),
(2), (4) Date: Dec. 21, 2009

(87) PCT Pub. No.: WO2008/067874
PCT Pub. Date: Jun. 12, 2008

(65) Prior Publication Data
US 2010/0093803 A1    Apr. 15, 2010

(30) Foreign Application Priority Data

Oct. 26, 2006    (DE) .......................... 10 2006 050 515

(51) Int. Cl.
*A61K 31/4439*    (2006.01)
*C07D 401/14*    (2006.01)

(52) U.S. Cl.
USPC .......................................... 514/333; 546/256

(58) Field of Classification Search
USPC .......................................... 546/256; 514/333
See application file for complete search history.

(56) References Cited

U.S. PATENT DOCUMENTS

| 4,075,003 | A | 2/1978 | Beck et al. |
| 4,118,574 | A | 10/1978 | Beck et al. |
| 4,663,327 | A | 5/1987 | Sasse et al. |
| 4,698,344 | A | 10/1987 | Sasse et al. |
| 4,806,540 | A | 2/1989 | Sasse et al. |
| 2003/0083351 | A1 | 5/2003 | Almstead et al. |
| 2006/0067927 | A1 | 3/2006 | Chandrasekaran et al. |
| 2006/0160826 | A1 | 7/2006 | Ghanbari et al. |
| 2010/0093803 | A1 | 4/2010 | Thede et al. |
| 2010/0305085 | A1 | 12/2010 | Thede et al. |

FOREIGN PATENT DOCUMENTS

| CA | 1067907 A1 | 12/1979 |
| CA | 2364908 A1 | 9/2000 |
| CA | 2608099 A1 | 11/2006 |
| CA | 2667392 | 2/2008 |
| DE | 2651008 A1 | 6/1977 |
| EP | 165448 A2 | 12/1985 |
| EP | 183159 A2 | 6/1986 |
| EP | 212281 A1 | 3/1987 |
| WO | WO-96/12706 A1 | 5/1996 |
| WO | WO-00/51989 A1 | 9/2000 |
| WO | WO-02/092573 A2 | 11/2002 |
| WO | 03/051833 A2 | 6/2003 |
| WO | WO-03/074550 A2 | 9/2003 |
| WO | 2004052284 | 6/2004 |
| WO | 2004/089303 A2 | 10/2004 |
| WO | 2004087066 | 10/2004 |
| WO | 2005030121 | 4/2005 |
| WO | 2006/101903 | 9/2006 |
| WO | WO 2006/114213 | 11/2006 |
| WO | 2007/008541 A2 | 1/2007 |

OTHER PUBLICATIONS

Guillory (in Brittain ed.), "Polymorphism, etc.," NY: Marcel Dekker, Inc., 1999, 1-2, 125-181, 183-226.*
Yu et al., "Physical characterization of, etc.," PSTT, vl. 1(3), 118-127 (1998).*
S.P. Singh et al.: "Reaction of 1-[5-Hydroxy-3-Methyl-1-(2-Thiazolyl)-4-Pyrazolyl]-1,3-Butanediones with Phenyl and Heterocyclic Hydrazines: a Convienient Syntheses of 4,5-Bipyrazoles," Indian Journal of Heterocyclic Chemistry, Jul.-Sep. 1993, 3: 5-8.
J. Elguero et al.: "A 1H and 13C NMR Study of the Structure and Tautomerism of 4-Pyrazolylprazolinones," J. Heterocyclic Chem., May-Jun. 1990, 27: 865-870.
H. Barth er al.: "Konstitution und Synthese des Muscafavins," Liebigs Ann. Chem., 1981, pp. 2164-2179.
R.A. Evans er al.—Trifluromethyl-substituted Dehydrodizepines and Cyanopyrroles form Azido-/Tetrazolo-pyridines, J. Chem. Commun., 1992, 15: 1062-1064.
F. Oehme et al.: "A Nonradioactive 96-well Plate Assay for the Detection of Hypozia-Inducible Factor Prolyl Hydroxylase Activity," Analytical Biochemistry, 2004, 330: 74-80.
F. Oehme et al.: "Overexpression of PH-4, a Novel Putative Proline 4-Hydroxylase, Modulates Activity of Hypoxia-Inducible Transcription Factors," Biochemical and Biophysical Research Communications, 2002, 296: 343-349.
C.A. Heid et al.: "Real Time Quantative PCR," Genome Research, 1996, 6(10): 986-994.
N. Yokoyama et al.: Synthesis and Structure-Activity Relationships of Oxamic Acid and Acetic Acid Derivatives Released to L-Thyronine,: J. Med. Chem., 1995, 38:695-707.
N. Sperber er al.: "Parasympathetic Blocking Agernt, III. N-Alkylpiperidinecarboxylic Esters," J. Am. Chem. Soc, 1959, 81: 704-709.
M.A. Meziane et al.: "A New Route to 1-Oxo-1,2-Dihydropyrimido[1,6-a]Benzimidazole-4-Carboxylates from Ethyl 2-(Benzimidazol-2-yl)-3-(Dimethylamino)Acrylate Using Solvent-Free Conditions," Synthesis, Jul. 1996, pp. 967-969.

(Continued)

*Primary Examiner* — Patricia L Morris
(74) *Attorney, Agent, or Firm* — Karen B. King

(57) ABSTRACT

The present application relates to novel substituted dipyridyldihydropyrazolone derivatives, processes for their preparation, their use for treatment and/or prophylaxis of diseases and their use for the preparation of medicaments for treatment and/or prophylaxis of diseases, in particular cardiovascular and hematological diseases and kidney diseases, and for promoting wound healing.

14 Claims, No Drawings

(56) References Cited

OTHER PUBLICATIONS

Vippagunta et al., "Crystalline Solids," Advanced Drug Delivery Reviews, 2001, 48: 3-26.
West, "Solid Solutions," 1988, Chapter 10, pp. 358 and 365.
Ulrich, "Crystallization: 4. Crystal Characteristics," Kirk-Othmer Encyclopedia of Chemical Technology, Aug. 2002.
B. Djerrari et al.: "3-Methyl-1-(Pyridin-2-yl)-4-(1-Pyridin-2-yl-3-Methyl-1H-Pyrazol-5-yl)-2H-3-Pyrazolin-5(1HI)-one," Acta Crystallographica Section E, Structure Reports Online, 2001, E57, No. 11, pp. o1126-o1127.
Hill et al. "Inhibition of TRPM2 channels by the antifungal agents clotrimazole and econazole," Naunyn Schmiedebergs Arch. Pharmacol, 2004, 370: 277-238, abstract only.
U.S. Appl. No. 11/919,478, filed Oct. 30, 2009.
U.S. Appl. No. 12/447,192, filed Oct. 12, 2007.
U.S. Appl. No. 12/447,201, filed Oct. 26, 2007.
U.S. Appl. No. 12/427,749, filed Apr. 22, 2009, now US Patent No. 8,067,407.
M. Eder et al (eds.).: "Allgemeine Pathologie und Pathologische Anatomie," Aufl., 33, Springer Verlag, Berlin, 1990.
R. F. Schmidt et al. (eds.): "Physiologie des Menschen," 27, Aufl., Springer Verlag, Berlin, 1997.
G. Löeffler et al, (eds.): "Biochemie und Pathobiochemie," 7, Aufl, Springer Verlag, Berlin, 2003.
M. Simons et al.: "Therapeutic Angiogenesis in Cardiovascular Disease," Nature Reviews Drug Discovery, vol. 2, Nov. 2003, pp. 1-9.
K-U Eckardt: "The Potential of Erythropoietin and Related Strategies to Stimulate Erythropoiesis," Current Opinion in Investigational Drugs, vol. 8, No. 2, 2001, pp. 1081-1085.
J. S. Berns: "Should the Target Hemoglobin for Patients with Chronic Kidney Disease Treated with Erythropoietic Replacement Therapy be Changed?," Seminars in Dialysis, vol. 18, No. 1 Jan.-Feb. 2005, pp. 22-29.
K. Caiola et al.: "Use of Erythropoietin in Heart Failure Management," The Annals of Pharmacotherapy, vol. 38, Dec. 2004, pp. 2145-2149.
S. D. Katz: "Mechanisms and Treatment of Anemia in Chronic Heart Failure," Congestive Heart Failure, vol. 10, 2004, pp. 243-247.
G. L. Semenza: "Hypoxia-Inducible Factor 1: Oxygen Homeostasis and Disease Pathophysiology," Trends in Molecular Medicine, vol. 7, No. 8, Aug. 2001, pp. 345-350.
R. H. Wenger et al.: "Oxygen(es) and the Hypoxia-Inducible Factor-1," Biol. Chem., vol. 378, Jul. 1987, pp. 609-616.
A.C.R. Epstein et al.: "Elegans EGL-9 and Mammalian Homologs Define a Family of Dioxygenases that Regulate HIF by Prolyl Hydroxylation," Cell, vol. 107, Oct. 5, 2001, pp. 43-54.
R.K. Bruick et al.: "A Conserved Family of Prolyl-4-Hydroxylases that Modify HIF," Science, vol. 294, Nov. 9, 2001, pp. 1337-1340.
M. Ivan et al.: "Biochemical purification and Pharmacological Inhibition of a Mammalian Prolyl Hydroxylase Acting on Hypoxia-Inducible Factor," Proc. Natl. Acad. Sci, U.S.A., vol. 99, No. 21, Oct. 15, 2002, pp. 13459-13464.
L. Aravind et al.: "The DNA-Repair Protein AlkB, EGL-9, and Leprecan Define New Families of 2-Oxoglutarate- and iron-dependent Dioxygenases," Genome Biology, vol. 2, No. 3, Feb. 19, 2001, pp. 1-8.
C.J. Schofield et al.: "Oxygen Sensing by HIF Hydroxylases," Nature Reviews Molecular Cell Biology, vol. 5, May 2004, pp. 343-354.
J. Büchi et al.: "Synthese und Pharmakologische Eigenschaften Einiger Pyridyl-Pyrazol-5-One," Helvetica Chemie Acta, vol. 49, 1966, pp. 272-280.

\* cited by examiner

SUBSTITUTED DIPYRIDYL-DIHYDROPYRAZOLONES AND USE THEREOF

The present application relates to novel substituted dipyridyldihydropyrazolone derivatives, processes for their preparation, their use for treatment and/or prophylaxis of diseases and their use for the preparation of medicaments for treatment and/or prophylaxis of diseases, in particular cardiovascular and hematological diseases and kidney diseases, and for promoting wound healing.

A deficient supply of oxygen to the human organism or its components which either impairs regular functioning of the organism or its components due to its duration and/or its extent or causes its functioning to break down completely is called hypoxia. Hypoxia can be caused by a reduction in the available oxygen in the air breathed in (for example during periods at a high altitude), by disorders in external respiration (for example as a result of disturbed functioning of the lungs or obstruction of the respiratory tract), by a reduction in the cardiac output (for example in the event of cardiac insufficiency, acute right ventricular overloading with pulmonary embolism), by too low an oxygen transport capacity of the blood (for example as a result of an anemia or intoxication, for example with carbon monoxide), locally demarcated by a reduced blood flow as a result of vascular occlusions (ischemia states typically for example of the heart, the lower extremities or the brain, diabetic macro- and microangiopathy) or also by an increased oxygen requirement of the tissue (for example as a result of increased muscular activity or local inflammations) [Eder, Gedigk (ed.), *Allgemeine Pathologie and pathologische Anatomie*, 33rd ed., Springer Verlag, Berlin, 1990]

The human organism is capable to a limited extent of adapting acutely and chronically to situations of reduced oxygen supply. In addition to an immediate response, which includes inter alia an increase in the cardiac output and respiratory output and a local dilation of blood vessels by vegetative-nervous control mechanisms, hypoxia brings about a change in the transcription of numerous genes. The function of the gene products here serves to compensate the oxygen deficiency. Thus, expression of several enzymes of glycolysis and glucose transporter 1 is enhanced, as a result of which anaerobic ATP production increases and survival of the oxygen deficiency is rendered possible [Schmidt, Thews (ed.), *Physiologie des Menschen*, 27th ed., Springer Verlag, Berlin, 1997; Löffler, Petrides (ed.), *Biochemie and Pathobiochemie*, 7th ed., Springer Verlag, Berlin, 2003].

Hypoxia furthermore leads to enhanced expression of vascular endothelial cell growth factor, VEGF, as a result of which regeneration of blood vessels (angiogenesis) is stimulated in hypoxic tissues. The blood flow through ischemic tissue is thereby improved in the long term. This counter-regulation is evidently only very inadequate in the case of various cardiovascular diseases and vascular occlusion diseases [overview in: Simons and Ware, *Therapeutic angiogenesis in cardiovascular disease*, Nat. Rev. Drug. Discov. 2 (11), 863-71 (2003)].

Furthermore, in cases of systemic hypoxia expression of the peptide hormone erythropoietin formed predominantly in the interstitial fibroblasts of the kidneys is enhanced. The formation of red blood cells in the bone marrow is thereby stimulated, and the oxygen transport capacity of the blood is therefore increased. This effect has been and is used by high-performance athletes in so-called high altitude training. A decrease in the oxygen transport capacity of the blood for example as a result of anemia after hemorrhaging usually causes an increase in erythropoietin production in the kidney. With certain forms of anemia, this regulatory mechanism may be disturbed or its normal value may be set lower. Thus for example in patients suffering from renal insufficiency, erythropoietin is indeed produced in the kidney parenchyma, but in significantly reduced amounts with respect to the oxygen transport capacity of the blood, which results in so-called renal anemia. Renal anemia in particular, but also anemias caused by tumors and HIV infection are conventionally treated by parenteral administration of recombinant human erythropoietin (rhEPO). No alternative therapy with an orally available medicament currently exists for this expensive therapy [overview in: Eckardt, *The potential of erythropoietin and related strategies to stimulate erythropoiesis*, Curr. Opin. Investig. Drugs 2(8), 1081-5 (2001); Berns, *Should the target hemoglobin for patients with chronic kidney disease treated with erythropoietic replacement therapy be changed?*, Semin Dial. 18 (1), 22-9 (2005)]. Recent studies demonstrate that, in addition to its erythropoiesis-increasing action, erythropoietin also has a protective (anti-apoptotic) action, which is independent thereof, on hypoxic tissue, in particular the heart and the brain. Furthermore, according to recent studies therapy with erythropoietin reduces the average severity of morbidity in patients with cardiac insufficiency [overviews in: Caiola and Cheng, *Use of erythropoietin in heart failure management*, Ann. Pharmacother. 38 (12), 2145-9 (2004); Katz, *Mechanisms and treatment of anemia in chronic heart failure*, Congest. Heart. Fail. 10 (5), 243-7 (2004)].

The genes described above which are induced by hypoxia have the common feature that the increase in their expression under hypoxia is caused by the so-called hypoxia-inducible transcription factor (HIF). HIF is a heterodimeric transcription factor which comprises an alpha and a beta subunit. Three HIF alpha isoforms are described, of which HIF-1 alpha and HIF-2 alpha are highly homologous and are of importance for hypoxia-induced gene expression. While the beta subunit (of which 2 isoforms have been described), which is also called ARNT (aryl hydrocarbon receptor nuclear translocator), is expressed constitutively, expression of the alpha subunit depends on the oxygen content in the cell. Under normoxia, the HIF alpha protein is poly-ubiquitinized and then degraded proteasomally. Under hypoxia this degradation is inhibited, so that HIF alpha dimerizes with ARNT and can activate its target genes. The HIF dimer bonds here to so-called hypoxia-responsible elements (HRE) in the regulatory sequences of its target genes. The HRE are defined by a consensus sequence. Functional HRE have been detected in the regulatory elements of numerous hypoxia-induced genes [overviews in: Semenza, *Hypoxia-inducible factor 1: oxygen homeostasis and disease pathophysiology*, Trends Mol. Med. 7 (8), 345-50 (2001); Wenger and Gassmann, *Oxygen(es) and the hypoxia-inducible factor-1*, Biol. Chem. 378 (7), 609-16 (1997)].

The molecular mechanism on which this regulation of HIF alpha is based has been clarified by the works of several independent groups of researchers. The mechanism is conserved from species to species: HIF alpha is hydroxylated by a subclass of oxygen-dependent prolyl 4-hydroxylases, called PHD or EGLN, on two specific prolyl radicals (P402 and P564 of the human HIF-1 alpha subunit). The HIF prolyl 4-hydroxylases are iron-dependent, 2-oxoglutarate-converting dioxygenases [Epstein et al., *C. elegans EGL-9 and mammalian homologs define a family of dioxygenases that regulate HIF by prolyl hydroxylation*, Cell 107 (1), 43-54 (2001); Bruick and McKnight, *A conserved family of prolyl-4-hydroxylases that modify HIF*, Science 294 (5545), 1337-40 (2001); Ivan et al., *Biochemical purification and pharmaco-* logical inhibition of a mammalian prolyl hydroxylase acting on hypoxia-inducible factor, Proc. Natl. Acad. Sci. U.S.A. 99 (21), 13459-64 (2002)]. The enzymes were annotated as prolyl hydroxylases for the first time in 2001[Aravind and Koonin, *The DNA-repair protein AlkB, EGL-9, and leprecan define new families of 2-oxoglutarate-and iron-dependent dioxygenases*, Genome Biol. 2 (3), research0007.1-0007.8, Epub 2001 Feb. 19].

The pVHL tumor suppressor protein, which together with elongin B and C forms the so-called VBC complex, which adapts the HIF alpha subunit to an E3 ubiquitin ligase, bonds to the prolyl-hydroxylated HIF alpha subunit. Since the prolyl 4-hydroxylation of the HIF alpha subunit and its subsequent degradation takes place as a function of the intracellular concentration of oxygen, HIF prolyl 4-hydroxylases have also been called a cellular oxygen sensor. Three isoforms of these enzymes have been identified: EGLN1/PHD2, EGLN2/PHD1 and EGLN3/PHD3. Two of these enzymes (EGLN2/PHD1 and EGLN3/PHD3) are induced transcriptionally even under hypoxia and are possibly responsible for the lowering of the HIF alpha levels to be observed under chronic hypoxia [overview in: Schofield and Ratcliffe, *Oxygen sensing by HIF hydroxylases*, Nat. Rev. Mol. Cell. Biol. 5 (5), 343-54 (2004)].

Selective pharmacological inhibition of HIF prolyl 4-hydroxylases brings about the increase in the gene expression of HIF-dependent target genes and is therefore beneficial for the therapy of numerous disease syndromes. In the case of diseases of the cardiovascular system in particular, an improvement in the course of the diseases is to be expected from induction of new blood vessels and the change in the metabolic situation of ischemic organs from aerobic to anaerobic ATP production. An improvement in the vascularization of chronic wounds promotes the healing process, especially in the case of poorly healing ulcera cruris and other chronic skin wounds. The induction of endogenous erythropoietin in certain disease forms, in particular in patients with renal anemia, is likewise a therapeutic goal to be aimed for.

The HIF prolyl 4-hydroxylase inhibitors described hitherto in the scientific literature do not meet the requirements to be imposed on a medicament. These are either competitive oxoglutarate analogs (such as for example N-oxalylglycine), which are characterized by their very low action potency, and therefore in in vivo models have as yet shown no action in the sense of an induction of HIF target genes. Or they are iron-complexing agents (chelators), such as desferroxamine, which act as non-specific inhibitors of iron-containing dioxygenases and, although they bring about an induction of the target genes, such as for example erythropoietin, in vivo, evidently counteract erythropoiesis by complexing of the available iron.

The object of the present invention is to provide novel compounds which can be employed for treatment of diseases, in particular cardiovascular and hematological diseases.

In the context of the present invention, compounds are now described which act as specific inhibitors of HIF prolyl 4-hydroxylases and on the basis of this specific action mechanism bring about in vivo, after parenteral or oral administration, the induction of HIF target genes, such as for example erythropoietin, and the biological processes thereby caused, such as for example erythropoiesis.

2-Heteroaryl-4-aryl-1,2-dihydropyrazolones having a bactericidal and/or fungicidal action are disclosed in EP 165 448 and EP 212 281. The use of 2-heteroaryl-4-aryl-1,2-dihydropyrazolones as lipoxygenase inhibitors for treatment of respiratory tract, cardiovascular and inflammatory diseases is claimed in EP 183 159. 2,4-Diphenyl-1,2-dihydropyrazolones having a herbicidal activity are described in DE 2 651 008. The preparation and pharmacological properties of certain 2-pyridyl-1,2-dihydropyrazolones are reported in *Helv. Chim. Acta* 49 (1), 272-280 (1966). WO 96/12706, WO 00/51989 and WO 03/074550 claim further compounds having a dihydropyrazolone partial structure and their use for treatment of diseases, and WO 02/092573 describes pyrazol-4-ylpyridine and pyrazol-4-ylpyrimidine derivatives as kinase inhibitors. Heteroaryl-substituted pyrazole derivatives for treatment of pain and various CNS diseases are furthermore described in WO 03/051833 and WO 2004/089303. WO 2006/114213 has meanwhile disclosed 2,4-dipyridyl-1,2-dihydropyrazolones as inhibitors of HIF prolyl 4-hydroxylases.

The present invention provides compounds of the general formula (I)

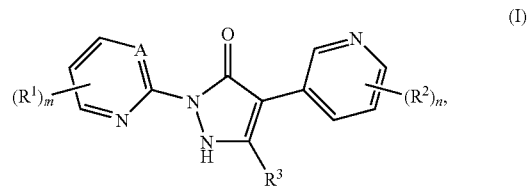

in which
A represents CH or N,
$R^1$ and $R^2$ are identical or different and for each individual occurrence represent a substituent independently of one another selected from the group consisting of halogen, cyano, nitro, hydroxyl, amino, hydroxycarbonyl, aminocarbonyl, $(C_1\text{-}C_6)$-alkyl, $(C_1\text{-}C_6)$-alkoxy, $(C_3\text{-}C_7)$-cycloalkyl, 4- to 7-membered heterocycloalkyl, phenyl, 5- or 6-membered heteroaryl, —C(=O)—$R^4$, —C(=O)—$OR^5$, —C(=O)—$NR^6R^7$, —O—C(=O)—$R^8$, —O—C(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2R^{19}$, —$SO_2$—$R^{20}$, —$SO_2$—$NR^{21}R^{22}$, —$OR^{23}$, —$SR^{24}$ and —$NR^{25}R^{26}$ in which (i) $(C_1\text{-}C_6)$-alkyl and $(C_1\text{-}C_6)$-alkoxy for their part may in each case be mono- to trisubstituted by identical or different radicals selected from the group consisting of halogen, cyano, oxo, hydroxyl, amino, hydroxycarbonyl, aminocarbonyl, $(C_3\text{-}C_7)$-cycloalkyl, 4- to 7-membered heterocycloalkyl, phenyl, 5- or 6-membered heteroaryl, —C(=O)—$R^4$, —C(=O)—$OR^5$, —C(=O)—$NR^6R^7$, —O—C(=O)—$R^8$, —O—C(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2$—$R^{19}$, —$SO_2$—$R^{20}$, —$SO_2$—$NR^{21}R^{22}$, —$OR^{23}$, —$SR^{24}$ and —$NR^{25}R^{26}$,
where the last-mentioned cycloalkyl, heterocycloalkyl, phenyl and heteroaryl radicals for their part may in each case be substituted up to three times by identical or different substituents selected from the group consisting of halogen, cyano, $(C_1\text{-}C_4)$-alkyl, trifluoromethyl, hydroxyl, $(C_1\text{-}C_4)$-alkoxy, trifluoromethoxy, oxo, amino, mono-$(C_1\text{-}C_4)$-alkylamino, di-$(C_1\text{-}C_4)$-alkylamino, hydroxycarbonyl and $(C_1\text{-}C_4)$-alkoxycarbonyl, (ii) $(C_3\text{-}C_7)$-cycloalkyl, 4- to 7-membered heterocycloalkyl, phenyl and 5- or 6-membered heteroaryl for their part may in each case be mono- to trisubstituted by identical or different radicals selected from the group consisting of $(C_1\text{-}C_6)$-alkyl, halogen, cyano, oxo, hydroxyl, amino, hydroxycarbonyl, aminocarbonyl, —C(=O)—$R^4$, —C(=O)—$OR^5$, —C(=O)—$NR^6R^7$, —O—C(=O)—R$^8$, —O—C(=O)—NR$^9$R$^{10}$, —NR$^{11}$—C(=O)—R$^{12}$, —NR$^{13}$—C(=O)—OR$^{14}$, —NR$^{15}$—C(=O)—NR$^{16}$R$^{17}$, —NR$^{18}$—SO$_2$—R$^{19}$, —SO$_2$—R$^{20}$, —SO$_2$—NR$^{21}$R$^{22}$, —OR$^{23}$, —SR$^{24}$ and —NR$^{25}$R$^{26}$, where the last-mentioned alkyl radical for its part may be substituted up to three times by identical or different substituents from the group consisting of halogen, cyano, hydroxyl, trifluoromethoxy, (C$_1$-C$_4$)-alkoxy, amino, mono-(C$_1$-C$_4$)-alkylamino, di-(C$_1$-C$_4$)-alkylamino, hydroxycarbonyl, (C$_1$-C$_4$)-alkoxycarbonyl, (C$_3$-C$_7$)-cycloalkyl, 4- to 7-membered heterocycloalkyl, phenyl and 5- or 6-membered heteroaryl, (iii) R$^4$, R$^5$, R$^6$, R$^8$, R$^9$, R$^{12}$, R$^{14}$, R$^{16}$, R$^{19}$, R$^{20}$, R$^{21}$, R$^{23}$, R$^{24}$ and R$^{25}$ independently of one another for each individual occurrence represent a radical selected from the group consisting of (C$_1$-C$_6$)-alkyl, (C$_3$-C$_7$)-cycloalkyl, 4- to 7-membered heterocycloalkyl, phenyl and 5- or 6-membered heteroaryl, where (C$_3$-C$_7$)-cycloalkyl, 4- to 7-membered heterocycloalkyl, phenyl and 5- or 6-membered heteroaryl for their part may in each case be substituted up to three times by identical or different substituents selected from the group consisting of halogen, cyano, (C$_1$-C$_4$)-alkyl, trifluoromethyl, hydroxyl, (C$_1$-C$_4$)-alkoxy, trifluoromethoxy, oxo, amino, mono-(C$_1$-C$_4$)-alkylamino, di-(C$_1$-C$_4$)-alkylamino, hydroxycarbonyl and (C$_1$-C$_4$)-alkoxycarbonyl and (C$_1$-C$_6$)-alkyl may be mono- to trisubstituted by identical or different substituents from the group consisting of halogen, cyano, hydroxyl, trifluoromethoxy, (C$_1$-C$_4$)-alkoxy, amino, mono-(C$_1$-C$_4$)-alkylamino, di-(C$_1$-C$_4$)-alkylamino, hydroxycarbonyl, (C$_1$-C$_4$)-alkoxycarbonyl, (C$_3$-C$_7$)-cycloalkyl, 4- to 7-membered heterocycloalkyl, phenyl and 5- or 6-membered heteroaryl, (iv) R$^7$, R$^{10}$, R$^{11}$, R$^{13}$, R$^{15}$, R$^{17}$, R$^{18}$, R$^{22}$ and R$^{26}$ independently of one another for each individual occurrence represent a radical selected from the group consisting of hydrogen and (C$_1$-C$_6$)-alkyl, where (C$_1$-C$_6$)-alkyl may be mono- to trisubstituted by identical or different substituents from the group consisting of halogen, cyano, hydroxyl, trifluoromethoxy, (C$_1$-C$_4$)-alkoxy, amino, mono-(C$_1$-C$_4$)-alkylamino, di-(C$_1$-C$_4$)-alkyl amino, hydroxycarbonyl and (C$_1$-C$_4$)-alkoxycarbonyl, and/or in which (v) R$^6$ and R$^7$, R$^9$ and R$^{10}$, R$^{11}$ and R$^{12}$, R$^{13}$ and R$^{14}$, R$^{15}$ and R$^{16}$, R$^{16}$ and R$^{17}$, R$^{18}$ and R$^{19}$, R$^{21}$ and R$^{22}$ and also R$^{25}$ and R$^{26}$ in each case as a pair together with the atoms to which they are attached may form a 5- or 6-membered heterocycloalkyl ring which may be mono- to trisubstituted by identical or different substituents from the group consisting of halogen, cyano, trifluoromethyl, hydroxyl, (C$_1$-C$_4$)-alkoxy, trifluoromethoxy, oxo, amino, mono-(C$_1$-C$_4$)-alkylamino, alkylamino, hydroxycarbonyl and (C$_1$-C$_4$)-alkoxycarbonyl, m and n independently of one another represent the number 0, 1, 2 or 3, where if R$^1$ or R$^2$ are present more than once, their meanings may in each case be identical or different, and R$^3$ represents hydrogen, (C$_1$-C$_6$)-alkyl or (C$_3$-C$_7$)-cycloalkyl, and salts, solvates and solvates of the salts thereof.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

The compounds according to the invention can exist in stereoisomeric forms (enantiomers, diastereomers), depending on their structure. The invention therefore includes the enantiomers or diastereomers and their particular mixtures. The stereoisomerically uniform constituents can be isolated from such mixtures of enantiomers and/or diastereomers in a known manner.

Where the compounds according to the invention can occur in tautomeric forms, the present invention includes all the tautomeric forms.

Preferred salts in the context of the present invention are physiologically acceptable salts of the compounds according to the invention. Salts which are not themselves suitable for pharmaceutical uses but can be used, for example, for isolation or purification of the compounds according to the invention are also included.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, such as, by way of example and preferably, alkali metal salts (for example sodium and potassium salts), alkaline earth metal salts (for example calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds according to the invention which form a complex in the solid or liquid state by coordination with solvent molecules. Hydrates are a specific form of solvates, in which the coordination takes place with water. Hydrates are preferred solvates in the context of the present invention.

The present invention moreover also includes prodrugs of the compounds according to the invention. The term "prodrugs" includes compounds which themselves can be biologically active or inactive, but are converted (for example metabolically or hydrolytically) into compounds according to the invention during their dwell time in the body.

In the context of the present invention, the substituents have the following meaning, unless specified otherwise:

(C$_1$-C$_6$)-Alkyl and (C$_1$-C$_4$)-alkyl in the context of the invention represent a straight-chain or branched alkyl radical having 1 to 6 or, respectively, 1 to 4 carbon atoms. A straight-chain or branched alkyl radical having 1 to 4 carbon atoms is preferred. There may be mentioned by way of example and preferably: methyl, ethyl, n-propyl, isopropyl, n-butyl, isobutyl, sec-butyl, tert-butyl, 1-ethylpropyl, n-pentyl and n-hexyl.

($C_1$-$C_6$)-Alkoxy and ($C_1$-$C_4$)-alkoxy in the context of the invention represent a straight-chain or branched alkoxy radical having 1 to 6 or, respectively, 1 to 4 carbon atoms. A straight-chain or branched alkoxy radical having 1 to 4 carbon atoms is preferred. There may be mentioned by way of example and preferably: methoxy, ethoxy, n-propoxy, isopropoxy, n-butoxy, tert-butoxy, n-pentoxy and n-hexoxy.

Mono-($C_1$-$C_6$)-alkylamino and mono-($C_1$-$C_4$)-alkylamino in the context of the invention represent an amino group with a straight-chain or branched alkyl substituent which contains 1 to 6 or, respectively, 1 to 4 carbon atoms. A straight-chain or branched monoalkylamino radical having 1 to 4 carbon atoms is preferred. There may be mentioned by way of example and preferably: methylamino, ethylamino, n-propylamino, isopropylamino, n-butylamino, tert-butylamino, n-pentylamino and n-hexylamino.

Di-($C_1$-$C_6$)-alkylamino and di-($C_1$-$C_4$)-alkylamino in the context of the invention represent an amino group with two identical or different straight-chain or branched alkyl substituents which each contain 1 to 6 or, respectively, 1 to 4 carbon atoms. Straight-chain or branched dialkylamino radicals having in each case 1 to 4 carbon atoms are preferred. There may be mentioned by way of example and preferably: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-methyl-N-n-pentylamino and N-n-hexyl-N-methyl-amino.

($C_1$-$C_4$)-Acyl [($C_1$-$C_4$)-alkanoyl] in the context of the invention represents a straight-chain or branched alkyl radical which has 1 to 4 carbon atoms, which carries a doubly attached oxygen atom in the 1-position and which is attached via the 1-position. Preference is given to an acyl radical having 1 to 4 carbon atoms. There may be mentioned by way of example and preferably: formyl, acetyl, propionyl, n-butyryl and isobutyryl.

($C_1$-$C_4$)-Acylamino in the context of the invention represents an amino group having a straight-chain or branched acyl substituent which has 1 to 4 carbon atoms and is attached via the carbonyl group to the nitrogen atom. There may be mentioned by way of example and preferably: formyl-amino, acetylamino, propionylamino, n-butyrylamino and isobutyrylamino.

($C_1$-$C_6$)-Alkoxycarbonyl and ($C_1$-$C_4$)-alkoxycarbonyl in the context of the invention represent a straight-chain or branched alkoxy radical having 1 to 6 or, respectively, 1 to 4 carbon atoms which is linked via a carbonyl group. A straight-chain or branched alkoxycarbonyl radical having 1 to 4 carbon atoms in the alkoxy group is preferred. There may be mentioned by way of example and preferably: methoxycarbonyl, ethoxycarbonyl, n-propoxycarbonyl, isopropoxycarbonyl, n-butoxycarbonyl and tert-butoxycarbonyl.

($C_3$-$C_7$)-Cycloalkyl and ($C_3$-$C_6$)-cycloalkyl in the context of the invention represent a monocyclic, saturated carbocyclic radical having 3 to 7 or, respectively, 3 to 6 ring carbon atoms. There may be mentioned by way of example and preferably: cyclopropyl, cyclobutyl, cyclopentyl, cyclohexyl and cycloheptyl.

4- to 7-membered heterocycloalkyl in the context of the invention represents a monocyclic, saturated heterocycle having a total of 4 to 7 ring atoms which contains one or two ring heteroatoms from the group consisting of N, O and S and is attached via a ring carbon atom or, if appropriate, a ring nitrogen atom. There may be mentioned by way of example: azetidinyl, oxetanyl, thietanyl, pyrrolidinyl, pyrazolidinyl, tetrahydrofuranyl, thiolanyl, 1,3-oxazolidinyl, piperidinyl, piperazinyl, tetrahydropyranyl, tetrahydrothiopyranyl, 1,3-dioxanyl, 1,4-dioxanyl, morpholinyl, thiomorpholinyl, hexahydroazepinyl, hexahydro-1,4-diazepinyl. Preference is given to a 4- to 6-membered heterocycloalkyl radical which has a total of 4 to 6 ring atoms and which contains one or two ring heteroatoms from the group consisting of N and O, such as, for example, pyrrolidinyl, tetrahydrofuranyl, piperidinyl, piperazinyl, tetrahydropyranyl and morpholinyl.

5- or 6-membered heteroaryl in the context of the invention represents an aromatic heterocyclic radical (heteroaromatic) having a total of 5 or, respectively, 6 ring atoms which contains up to four identical or different ring heteroatoms from the group consisting of N, O and S and is linked via a ring carbon atom or optionally via a ring nitrogen atom. There may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl and triazinyl. 5- or 6-membered heteroaryl radicals having up to three ring heteroatoms from the group consisting of N, O and S, such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl and pyrazinyl, are preferred.

Halogen in the context of the invention includes fluorine, chlorine, bromine and iodine. Fluorine, chlorine and bromine are preferred, and fluorine and chlorine are particularly preferred.

If radicals in the compounds according to the invention are substituted, the radicals can be mono- or polysubstituted, unless specified otherwise. In the context of the present invention, for all the radicals which occur several times, the meaning thereof is independent of one another. Substitution by one, two or three identical or different substituents is preferred. Substitution by one or two identical or different substituents is particularly preferred.

Compounds of the formula (I) which are preferred in the context of the present invention are those in which A represents CH, $R^1$ represents a substituent selected from the group consisting of ($C_3$-$C_6$)-cycloalkyl, 4- to 6-membered heterocycloalkyl, phenyl, 5- or 6-membered heteroaryl, —O—C(=O)—NR$^9$R$^{10}$, —NR$^{11}$—C(=O)—R$^{12}$, —NR$^{13}$—C(=O)—OR$^{14}$, —NR$^{15}$—C(=O)—NR$^{16}$R$^{17}$, —NR$^{18}$—SO$_2$—R$^{19}$ and —NR$^{25}$R$^{26}$ in which (i) ($C_3$-$C_6$)-cycloalkyl, 4- to 6-membered heterocycloalkyl, phenyl and 5- or 6-membered heteroaryl for their part may in each case be mono- to trisubstituted by identical or different radicals selected from the group consisting of ($C_1$-$C_6$)-alkyl, halogen, cyano, oxo, hydroxyl, amino, hydroxycarbonyl, aminocarbonyl, —C(=O)—NR$^6$R$^7$, —O—C(=O)—NR$^9$R$^{10}$, —NR$^{11}$—C(=O)—R$^{12}$, —NR$^{13}$—C(=O)—OR$^{14}$, —NR$^{15}$—C(=O)—NR$^{16}$R$^{17}$, —NR$^{18}$—SO$_2$—R$^{19}$, —OR$^{23}$ and —NR$^{25}$R$^{26}$, where the last-mentioned alkyl radical for its part may be substituted up to three times by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl, 4- to 6-membered heterocycloalkyl, phenyl and 5- or 6-membered heteroaryl, (ii) $R^6$, $R^9$, $R^{12}$, $R^{14}$, $R^{16}$, $R^{19}$, $R^{23}$ and $R^{25}$ independently of one another for each individual occurrence represent a radical selected from the group consisting of ($C_1$-$C_6$)-alkyl, ($C_3$-$C_6$)-cycloalkyl and 4- to 6-membered heterocycloalkyl, where ($C_3$-$C_6$)-cycloalkyl and 4- to 6-membered heterocycloalkyl for their part may in each case be substituted up to three times by identical or different substituents selected from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, alkylamino, hydroxycarbonyl and ($C_1$-$C_4$)-alkoxycarbonyl and ($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl and 4- to 6-membered heterocycloalkyl, (iii) $R^7$, $R^{10}$, $R^{11}$, $R^{13}$, $R^{15}$, $R^{17}$, $R^{18}$ and $R^{26}$ independently of one another for each individual occurrence represent a radical selected from the group consisting of hydrogen and ($C_1$-$C_6$)-alkyl, where ($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and ($C_1$-$C_4$)-alkoxycarbonyl, and/or in which (iv) $R^6$ and $R^7$, $R^9$ and $R^{10}$, $R^{11}$ and $R^{12}$, $R^{13}$ and $R^{14}$, $R^{15}$ and $R^{16}$, $R^{16}$ and $R^{17}$, $R^{18}$ and $R^{19}$ and also $R^{25}$ and $R^{26}$ in each case as a pair together with the atoms to which they are attached may form a 5- or 6-membered heterocycloalkyl ring which may be mono- to trisubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, $R^2$ represents a substituent selected from the group consisting of —O—C(=O)—$NR^{9A}R^{10A}$, —$NR^{11A}$—C(=O)—$R^{12A}$, —$NR^{13A}$—C(=O)—$OR^{14A}$, —$NR^{15A}$—C(=O)—$NR^{16A}R^{17A}$, $NR^{18A}$—$SO_2$—$R^{19A}$ and —$NR^{25A}R^{26A}$ in which (i) $R^{9A}$, $R^{12A}$, $R^{14A}$, $R^{16A}$, $R^{19A}$ and $R^{25A}$ independently of one another represent ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, (ii) $R^{10A}$, $R^{11A}$, $R^{13A}$, $R^{15A}$, $R^{17A}$, $R^{18A}$ and $R^{26A}$ independently of one another represent hydrogen or ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, and/or in which (iii) $R^{9A}$ and $R^{16A}$, $R^{11A}$ and $R^{12A}$, $R^{13A}$ and $R^{14A}$, $R^{15A}$ and $R^{16A}$, $R^{16A}$ and $R^{17A}$, $R^{18A}$ and $R^{19A}$ and also $R^{25A}$ and $R^{26A}$ in each case as a pair together with the atoms to which they are attached may form a 5- or 6-membered heterocycloalkyl ring which may be mono- or disubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, m represents the number 1,
n represents the number 0 or 1
and
$R^3$ represents hydrogen, and salts, solvates and solvates of the salts thereof.

Preference in the context of the present invention is also given to compounds of the formula (I) in which A represents CH, $R^1$ represents a substituent selected from the group consisting of ($C_3$-$C_6$)-cycloalkyl, 4- to 6-membered heterocycloalkyl, phenyl, 5- or 6-membered heteroaryl, —O—C(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2$—$R^{19}$ and —$NR^{25}R^{26}$ in which (i) ($C_3$-$C_6$)-cycloalkyl, 4- to 6-membered heterocycloalkyl, phenyl and 5- or 6-membered heteroaryl for their part may in each case be mono- to trisubstituted by identical or different radicals selected from the group consisting of ($C_1$-$C_6$)-alkyl, halogen, cyano, oxo, hydroxyl, amino, hydroxycarbonyl, aminocarbonyl, —C(=O)—$NR^6R^7$, —O—C(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2$—$R^{19}$, —$OR^{23}$ and —$NR^{25}R^{26}$, where the last-mentioned alkyl radical for its part may be substituted up to three times by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl, 4- to 6-membered heterocycloalkyl, phenyl and 5- or 6-membered heteroaryl, (ii) $R^6$, $R^9$, $R^{12}$, $R^{14}$, $R^{16}$, $R^{19}$, $R^{23}$ and $R^{25}$ independently of one another for each individual occurrence represent a radical selected from the group consisting of ($C_1$-$C_6$)-alkyl, ($C_3$-$C_6$)-cycloalkyl and 4- to 6-membered heterocycloalkyl, where ($C_3$-$C_6$)-cycloalkyl and 4- to 6-membered heterocycloalkyl for their part may in each case be substituted up to three times by identical or different substituents selected from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl and ($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl and 4- to 6-membered heterocycloalkyl, (iii) $R^7$, $R^{10}$, $R^{11}$, $R^{13}$, $R^{15}$, $R^7$, $R^{18}$ and $R^{26}$ independently of one another for each individual occurrence represent a radical selected from the group consisting of hydrogen and ($C_1$-$C_6$)-alkyl, where ($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and ($C_1$-$C_4$)-alkoxycarbonyl, and/or in which
(iv) $R^6$ and $R^7$, $R^9$ and $R^{10}$, $R^{11}$ and $R^{12}$, $R^{13}$ and $R^{14}$, $R^5$ and $R^{16}$, $R^{16}$ and $R^{17}$, $R^{18}$ and $R^{19}$ and also $R^{25}$ and $R^{26}$ in each case as a pair together with the atoms to which they are attached may form a 5- or 6-membered heterocycloalkyl ring which may be mono- to trisubstituted by identical or different substituents from the group consisting of halogen, cyano, $(C_1$-$C_4)$-alkyl, trifluoromethyl, hydroxyl, $(C_1$-$C_4)$-alkoxy, trifluoromethoxy, oxo, amino, mono-$(C_1$-$C_4)$-alkylamino, di-$(C_1$-$C_4)$-alkylamino, hydroxycarbonyl and $(C_1$-$C_4)$-alkoxycarbonyl, $R^2$ represents a substituent selected from the group consisting of halogen, cyano, nitro, $(C_1$-$C_6)$-alkyl, trifluoromethyl, hydroxyl, $(C_1$-$C_6)$-alkoxy, trifluoromethoxy, amino, hydroxycarbonyl and —C(=O)—NH—$R^{7A}$ in which $(C_1$-$C_6)$-alkyl and $(C_1$-$C_6)$-alkoxy for their part may be substituted by hydroxyl
and
$R^{7A}$ represents hydrogen or $(C_1$-$C_4)$-alkyl,
m represents the number 1,
n represents the number 0 or 1
and
$R^3$ represents hydrogen,
and salts, solvates and solvates of the salts thereof.

Preference in the context of the present invention is also given to compounds of the formula (I) in
which
A represents CH,
$R^1$ represents a substituent selected from the group consisting of $(C_1$-$C_6)$-alkyl, trifluoromethyl, halogen, cyano, nitro, hydroxyl, $(C_1$-$C_6)$-alkoxy, amino, hydroxycarbonyl, $(C_1$-$C_6)$-alkoxycarbonyl and —C(=O)—NH—$R^7$ in which $(C_1$-$C_6)$-alkyl for its part may be substituted by hydroxyl, $(C_1$-$C_4)$-alkoxy, amino, mono-$(C_1$-$C_4)$-alkylamino, di-$(C_1$-$C_4)$-alkylamino or a group of the formula —NH—C(=O)—$R^{12}$, —NH—C(=O)—NH—$R^{16}$ or —NH—SO$_2$—$R^{19}$ in which
$R^{12}$, $R^{16}$ and $R^{19}$ each represent $(C_1$-$C_6)$-alkyl which may be substituted by hydroxyl or $(C_1$-$C_4)$-alkoxy,
and
$R^7$ represents hydrogen or $(C_1$-$C_6)$-alkyl which may be substituted by hydroxyl or $(C_1$-$C_4)$-alkoxy, $R^2$ represents a substituent selected from the group consisting of —O—C(=O)—NR$^{9A}$R$^{10A}$, —NR$^{11A}$—C(=O)—R$^{12A}$, —NR$^{13A}$—C(=O)—OR$^{14A}$, —NR$^{15A}$—C(=O)—NR$^{16A}$R$^{17A}$, —NR$^{18A}$—SO$_2$—R$^{19A}$ and —NR$^{25A}$R$^{26A}$ in which
(i) $R^{9A}$, $R^{12A}$, $R^{14A}$, $R^{16A}$, $R^{19A}$ and $R^{25A}$ independently of one another represent $(C_1$-$C_6)$-alkyl which may in each case be substituted by halogen, cyano, trifluoromethyl, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl or $(C_1$-$C_4)$-alkoxycarbonyl,
(ii) $R^{10A}$, $R^{11A}$, $R^{13A}$, $R^{15A}$, $R^{17A}$, $R^{18A}$ and $R^{26A}$ independently of one another represent hydrogen or $(C_1$-$C_6)$-alkyl which may in each case be substituted by halogen, cyano, trifluoromethyl, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl or $(C_1$-$C_4)$-alkoxycarbonyl,
and/or in which
(iii) $R^{9A}$ and $R^{10A}$, $R^{11A}$ and $R^{12A}$, $R^{13A}$ and $R^{14A}$, $R^{15A}$ and $R^{16A}$, $R^{16A}$ and $R^{17A}$, $R^{18A}$ and $R^{19A}$ and also $R^{25A}$ and $R^{26A}$ in each case as a pair together with the atoms to which they are attached may form a 5- or 6-membered heterocycloalkyl ring which may be mono- or disubstituted by identical or different substituents from the group consisting of halogen, cyano, $(C_1$-$C_4)$-alkyl, trifluoromethyl, hydroxyl, $(C_1$-$C_4)$-alkoxy, trifluoromethoxy, oxo, amino, mono-$(C_1$-$C_4)$-alkylamino, di-$(C_1$-$C_4)$-alkylamino, hydroxycarbonyl and $(C_1$-$C_4)$-alkoxycarbonyl, m represents the number 1,
n represents the number 0 or 1
and
$R^3$ represents hydrogen,
and salts, solvates and solvates of the salts thereof.

Preference in the context of the present invention is also given to compounds of the formula (I) in which
A represents CH,
$R^1$ represents $(C_1$-$C_6)$-alkyl which
(i) is mono- or disubstituted by identical or different radicals from the group consisting of halogen, cyano, trifluoromethyl, $(C_3$-$C_6)$-cycloalkyl, 4- to 6-membered heterocyclo-alkyl, hydroxycarbonyl, aminocarbonyl, —C(=O)—NR$^6$R$^7$, —O—C(=O)—NR$^9$R$^{10}$, —NR$^{11}$—C(=O)—R$^{12}$, —NR$^{13}$—C(=O)—OR$^{14}$, —NR$^{15}$—C(=O)—NR$^{16}$R$^{17}$, —NR$^{18}$—SO$_2$—R$^{19}$, —OR$^{23}$ and —NR$^{25}$R$^{26}$
and additionally may be substituted by hydroxyl, $(C_1$-$C_4)$-alkoxy, amino, mono-$(C_1$-$C_4)$-alkylamino, di-$(C_1$-$C_4)$-alkylamino or $(C_1$-$C_4)$-acylamino,
or
(ii) is disubstituted by identical or different radicals from the group consisting of hydroxyl, $(C_1$-$C_4)$-alkoxy, amino, mono-$(C_1$-$C_4)$-alkylamino, di-$(C_1$-$C_4)$-alkylamino and $(C_1$-$C_4)$-acylamino
in which
(a) the abovementioned cycloalkyl and heterocycloalkyl radicals for their part may in each case be substituted up to three times by identical or different substituents selected from the group consisting of halogen, cyano, $(C_1$-$C_4)$-alkyl, trifluoromethyl, hydroxyl, $(C_1$-$C_4)$-alkoxy, trifluoromethoxy, oxo, amino, mono-$(C_1$-$C_4)$-alkylamino, di-$(C_1$-$C_4)$-alkylamino, hydroxycarbonyl and $(C_1$-$C_4)$-alkoxy-carbonyl,
(b) $R^7$, $R^{10}$, $R^{11}$, $R^{13}$, $R^{15}$, $R^{17}$, $R^{18}$ and $R^{26}$ independently of one another for each individual occurrence represent a radical selected from the group consisting of hydrogen and $(C_1$-$C_6)$-alkyl,
where $(C_1$-$C_6)$-alkyl may be mono- to trisubstituted by identical or different substituents from the group consisting of halogen, cyano, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl and $(C_1$-$C_4)$-alkoxycarbonyl,
(c) $R^6$, $R^9$ and $R^{14}$ independently of one another for each individual occurrence represent a radical selected from the group consisting of $(C_1$-$C_6)$-alkyl, $(C_3$-$C_6)$-cycloalkyl and 4- to 6-membered heterocycloalkyl,
where
$(C_3$-$C_6)$-cycloalkyl and 4- to 6-membered heterocycloalkyl for their part may in each case be substituted up to three times by identical or different substituents selected from the group consisting of halogen, cyano, $(C_1$-$C_4)$-alkyl, trifluoromethyl, hydroxyl, $(C_1$-$C_4)$-alkoxy, trifluoromethoxy, oxo, amino, mono-$(C_1$-$C_4)$-alkylamino, di-$(C_1$-$C_4)$-alkylamino, hydroxycarbonyl and $(C_1$-$C_4)$-alkoxy-carbonyl
and
$(C_1$-$C_6)$-alkyl may be mono- to trisubstituted by identical or different substituents from the group consisting of halogen, cyano, hydroxyl, trifluoromethoxy, $(C_1$-$C_4)$-alkoxy, amino, mono-$(C_1$-$C_4)$-alkylamino, di-($C_1$-$C_4$)-alkylamino, hydroxycarbonyl, ($C_1$-$C_4$)-alkoxycarbonyl, ($C_3$-$C_6$)-cycloalkyl and 4- to 6-membered heterocycloalkyl, (d) $R^{12}$, $R^{16}$ and $R^{19}$ independently of one another for each individual occurrence represent a radical selected from the group consisting of ($C_1$-$C_6$)-alkyl, ($C_3$-$C_6$)-cycloalkyl and 4- to 6-membered heterocycloalkyl, where ($C_3$-$C_6$)-cycloalkyl and 4- to 6-membered heterocycloalkyl for their part may in each case be substituted up to three times by identical or different substituents selected from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxy-carbonyl and ($C_1$-$C_6$)-alkyl is mono- to trisubstituted by identical or different radicals selected from the group consisting of halogen, cyano, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cyclo-alkyl and 4- to 6-membered heterocycloalkyl, (e) $R^{23}$ and $R^{25}$ independently of one another for each individual occurrence represent a radical selected from the group consisting of ($C_1$-$C_6$)-alkyl, ($C_3$-$C_6$)-cycloalkyl and 4- to 6-membered heterocycloalkyl, where ($C_3$-$C_6$)-cycloalkyl and 4- to 6-membered heterocycloalkyl for their part may in each case be substituted up to three times by identical or different substituents selected from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxy-carbonyl and ($C_1$-$C_6$)-alkyl is mono- to trisubstituted by identical or different radicals selected from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl and 4- to 6-membered heterocycloalkyl, and/or in which (f) $R^6$ and $R^7$, $R^9$ and $R^{10}$, $R^{11}$ and $R^{12}$, $R^{13}$ and $R^{14}$, $R^{15}$ and $R^{16}$, $R^{16}$ and $R^{17}$, $R^{18}$ and $R^{19}$ and also $R^{25}$ and $R^{26}$ in each case as a pair together with the atoms to which they are attached may form a 5- or 6-membered heterocycloalkyl ring which may be mono- to trisubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, $R^2$ represents a substituent selected from the group consisting of halogen, cyano, ($C_1$-$C_6$)-alkyl, trifluoromethyl, hydroxyl, trifluoromethoxy, amino, hydroxycarbonyl, aminocarbonyl, —C(=O)—NR$^{6A}$R$^{7A}$, —O—C(=O)—NR$^{9A}$R$^{10A}$, —NR$^{11A}$—C(=O)—R$^{12A}$, —NR$^{13A}$—C(=O)—OR$^{14A}$, —NR$^{15A}$—C(=O)—NR$^{16A}$R$^{17A}$, —NR$^{18A}$—SO$_2$—R$^{19A}$, —OR$^{23A}$ and —NR$^{25A}$R$^{26A}$ in which (i) ($C_1$-$C_6$)-alkyl may be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkyl-amino, hydroxycarbonyl or ($C_1$-$C_4$)-alkoxycarbonyl, (ii) $R^{6A}$, $R^{9A}$, $R^{12A}$, $R^{14A}$, $R^{16A}$, $R^{19A}$, $R^{23A}$ and $R^{25A}$ independently of one another represent ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, (iii) $R^{7A}$, $R^{10A}$, $R^{11A}$, $R^{13A}$, $R^{15A}$, $R^{17A}$, $R^{18A}$ and $R^{26A}$ independently of one another represent hydrogen or ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, and/or in which (iv) $R^{6A}$ and $R^{7A}$, $R^{9A}$ and $R^{10A}$, $R^{11A}$ and $R^{12A}$, $R^{13A}$ and $R^{14A}$, $R^{15A}$ and $R^{16A}$, $R^{16A}$ and $R^{17A}$, $R^{18A}$ and $R^{19A}$ and also $R^{25A}$ and $R^{26A}$ in each case as a pair together with the atoms to which they are attached may form a 5- or 6-membered heterocycloalkyl ring which may be mono- or disubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, m represents the number 1, n represents the number 0 or 1 and $R^3$ represents hydrogen, and salts, solvates and solvates of the salts thereof.

Preference in the context of the present invention is also given to compounds of the formula (I) in which A represents CH, $R^1$ represents ($C_1$-$C_6$)-alkoxy which is mono- or disubstituted by identical or different radicals selected from the group consisting of halogen, cyano, trifluoromethyl, ($C_3$-$C_6$)-cycloalkyl, 4- to 6-membered heterocycloalkyl, hydroxyl, amino, hydroxycarbonyl, aminocarbonyl, —C(=O)—NR$^6$R$^7$, —O—C(=O)—NR$^9$R$^{10}$, —NR$^{11}$—C(=O)—R$^2$, —NR$^3$—C(=O)—OR$^{14}$, —NR$^{15}$—C(=O)—NR$^{16}$R$^{17}$, —NR$^{18}$—SO$_2$—R$^{19}$, —OR$^{23}$ and —NR$^{25}$R$^{26}$ in which (i) ($C_3$-$C_6$)-cycloalkyl and 4- to 6-membered heterocycloalkyl for their part may in each case be mono- to trisubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, (ii) $R^6$, $R^9$, $R^{12}$, $R^{14}$, $R^{16}$, $R^{19}$, $R^{23}$ and $R^{25}$ independently of one another for each individual occurrence represent a radical selected from the group consisting of ($C_1$-$C_6$)-alkyl, ($C_3$-$C_6$)-cycloalkyl and 4- to 6-membered heterocycloalkyl, where ($C_3$-$C_6$)-cycloalkyl and 4- to 6-membered heterocycloalkyl for their part may in each case be substituted up to three times by identical or different substituents selected from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)- alkylamino, di-($C_1$-$C_4$)-alkylamino, hydroxycarbonyl and ($C_1$-$C_4$)-alkoxycarbonyl
and
($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl and 4- to 6-membered heterocycloalkyl, (iii) $R^7$, $R^{10}$, $R^{11}$, $R^{13}$, $R^{15}$, $R^{17}$, $R^{18}$ and $R^{26}$ independently of one another for each individual occurrence represent a radical selected from the group consisting of hydrogen and ($C_1$-$C_6$)-alkyl,
where ($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and ($C_1$-$C_4$)-alkoxycarbonyl,
and/or in which (iv) $R^6$ and $R^7$, $R^9$ and $R^{10}$, $R^{11}$ and $R^{12}$, $R^{13}$ and $R^{14}$, $R^{15}$ and $R^{16}$, $R^{16}$ and $R^{17}$, $R^{18}$ and $R^{19}$ and also $R^{25}$ and $R^{26}$ in each case as a pair together with the atoms to which they are attached may form a 5- or 6-membered heterocycloalkyl ring which may be mono- to trisubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, $R^2$ represents a substituent selected from the group consisting of halogen, cyano, ($C_1$-$C_6$)-alkyl, trifluoromethyl, hydroxyl, trifluoromethoxy, amino, hydroxycarbonyl, aminocarbonyl, —C(=O)—$NR^{6A}R^{7A}$, —O—C(=O)—$NR^{9A}R^{10A}$, —$NR^{11A}$—C(=O)—$R^{12A}$, —$NR^{13A}$—C(=O)—$OR^{14A}$, —$NR^{15A}$—C(=O)—$NR^{16A}R^{17A}$, —$NR^{18A}$—$SO_2$—$R^{19A}$, —$OR^{23A}$ and —$NR^{25A}R^{26A}$ in which (i) ($C_1$-$C_6$)-alkyl may be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkyl-amino, hydroxycarbonyl or ($C_1$-$C_4$)-alkoxycarbonyl, (ii) $R^{6A}$, $R^{9A}$, $R^{12A}$, $R^{14A}$, $R^{16A}$, $R^{19A}$, $R^{23A}$ and $R^{25A}$ independently of one another represent ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, (iii) $R^{7A}$, $R^{10A}$, $R^{11A}$, $R^{13A}$, $R^{15A}$, $R^{17A}$, $R^{18A}$ and $R^{26A}$ independently of one another represent hydrogen or ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl,
and/or in which (iv) $R^{6A}$ and $R^{7A}$, $R^{9A}$ and $R^{10A}$, $R^{11A}$ and $R^{12A}$, $R^{13A}$ and $R^{14A}$, $R^{15A}$ and $R^{16A}$, $R^{16A}$ and $R^{17A}$, $R^{18A}$ and $R^{19A}$ and also $R^{25A}$ and $R^{26A}$ in each case as a pair together with the atoms to which they are attached may form a 5- or 6-membered heterocycloalkyl ring which may be mono- or disubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, m represents the number 1,
n represents the number 0 or 1
and
$R^3$ represents hydrogen,
and salts, solvates and solvates of the salts thereof.

Preference in the context of the present invention is also given to compounds of the formula (I) in which
A represents CH,
$R^1$ represents the group —C(=O)—$NR^6R^7$
in which (i)
$R^6$ represents ($C_3$-$C_6$)-cycloalkyl or 4- to 6-membered heterocycloalkyl which may in each case be mono- to trisubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl,
or
represents ($C_1$-$C_6$)-alkyl which
(a) is mono- or disubstituted by identical or different radicals selected from the group consisting of halogen, cyano, trifluoromethyl, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl and 4- to 6-membered heterocycloalkyl
and may additionally be substituted by hydroxyl or ($C_1$-$C_4$)-alkoxy,
or
(b) is disubstituted by hydroxyl and/or ($C_1$-$C_4$)-alkoxy,
and
$R^7$ represents hydrogen,
or in which (ii)
$R^6$ represents ($C_1$-$C_6$)-alkyl, ($C_3$-$C_6$)-cycloalkyl or 4- to 6-membered heterocycloalkyl, where
($C_3$-$C_6$)-cycloalkyl and 4- to 6-membered heterocycloalkyl for their part may in each case be substituted up to three times by identical or different substituents selected from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxy-carbonyl
and
($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl and 4- to 6-membered heterocycloalkyl,
and
$R^7$ represents ($C_1$-$C_6$)-alkyl which may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and ($C_1$-$C_4$)-alkoxycarbonyl,
or in which (iii)
$R^6$ and $R^7$ together with the nitrogen atom to which they are attached form a 5- or 6-membered heterocycloalkyl ring which may be mono- to trisubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, $R^2$ represents a substituent selected from the group consisting of halogen, cyano, ($C_1$-$C_6$)-alkyl, trifluoromethyl, hydroxyl, trifluoromethoxy, amino, hydroxycarbonyl, aminocarbonyl, —C(=O)—NR$^{6A}$R$^{7A}$, —O—C(=O)—NR$^{9A}$R$^{10A}$, —NR$^{11A}$—C(=O)—R$^{12A}$, —NR$^{13A}$—C(=O)—OR$^{14A}$, —NR$^{15A}$—C(=O)—NR$^{16A}$R$^{17A}$, —NR$^{18A}$—SO$_2$—R$^{19A}$, —OR$^{23A}$ and —NR$^{25A}$R$^{26A}$ in which (i) ($C_1$-$C_6$)-alkyl may be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkyl-amino, hydroxycarbonyl or ($C_1$-$C_4$)-alkoxycarbonyl, (ii) R$^{6A}$, R$^{9A}$, R$^{12A}$, R$^{14A}$, R$^{16A}$, R$^{19A}$, R$^{23A}$ and R$^{25A}$ independently of one another represent ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, (iii) R$^{7A}$, R$^{10A}$, R$^{11A}$, R$^{13A}$, R$^{15A}$, R$^{17A}$, R$^{18A}$ and R$^{26A}$ independently of one another represent hydrogen or ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, and/or in which (iv) R$^{6A}$ and R$^{7A}$, R$^{9A}$ and R$^{10A}$, R$^{11A}$ and R$^{12A}$, R$^{13A}$ and R$^{14A}$, R$^{15A}$ and R$^{16A}$, R$^{16A}$ and R$^{17A}$, R$^{18A}$ and R$^{19A}$ and also R$^{25A}$ and R$^{26A}$ in each case as a pair together with the atoms to which they are attached may form a 5- or 6-membered heterocycloalkyl ring which may be mono- or disubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl, m represents the number 1,
n represents the number 0 or 1
and
$R^3$ represents hydrogen,
and salts, solvates and solvates of the salts thereof.

Particular preference in the context of the present invention is also given to compounds of the formula (I-A) or (I-B)

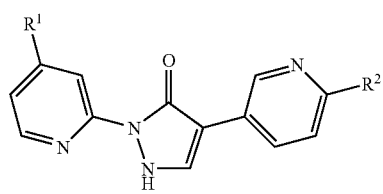
(I-A)

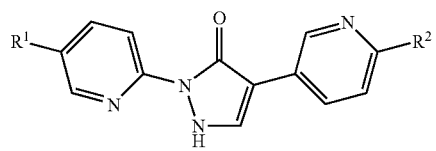
(I-B)

in which
$R^1$ represents 4- to 6-membered heterocycloalkyl, phenyl or 5- or 6-membered heteroaryl which may in each case be mono- or disubstituted by identical or different radicals selected from the group consisting of fluorine, chlorine, bromine, cyano, ($C_1$-$C_4$)-alkyl, hydroxyl, amino, hydroxycarbonyl, —OR$^{23}$ and —NR$^{25}$R$^{26}$ in which ($C_1$-$C_4$)-alkyl for its part may be mono- to trisubstituted by identical or different substituents from the group consisting of fluorine, chlorine, cyano, hydroxyl, ($C_1$-$C_4$)-alkoxy, amino, mono-($C_1$-$C_4$)-alkylamino, di-($C_1$-$C_4$)-alkylamino, hydroxycarbonyl, ($C_3$-$C_6$)-cycloalkyl, 4- to 6-membered heterocycloalkyl, phenyl and 5- or 6-membered heteroaryl, $R^{23}$ and $R^{25}$ independently of one another for each individual occurrence represent ($C_1$-$C_4$)-alkyl which may be mono- to trisubstituted by identical or different substituents from the group consisting of fluorine, chlorine, cyano, hydroxyl, ($C_1$-$C_4$)-alkoxy, amino, mono-($C_1$-$C_4$)-alkylamino, di-($C_1$-$C_4$)-alkylamino, hydroxycarbonyl, ($C_3$-$C_6$)-cycloalkyl and 4- to 6-membered heterocycloalkyl, and $R^{26}$ for each individual occurrence represents hydrogen or ($C_1$-$C_4$)-alkyl which may be mono- to trisubstituted by identical or different substituents from the group consisting of fluorine, chlorine, cyano, hydroxyl, ($C_1$-$C_4$)-alkoxy, amino, mono-($C_1$-$C_4$)-alkylamino, di-($C_1$-$C_4$)-alkylamino and hydroxycarbonyl, and $R^2$ represents hydrogen, fluorine, chlorine, cyano, ($C_1$-$C_4$)-alkyl, trifluoromethyl, hydroxymethyl, ($C_1$-$C_4$)-alkoxy, trifluoromethoxy, amino or hydroxycarbonyl, and salts, solvates and solvates of the salts thereof.

Particular preference in the context of the present invention is also given to compounds of the formula (I-A) or (I-B)

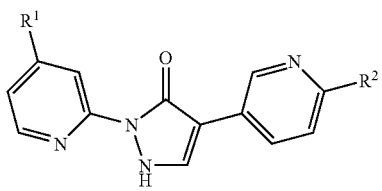
(I-A)

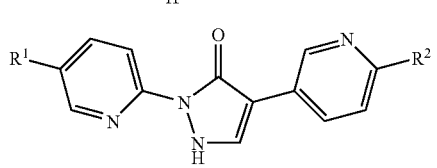
(I-B)

in which
$R^1$ represents ($C_1$-$C_6$)-alkyl which (i) is mono- or disubstituted by identical or different radicals selected from the group consisting of fluorine, chlorine, cyano, trifluoromethyl, ($C_3$-$C_6$)-cycloalkyl, 4- to 6-membered heterocycloalkyl, hydroxycarbonyl, —C(=O)—NR$^6$R$^7$, —O—C(=O)—NR$^9$R$^{10}$, —NR$^{11}$—C(=O)—R$^{12}$, —NR$^{13}$—C(=O)—OR$^{14}$, —NR$^{15}$—C(=O)—NR$^{16}$R$^{17}$, —NR$^{18}$—SO$_2$—R$^{19}$, —OR$^{23}$ and —NR$^{25}$R$^{26}$ and may additionally be substituted by hydroxyl, ($C_1$-$C_4$)-alkoxy, amino, mono-($C_1$-$C_4$)-alkylamino, di-($C_1$-$C_4$)-alkylamino or ($C_1$-$C_4$)-acylamino, or
(ii) is disubstituted by identical or different radicals selected from the group consisting of hydroxyl, $(C_1-C_4)$-alkyl, amino, mono-$(C_1-C_4)$-alkylamino, di-$(C_1-C_4)$-alkylamino and $(C_1-C_4)$-acylamino
in which
(a) the above-mentioned cycloalkyl and heterocycloalkyl radicals for their part may in each case be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkyl-amino, di-$(C_1-C_4)$-alkylamino and hydroxycarbonyl,
(b) $R^7$, $R^{10}$, $R^{11}$, $R^{13}$, $R^{15}$, $R^{17}$, $R^{18}$ and $R^{26}$ independently of one another for each individual occurrence represent a radical selected from the group consisting of hydrogen and $(C_1-C_4)$-alkyl,
where $(C_1-C_4)$-alkyl may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino and hydroxycarbonyl,
(c) $R^6$, $R^9$ and $R^{14}$ independently of one another for each individual occurrence represent a radical selected from the group consisting of $(C_1-C_4)$-alkyl, $(C_3-C_6)$-cycloalkyl and 4- to 6-membered heterocycloalkyl, where
$(C_3-C_6)$-cycloalkyl and 4- to 6-membered heterocycloalkyl for their part may in each case be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkyl-amino, di-$(C_1-C_4)$-alkylamino and hydroxycarbonyl and
$(C_1-C_4)$-alkyl may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino, hydroxycarbonyl, $(C_3-C_6)$-cycloalkyl and 4- to 6-membered heterocycloalkyl,
(d) $R^{12}$, $R^{16}$ and $R^{19}$ independently of one another for each individual occurrence represent a radical selected from the group consisting of $(C_1-C_4)$-alkyl, $(C_3-C_6)$-cycloalkyl and 4- to 6-membered heterocycloalkyl, where
$(C_3-C_6)$-cycloalkyl and 4- to 6-membered heterocycloalkyl for their part may in each case be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkyl-amino, di-$(C_1-C_4)$-alkylamino and hydroxycarbonyl and
$(C_1-C_4)$-alkyl is mono- to trisubstituted by identical or different radicals selected from the group consisting of fluorine, chlorine, cyano, amino, mono-$(C_1-C_4)$-alkylamino, di-$(C_1-C_4)$-alkylamino, hydroxycarbonyl, $(C_1-C_4)$-alkoxycarbonyl, $(C_3-C_6)$-cycloalkyl and 4- to 6-membered heterocycloalkyl,
(e) $R^{23}$ and $R^{25}$ independently of one another for each individual occurrence represent a radical selected from the group consisting of $(C_1-C_4)$-alkyl, $(C_3-C_6)$-cycloalkyl and 4- to 6-membered heterocycloalkyl, where
$(C_3-C_6)$-cycloalkyl and 4- to 6-membered heterocycloalkyl for their part may in each case be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl and
$(C_1-C_4)$-alkyl is mono- to trisubstituted by identical or different radicals selected from the group consisting of fluorine, chlorine, cyano, hydroxyl, $(C_1-C_4)$-alkoxy, amino, mono-$(C_1-C_4)$-alkylamino, di-$(C_1-C_4)$-alkylamino, hydroxycarbonyl, $(C_3-C_6)$-cycloalkyl and 4- to 6-membered heterocycloalkyl,
and/or in which
(f) $R^6$ and $R^7$, $R^9$ and $R^{10}$, $R^{11}$ and $R^{12}$, $R^{13}$ and $R^{14}$, $R^{15}$ and $R^{16}$, $R^{16}$ and $R^{17}$, $R^{18}$ and $R^{19}$ and also $R^{25}$ and $R^{26}$ in each case as a pair together with the atoms to which they are attached may form a 5- or 6-membered heterocycloalkyl ring which may be mono- to trisubstituted by identical or different substituents from the group consisting of fluorine, chlorine, cyano, $(C_1-C_4)$-alkyl, trifluoromethyl, hydroxyl, $(C_1-C_4)$-alkoxy, amino, mono-$(C_1-C_4)$-alkylamino, di-$(C_1-C_4)$-alkylamino and hydroxycarbonyl,
and
$R^2$ represents hydrogen, fluorine, chlorine, cyano, $(C_1-C_4)$-alkyl, trifluoromethyl, hydroxymethyl, $(C_1-C_4)$-alkoxy, trifluoromethoxy, amino or hydroxycarbonyl,
and salts, solvates and solvates of the salts thereof.

Particular preference in the context of the present invention is also given to compounds of the formula (I-A) or (I-B)

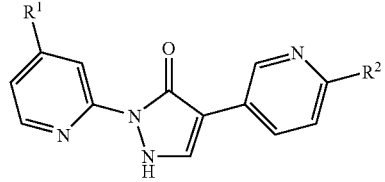

(I-A)

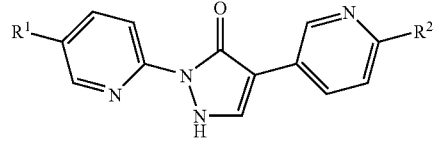

(I-B)

in which
$R^1$ represents $(C_1-C_6)$-alkoxy which is mono- or disubstituted by identical or different radicals selected from the group consisting of fluorine, chlorine, cyano, trifluoromethyl, $(C_3-C_6)$-cycloalkyl, 4- to 6-membered heterocycloalkyl, hydroxyl, amino, hydroxycarbonyl, —C(=O)—NR$^6$R$^7$, —O—C(=O)—NR$^9$R$^{10}$, —NR$^{11}$—C(=O)—R$^2$, —NR$^{13}$—C(=O)—OR$^{14}$, —NR$^{15}$—C(=O)—NR$^{16}$R$^{17}$, —NR$^{18}$—SO$_2$—R$^{19}$, —OR$^{23}$ and —NR$^{25}$R$^{26}$ in which
(i) $(C_3-C_6)$-cycloalkyl and 4- to 6-membered heterocycloalkyl for their part may in each case be mono- to trisubstituted by identical or different substituents from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl,
(ii) $R^6$, $R^9$, $R^{12}$, $R^{14}$, $R^{16}$, $R^{19}$, $R^{23}$ and $R^{25}$ independently of one another for each individual occurrence represent a radical selected from the group consisting of $(C_1-C_4)$-alkyl, $(C_3-C_6)$-cycloalkyl and 4- to 6-membered heterocycloalkyl, where
$(C_3-C_6)$-cycloalkyl and 4- to 6-membered heterocycloalkyl for their part may in each case be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl
and
$(C_1-C_4)$-alkyl may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino, hydroxycarbonyl, $(C_3-C_6)$-cycloalkyl and 4- to 6-membered heterocycloalkyl,
(iii) $R^7$, $R^{10}$, $R^{11}$, $R^{13}$, $R^{15}$, $R^{17}$, $R^{18}$ and $R^{26}$ independently of one another for each individual occurrence represent a radical selected from the group consisting of hydrogen and $(C_1-C_4)$-alkyl,
where $(C_1-C_4)$-alkyl may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino and hydroxycarbonyl,
and/or in which
(iv) $R^6$ and $R^7$, $R^9$ and $R^{10}$, $R^{11}$ and $R^{12}$, $R^{13}$ and $R^{14}$, $R^{15}$ and $R^{16}$, $R^{16}$ and $R^{17}$, $R^{18}$ and $R^{19}$ and also $R^{25}$ and $R^{26}$ in each case as a pair together with the atoms to which they are attached may form a 5- or 6-membered heterocycloalkyl ring which may be mono- to trisubstituted by identical or different substituents from the group consisting of fluorine, chlorine, cyano, $(C_1-C_4)$-alkyl, trifluoromethyl, hydroxyl, $(C_1-C_4)$-alkoxy, amino, mono-$(C_1-C_4)$-alkylamino, di-$(C_1-C_4)$-alkylamino and hydroxycarbonyl,
and
$R^2$ represents hydrogen, fluorine, chlorine, cyano, $(C_1-C_4)$-alkyl, trifluoromethyl, hydroxymethyl, $(C_1-C_4)$-alkoxy, trifluoromethoxy, amino or hydroxycarbonyl,
and salts, solvates and solvates of the salts thereof.

Particular preference in the context of the present invention is also given to compounds of the formula (I-A) or (I-B)

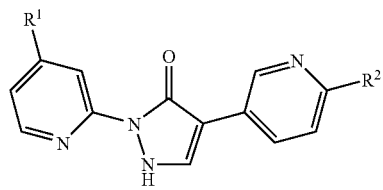

(I-A)

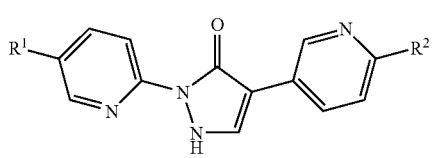

(I-B)

in which
$R^1$ represents the group —C(=O)—NR$^6$R$^7$
in which (i)
$R^6$ represents $(C_3-C_6)$-cycloalkyl or 4- to 6-membered heterocycloalkyl which may in each case be mono- to trisubstituted by identical or different substituents from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl, or
represents $(C_1-C_6)$-alkyl which
(a) is mono- or disubstituted by identical or different radicals selected from the group consisting of fluorine, chlorine, cyano, trifluoromethyl, amino, mono-$(C_1-C_4)$-alkylamino, di-$(C_1-C_4)$-alkylamino, hydroxycarbonyl, $(C_3-C_6)$-cyclo-alkyl and 4- to 6-membered heterocycloalkyl
and may additionally be substituted by hydroxyl or $(C_1-C_4)$-alkoxy,
or
(b) is disubstituted by hydroxyl and/or $(C_1-C_4)$-alkoxy,
and
$R^7$ represents hydrogen,
or in which (ii)
$R^6$ represents $(C_1-C_6)$-alkyl, $(C_3-C_6)$-cycloalkyl or 4- to 6-membered heterocycloalkyl, where
$(C_3-C_6)$-cycloalkyl and 4- to 6-membered heterocycloalkyl for their part may in each case be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl
and
$(C_1-C_6)$-alkyl may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino, hydroxycarbonyl, $(C_3-C_6)$-cycloalkyl and 4- to 6-membered heterocycloalkyl,
and
$R^7$ represents $(C_1-C_4)$-alkyl which may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino and hydroxycarbonyl,
or in which (iii)
$R^6$ and $R^7$ together with the nitrogen atom to which they are attached form a 5- or 6-membered heterocycloalkyl ring which may be mono- to trisubstituted by identical or different substituents from the group consisting of fluorine, chlorine, cyano, $(C_1-C_4)$-alkyl, trifluoromethyl, hydroxyl, $(C_1-C_4)$-alkoxy, amino, mono-$(C_1-C_4)$-alkylamino, di-$(C_1-C_4)$-alkylamino and hydroxycarbonyl,
and
$R^2$ represents hydrogen, fluorine, chlorine, cyano, $(C_1-C_4)$-alkyl, trifluoromethyl, hydroxymethyl, $(C_1-C_4)$-alkoxy, trifluoromethoxy, amino or hydroxycarbonyl,
and their salts, solvates and solvates of the salts.

The radical definitions given in detail in the particular combinations or preferred combinations of radicals are also replaced as desired by radical definitions of other combinations, independently of the particular radical combinations given.

Combinations of two or more of the abovementioned preferred ranges are very particularly preferred.

The 1,2-dihydropyrazol-3-one derivatives of the formula (I) according to the invention can also be in the tautomeric 1H-pyrazol-5-ol form (I') (see Scheme 1 below); the two tautomeric forms are expressly incorporated into the present invention.

Scheme 1

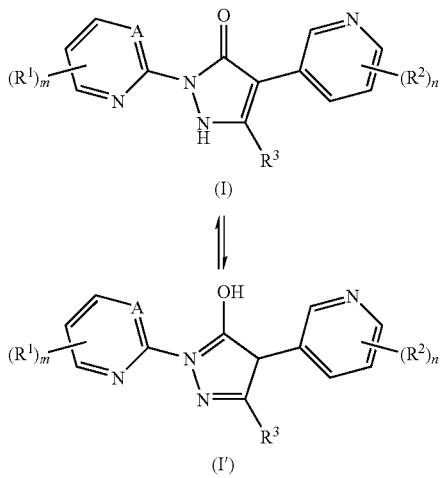

The invention also provides a process for the preparation of the compounds of the formula (I) according to the invention, characterized in that a compound of the formula (II)

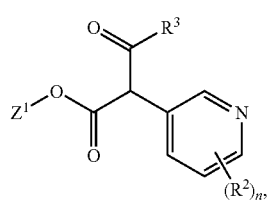

in which $R^2$, $R^3$ and n have the meanings given above and $Z^1$ represents methyl or ethyl,
is reacted in an inert solvent, if appropriate in the presence of an acid, with a compound of the formula (III)

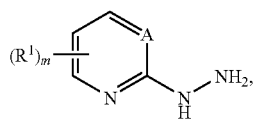

in which A, $R^1$ and m have the meanings given above, to give compounds of the formula (IV)

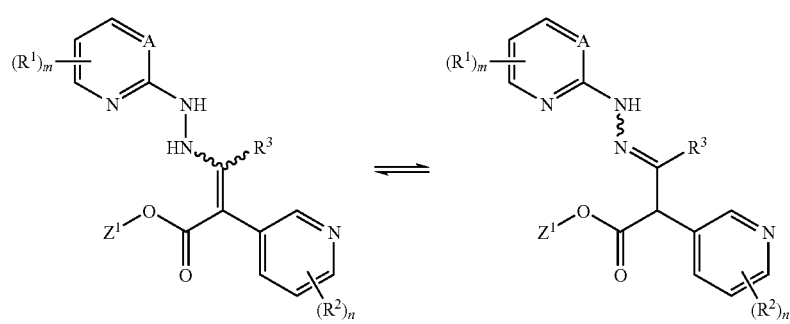

in which $Z^1$, A, $R^1$, $R^2$, $R^3$, m and n have the meanings given above,
which, already under these reaction conditions or in a subsequent reaction step under the influence of a base, cyclize to give the compounds of the formula (I),
and the compounds of the formula (I) are, if appropriate with the appropriate (i) solvents and/or (ii) bases or acids, converted into their solvates, salts and/or solvates of the salts.

The compounds of the formula (I) according to the invention in which $R^3$ represents hydrogen can also be prepared by initially condensing a compound of the formula (V)

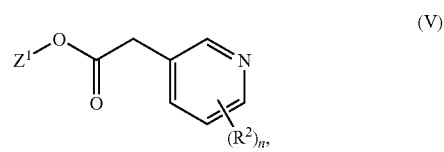

in which $Z^1$, $R^2$ and n have the meanings given above, with a compound of the formula (VI)

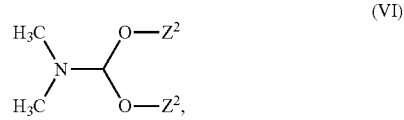

in which
$Z^2$ represents methyl or ethyl,
to give compounds of the formula (VII)

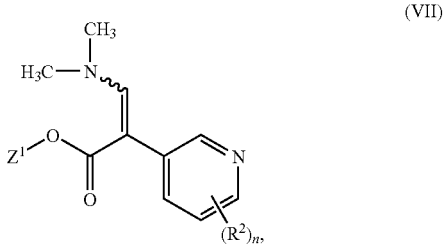

in which $Z^1$, $R^2$ and n have the meanings given above,
and then reacting in the presence of an acid with a compound of the formula (III) to give compounds of the formula (IV-A)

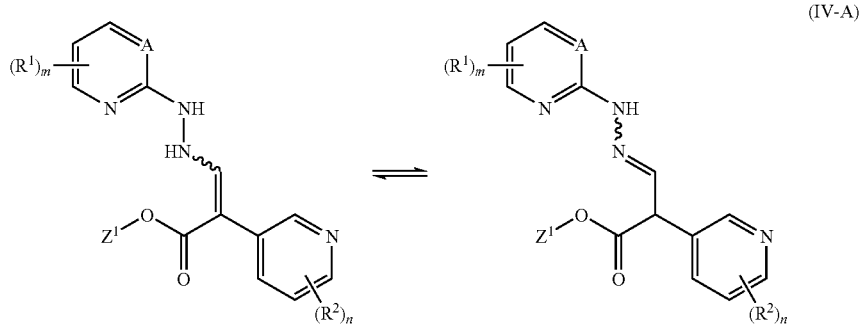

in which $Z^1$, A, $R^1$, $R^2$, m and n have the meanings given above, which, already under these reaction conditions or in a subsequent reaction step under the influence of a base, cyclize to give the compounds of the formula (I) in which $R^3$ represents hydrogen.

Further compounds according to the invention can optionally also be prepared by conversions of functional groups of individual substituents, in particular those listed under $R^1$ and $R^2$, starting from the compounds of the formula (I) obtained by the above processes. These conversions are carried out by conventional methods known to the person skilled in the art and include, for example, reactions such as nucleophilic or electrophilic substitution, oxidation, reduction, hydrogenation, transition metal-catalyzed coupling reactions, alkylation, acylation, amination, esterification, ester cleavage, etherification, ether cleavage, formation of carboxamides, sulfonamides, carbamates and ureas, and the introduction and removal of temporary protective groups.

Suitable inert solvents for the process steps (II)+(III)→(IV), (IV)→(I), (VII)+(III)→(IV-A) and (IV-A)→(I) are, in particular, ethers, such as diethyl ether, methyl tert-butyl ether, 1,2-dimethoxyethane, tetrahydrofuran and dioxane, or alcohols, such as methanol, ethanol, n-propanol, iso-propanol, n-butanol and tert-butanol. Methanol, ethanol tetrahydrofuran or mixtures of these solvents are preferably employed.

The process step (V)+(VI)→(VII) is preferably carried out in dimethylformamide as a solvent or also in the presence of an excess of (VI) without a further solvent. The reaction can also optionally be carried out under microwave irradiation. The reaction in general takes place in a temperature range of from +20° C. to +150° C., preferably at +80° C. to 120° C. [cf. also J. P. Bazureau et al., Synthesis 1998, 967; ibid. 2001 (4), 581].

Process steps (II)+(III)→(IV) and (VII)+(III)→(IV-A) can optionally advantageously be carried out with the addition of an acid. Conventional inorganic or organic acids are suitable for this, such as, for example, hydrogen chloride, acetic acid, trifluoroacetic acid, methanesulfonic acid, p-toluenesulfonic acid or camphor-10-sulfonic acid. Acetic acid or, in particular, camphor-10-sulfonic acid or p-toluenesulfonic acid are preferably used.

The reaction (II)+(III)→(IV) is in general carried out in a temperature range of from 0° C. to +100° C., preferably from +10° C. to +50° C. The reaction (VII)+(III)→(IVA) is in general carried out in a temperature range of from +20° C. to +120° C., preferably at +50° C. to +100° C.

The process sequences (II)+(III)→(IV)→(I) and (VII)+(III)→(IV-A)→(I) can be carried out under a two-stage reaction procedure or also as a one-pot reaction, without isolation of the intermediate stage (IV) or, respectively, (IV-A). For the latter variant, reaction of the components under microwave irradiation is suitable in particular; the reaction here is in general carried out in a temperature range of from +50° C. to +200° C., preferably at +100° C. to +180° C.

In some cases a cyclization to (I) also already occurs even during preparation of (IV) or, respectively, (IV-A); the cyclization can then optionally be brought to completion by in situ treatment of the reaction mixture with a base.

Conventional inorganic or organic bases are suitable as the base for such a separate cyclization step (IV)→(I) or (IV-A)→(I). These include, in particular, alkali metal hydroxides, such as, for example, sodium or potassium hydroxide, alkali metal or alkaline earth metal carbonates, such as sodium, potassium, calcium or cesium carbonate, alkali metal alcoholates, such as sodium or potassium methanolate, sodium or potassium ethanolate or sodium or potassium tert-butylate, or alkali metal hydrides, such as sodium hydride. Sodium methanolate or ethanolate are preferably used.

The base-induced reaction (IV)→(I) or (IV-A)→(I) is in general carried out in a temperature range of from 0° C. to +60° C., preferably at 0° C. to +30° C.

All the process steps can be carried out under atmospheric, elevated or reduced pressure (e.g. from 0.5 to 5 bar). In general, atmospheric pressure is applied.

The compounds of the formula (II) can be prepared by conventional methods from the literature for C-acylation of carboxylic acid esters from compounds of the formula (V). The compounds of the formulae (III), (V) and (VI) are commercially obtainable or known from the literature or can be prepared analogously to processes described in the literature.

The preparation of the compounds according to the invention can be illustrated by reaction scheme 2 below:

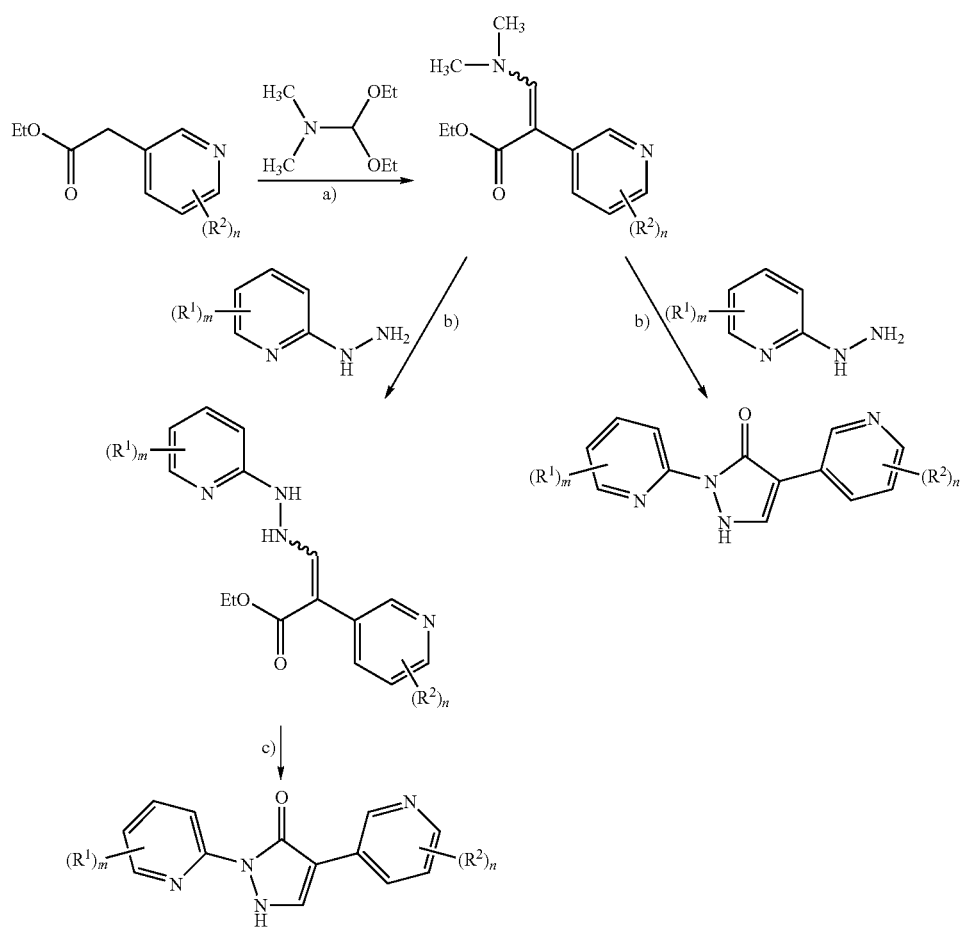

[a): DMF, 16 h, +100° C.; b:) ethanol, cat. camphor-10-sulfonic acid, +78° C.; c): NaOEt, ethanol, 1 h, RT]

The compounds according to the invention show an unforeseeable, valuable pharmacological action spectrum. They are therefore suitable for use as medicaments for treatment and/or prophylaxis of diseases in humans and animals.

The compounds according to the invention are distinguished as specific inhibitors of HIF prolyl 4-hydroxylases.

On the basis of their pharmacological properties, the compounds according to the invention can be employed for treatment and/or prophylaxis of cardiovascular diseases, in particular cardiac insufficiency, coronary heart disease, angina pectoris, myocardial infarction, stroke, arteriosclerosis, essential, pulmonary and malignant hypertension and peripheral arterial occlusive disease.

The compounds according to the invention are furthermore suitable for treatment and/or prophylaxis of blood formation disorders, such as for example idiopathic anemias, renal anemia and anemias accompanying a tumor disease (in particular an anemia induced by chemotherapy), an infection (in particular HIV infection) or another inflammatory disease, such as for example rheumatoid arthritis. The compounds according to the invention are moreover suitable for supporting treatment of anemias as a result of blood loss, iron deficiency anemia, vitamin deficiency anemia (for example as a result of vitamin B12 deficiency or as a result of folic acid deficiency), hypoplastic and aplastic anemia or hemolytic anemia, or for supporting treatment of anemias as a result of iron utilization disorders (sideroachrestic anemia) or anemias as a result of other endocrine disorders (for example hypothyroidosis).

The compounds are furthermore suitable for increasing the hematocrit with the aim of obtaining blood for autodonation of blood before operations.

The compounds according to the invention can moreover be used for treatment and/or prophylaxis of operation-related states of ischemia and consecutive symptoms thereof after surgical interventions, in particular interventions on the heart using a heart-lung machine (for example bypass operations, heart valve implants), interventions on the carotid arteries, interventions on the aorta and interventions with instrumental opening or penetration of the skull cap. The compounds are furthermore suitable for general treatment and/or prophylaxis in the event of surgical interventions with the aim of accelerating wound healing and shortening the convalescence time.

The compounds are moreover suitable for treatment and prophylaxis of consecutive symptoms of acute and protracted ischemic states of the brain (for example stroke, birth asphyxia).

The compounds can furthermore be employed for treatment and/or prophylaxis of cancer and for treatment and/or prophylaxis of an impairment in the state of health occurring in the course of treatment of cancer, in particular after therapy with cytostatics, antibiotics and irradiations.

The compounds are furthermore suitable for treatment and/or prophylaxis of diseases of the rheumatic type and other disease forms to be counted as autoimmune diseases, and in particular for treatment and/or prophylaxis of an impairment in the state of health occurring in the course of medicamentous treatment of such diseases.

The compounds according to the invention can moreover be employed for treatment and/or prophylaxis of diseases of the eye (for example glaucoma), the brain (for example Parkinson's disease, Alzheimer's disease, dementia, chronic pain sensation), of chronic kidney diseases, renal insufficiency and acute renal failure and for promoting wound healing.

The compounds are moreover suitable for treatment and/or prophylaxis of general physical weakness, up to cachexia, in particular occurring to an increased extent at a more elderly age.

The compounds are furthermore suitable for treatment and/or prophylaxis of sexual dysfunction.

The compounds are moreover suitable for treatment and/or prophylaxis of diabetes mellitus and its consecutive symptoms, such as for example diabetic macro- and microangiopathy, diabetic nephropathy and neuropathy.

The compounds according to the invention are moreover suitable for treatment and/or prophylaxis of fibrotic diseases for example of the heart, the lungs and the liver.

In particular, the compounds according to the invention are also suitable for prophylaxis and treatment of retinopathy in premature babies (retinopathia prematurorum).

The present invention moreover provides the use of the compounds according to the invention for treatment and/or prevention of diseases, in particular the abovementioned diseases.

The present invention moreover provides the use of the compounds according to the invention for the preparation of a medicament for treatment and/or prevention of diseases, in particular the abovementioned diseases.

The present invention moreover provides a method for treatment and/or prevention of diseases, in particular the abovementioned diseases, using an active amount of at least one of the compounds according to the invention.

The compounds according to the invention can be employed by themselves or, if required, in combination with other active compounds. The present invention moreover provides medicaments comprising at least one of the compounds according to the invention and one or more further active compounds, in particular for treatment and/or prevention of the abovementioned diseases. Suitable active compounds in the combination which may be mentioned by way of example and preferably are: ACE inhibitors, angiotensin II receptor antagonists, beta receptor blockers, calcium antagonists, PDE inhibitors, mineralocorticoid receptor antagonists, diuretics, aspirin, iron supplements, vitamin B12 and folic acid supplements, statins, digitalis (digoxin) derivatives, tumor chemotherapeutics and antibiotics.

In a preferred embodiment of the invention, the compounds according to the invention are administered in combination with an ACE inhibitor, such as, by way of example and preferably, enalapril, captopril, lisinopril, ramipril, delapril, fosinopril, quinoprol, perindopril or trandopril.

In a preferred embodiment of the invention, the compounds according to the invention are administered in combination with an angiotensin AII antagonist, such as, by way of example and preferably, losartan, candesartan, valsartan, telmisartan or embusartan.

In a preferred embodiment of the invention, the compounds according to the invention are administered in combination with a beta receptor blocker, such as, by way of example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a calcium antagonist, such as, by way of example and preferably, nifedipine, amlopidine, verapamil or diltiazem.

In a preferred embodiment of the invention, the compounds according to the invention are administered in combination with a phosphodiesteras (PDE) inhibitor, such as, by way of example and preferably, milrinone, aminone, pimobendan, cilostazol, sildenafil, vardenafil or tadalafil.

In a preferred embodiment of the invention, the compounds according to the invention are administered in combination with a mineralocorticoid receptor antagonist, such as, by way of example and preferably, spironolactone, eplerenone, canrenone or potassium canrenoate.

In a preferred embodiment of the invention the compounds according to the invention are administered in combination with a diuretic, such as, by way of example and preferably, furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerin, isosorbide, mannitol, amiloride or triamterene.

In a preferred embodiment of the invention, the compounds according to the invention are administered in combination with an HMG-CoA reductase inhibitor from the class of statins, such as, by way of example and preferably, lovastatin, simvastatin, pravastatin, fluvastatin, atorvastatin, rosuvastatin, cerivastatin or pitavastatin.

In a preferred embodiment of the invention, the compounds according to the invention are administered in combination with a tumor chemotherapeutic, by way of example and preferably from the group consisting of platinum complexes, such as for example cisplatin and carboplatin, the alkylating agents, such as for example cyclophosphamide and chlorambucil, the antimetabolites, such as for example 5-fluorouracil and methotrexate, the topoisomerase inhibitors, such as for example etoposide and camptothecin, the antibiotics, such as for example doxorubicin and daunorubicin, or the kinase inhibitors, such as for example sorafenib and sunitinib.

In a preferred embodiment of the invention, the compounds according to the invention are administered in combination with an antibiotic, by way of example and preferably from the group consisting of penicillins, cephalosporins or quinolones, such as for example ciprofloxacin and moxifloxacin.

The present invention moreover provides medicaments which comprise at least one compound according to the invention, conventionally together with one or more inert, non-toxic, pharmaceutically suitable auxiliary substances, and the use thereof for the above-mentioned purposes.

The compounds according to the invention can act systemically and/or locally. They can be administered in a suitable manner for this purpose, such as for example orally, parenterally, pulmonally, nasally, sublingually, lingually, buccally, rectally, dermally, transdermally, conjunctivally, otically or as an implant or stent.

The compounds according to the invention can be administered in suitable administration forms for these administration routes.

Administration forms which function according to the prior art, release the compounds according to the invention rapidly and/or in a modified manner and comprise the compounds according to the invention in crystalline and/or amorphized and/or dissolved form are suitable for oral administration, such as for example tablets (non-coated or coated tablets, for example coatings which are resistant to gastric juice or dissolve in a delayed manner or are insoluble and control the release of the compound according to the invention), tablets or films/wafers, films/lyophilizates or capsules which disintegrate rapidly in the oral cavity (for example hard or soft gelatin capsules), sugar-coated tablets, granules, pellets, powders, emulsions, suspensions, aerosols or solutions.

Parenteral administration can be effected with bypassing of an absorption step (for example intravenously, intraarterially, intracardially, intraspinally or intralumbally) or with inclusion of an absorption (for example intramuscularly, subcutaneously, intracutaneously, percutaneously or intraperitoneally). Administration forms which are suitable for parenteral administration are, inter alia, injection and infusion formulations in the form of solutions, suspensions, emulsions, lyophilizates or sterile powders.

For the other administration routes, for example, inhalation medicament forms (inter alia powder inhalers, nebulizers), nasal drops, solutions or sprays, tablets, films/wafers or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (for example patches), milk, pastes, foams, sprinkling powders, implants or stents are suitable.

Oral and parenteral administration are preferred, in particular oral and intravenous administration.

The compounds according to the invention can be converted into the administration forms mentioned. This can be effected in a manner known per se by mixing with inert, non-toxic, pharmaceutically suitable auxiliary substances. These auxiliary substances include inter alia carrier substances (for example microcrystalline cellulose, lactose, mannitol), solvents (for example liquid polyethylene glycols), emulsifiers and dispersing or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), dyestuffs (for example inorganic pigments, such as, for example, iron oxides) and flavor and/or smell correctants.

In general, it has proved advantageous in the case of parenteral administration to administer amounts of from about 0.001 to 1 mg/kg, preferably about 0.01 to 0.5 mg/kg of body weight to achieve effective results. In the case of oral administration the dosage is about 0.01 to 100 mg/kg, preferably about 0.01 to 20 mg/kg and very particularly preferably 0.1 to 10 mg/kg of body weight.

Nevertheless it may be necessary to deviate from the amounts mentioned, and in particular depending on the body weight, administration route, individual behavior towards the active compound, nature of the formulation and point in time or interval at which administration takes place. Thus in some cases it may be sufficient to manage with less than the above-mentioned minimum amount, while in other cases the upper limit mentioned must be exceeded. In the case where relatively large amounts are administered, it may be advisable to distribute these into several individual doses over the day.

The following embodiment examples illustrate the invention. The invention is not limited to the examples.

The percentage data in the following tests and examples are percentages by weight, unless stated otherwise; parts are parts by weight. The solvent ratios, dilution ratios and concentration data of liquid/liquid solutions in each case relate to the volume.

A. EXAMPLES

Abbreviations And Acronyms

| | |
|---|---|
| aq. | aqueous solution |
| cat. | catalytic |
| d | day(s) |
| DCI | direct chemical ionization (in MS) |
| DMF | dimethylformamide |
| DMSO | dimethyl sulfoxide |
| EI | electron impact ionization (in MS) |
| ESI | electrospray ionization (in MS) |
| Et | ethyl |
| GC-MS | gas chromatography-coupled mass spectroscopy |
| h | hour(s) |
| HPLC | high pressure, high performance liquid chromatography |
| conc. | concentrated |
| LC-MS | liquid chromatography-coupled mass spectroscopy |
| Meth. | method |
| min | minute(s) |
| MS | mass spectroscopy |
| NMR | nuclear magnetic resonance spectroscopy |
| $R_t$ | retention time (in HPLC) |
| RT | room temperature |
| TFA | trifluoroacetic acid |
| THF | tetrahydrofuran |

LC-MS, GC-MS and HPLC Methods:

Method 1:

Instrument: Micromass Platform LCZ mit HPLC Agilent Serie 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 2:

MS instrument type: Micromass ZQ; HPLC instrument type: HP 1100 Series; UV DAD; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 3:

MS instrument: Micromass TOF (LCT); HPLC instrument: Waters 2690; autosampler: Waters 2700; column: YMC-ODS-AQ, 50 mm×4.6 mm, 3.0 min; mobile phase A: water+0.1% formic acid, mobile phase B: acetonitrile+0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Method 4:

MS instrument: Waters ZQ 2000; HPLC instrument: Agilent 1100, 2-column system; autosampler: HTC PAL; column: YMC-ODS-AQ, 50 mm×4.6 mm, 3.0 min; mobile phase A: water+0.1% formic acid, mobile phase B: acetonitrile+0.1% formic acid; gradient: 0.0 min 100% A→0.2 min 95% A→1.8 min 25% A→1.9 min 10% A→2.0 min 5%

A→3.2 min 5% A→3.21 min 100% A→3.35 min 100% A; oven: 40° C.; flow rate: 3.0 ml/min; UV detection: 210 nm.

Method 5:

Instrument: Micromass QuattroPremier with Waters HPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 6:

Instrument: Micromass Quattro Micro MS with HPLC Agilent Serie 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)-5.00 min 100% A; oven: 50° C.; flow rate: 2 ml/min; UV detection: 210 nm.

Method 7:

MS instrument type: Waters ZQ; HPLC instrument type: Agilent 1100 Series; UV DAD; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100% A; flow rate: 2.5 ml/min; oven: 55° C.; UV detection: 210 nm.

Method 8:

MS instrument: Micromass TOF (LCT); HPLC instrument: Waters 2690; autosampler: Waters 2700; column: YMC-ODS-AQ, 3μ, 50 mm×4.6 mm; mobile phase A: water+0.1% formic acid, mobile phase B: acetonitrile+0.1% formic acid; gradient: 0.0 min 100% A→0.2 min 95% A→1.8 min 25% A→1.9 min 10% A→2 min 5% A→3.2 min 5% A→3.21 min 100% A→3.35 min 100% A; oven: 40° C.; flow rate: 3 ml/min; UV detection: 210 nm.

Method 9:

MS instrument: Waters ZQ 2000; HPLC instrument: Agilent 1100, 2-column system; autosampler: HTC PAL; column: YMC-ODS-AQ, 50 mm×4.6 mm, 3.0 min; mobile phase A: water+0.1% formic acid, mobile phase B: acetonitrile+0.1% formic acid; gradient: 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Method 10:

Instrument: HP 1100 with DAD detection; column: Kromasil 100 RP-18, 60 mm×2.1 mm, 3.5 min; mobile phase A: 5 ml of perchloric acid (70% strength)/liter of water, mobile phase B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

Method 11:

Instrument: Micromass GCT, GC6890; column: Restek RTX-35, 15 m×200 m×0.33 min; constant helium flow rate: 0.88 ml/min; oven: 70° C.; inlet: 250° C.; gradient: 70° C., 30° C./min→310° C. (maintained for 3 min).

Starting Materials and Intermediates

Example 1A

2-Hydrazinoisonicotinonitrile

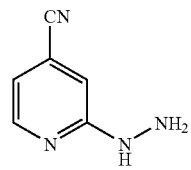

20.0 g (144 mmol) of 2-chloroisonicotinonitrile are initially charged in 150 ml of 1-butanol, 303 ml (303 mmol) of a 1 M solution of hydrazine hydrate in THF are added and the mixture is heated for 16 h (bath temperature 110° C.). The mixture is concentrated and the residue is purified by flash chromatography on silica gel (mobile phase: dichloromethane/methanol 10:1).

Yield: 9.48 g (49% of theory)

$^1$H-NMR (400 MHz, DMSO-d$_6$): δ=8.15 (d, 1H), 8.05 (s, 1H), 7.01 (s, 1H), 6.83 (dd, 1H), 4.30 (s, 2H).

LC-MS (Method 1): R$_t$=0.52 min; MS (ESIpos): m/z=135 [M+H]$^+$.

Example 2A

Ethyl 3-(dimethylamino)-2-pyridin-3-ylacrylate

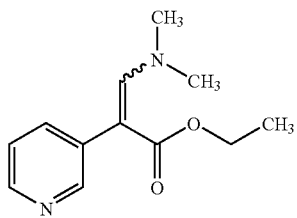 [SMILES: CCOC(=O)C(=CN(C)C)c1cccnc1]

37.4 g (226 mmol) of ethyl pyridin-3-ylacetate in 100 g (679 mmol) of dimethylformamide diethyl acetal are heated at 100° C. overnight. After cooling, the mixture is concentrated and the residue is prepurified by flash chromatography on silica gel (mobile phase: gradient cyclohexane/ethyl acetate 1:1→ethyl acetate/ethanol 9:1). The resulting product is subjected to fine purification by vacuum distillation (1 mbar, 200° C. bath temperature).

Yield: 35.0 g (70% of theory)

$^1$H-NMR (400 MHz, DMSO-d$_6$): δ=8.37 (dd, 1H), 8.31 (dd, 1H), 7.59 (s, 1H), 7.51 (dt, 1H), 7.29 (ddd, 1H), 4.00 (q, 2H), 2.67 (s, 6H), 1.11 (t, 3H).

LC-MS (Method 1): R$_t$=2.38 min; MS (ESIpos): m/z=221 [M+H]$^+$.

Example 3A 2-(4-Cyanopyridin-2-yl)-4-pyridin-3-yl-1,2-dihydro-3H-pyrazol-3-one

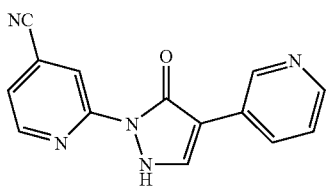

545 mg (4.06 mmol) of the compound from Example 1A and 1.07 g (4.88 mmol) of the compound from Example 2A in 15 ml of glacial acetic acid are stirred at RT for 2 h. The mixture is concentrated and the residue is taken up in 300 ml of ethyl acetate and washed repeatedly with saturated sodium bicarbonate solution. The organic phase is dried over sodium sulfate, filtered and concentrated. The residue is taken up in 30 ml of ethanol, 1.33 g (4.88 mmol) of a 25% strength solution of sodium ethoxide in ethanol are added at RT and the mixture is stirred for 30 min. The pH is adjusted to 5 by addition of 1 M hydrochloric acid, and the solid formed is filtered off with suction, washed with diethyl ether and dried under high vacuum.

Yield: 890 mg (83% of theory)

$^1$H-NMR (400 MHz, DMSO-$d_6$): δ=9.01-8.98 (m, 2H), 8.54 (dd, 1H), 8.18 (dt, 1H), 8.01 (dd, 1H), 7.85 (s, 1H), 7.39 (dd, 1H), 7.14 (dd, 1H).

LC-MS (Method 2): $R_t$=1.13 min; MS (ESIpos): m/z=264 [M+H]$^+$.

Example 4A

2-[4-(Aminomethyl)pyridin-2-yl]-4-pyridin-3-yl-1,2-dihydro-3H-pyrazol-3-one dihydrochloride

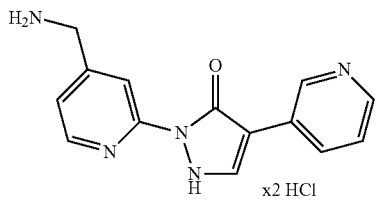 [SMILES: NCc1ccnc(-n2[nH]cc(-c3cccnc3)c2=O)c1]

100 mg (380 µmol) of the compound from Example 3A are dissolved in 10 ml of glacial acetic acid, 50.0 mg of catalyst (10% palladium on carbon) are added and the mixture is stirred under an atmosphere of hydrogen at atmospheric pressure and RT overnight. The reaction mixture is then filtered and concentrated, and the residue is purified by preparative HPLC (RP18-column; mobile phase: acetonitrile/water-gradient with addition of 0.1% conc. hydrochloric acid).

Yield: 64 mg (49% of theory)

$^1$H-NMR (400 MHz, DMSO-$d_6$): δ=9.38 (s, 1H), 8.93 (d, 1H), 8.79 (s, 1H), 8.75 (s, 3H), 8.64 (d, 1H), 8.56 (d, 1H), 8.48 (s, 1H), 7.99 (dd, 1H), 7.54 (d, 1H), 4.21 (q, 2H).

LC-MS (Method 1): $R_t$=1.39 min; MS (ESIpos): m/z=268 [M+H]$^+$.

Example 5A 1-(6-Hydrazinopyridin-3-yl)-N-methylmethanamine

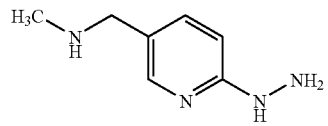

1.0 g (6.4 mmol) of 1-(6-chloropyridin-3-yl)-N-methylmethanamine [for the preparation, see EP 0 556 684-A1] are initially charged in 1.5 ml (1.6 g, 31.9 mmol) of hydrazine hydrate and stirred at boiling point at a bath temperature of 150° C. for 12 h. The reaction solution is cooled and concentrated, and the residue is dried under reduced pressure. This gives 1.1 g of the title compound, which is used without any further purification.

LC-MS (Method 1): $R_t$=0.52 min; MS (ESIpos): m/z=153 [M+H]$^+$.

Example 6A

N-[(6-Hydrazinopyridin-3-yl)methyl]-2-methoxyethanamine

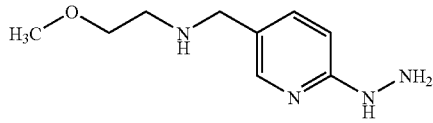

3.6 g (17.7 mmol) of N-[(6-chloropyridin-3-yl)methyl]-2-methoxyethanamine [prepared analogously to WO 2004/081007] are initially charged in 4.3 ml (4.4 g, 88.5 mmol) of hydrazine hydrate and stirred at boiling point at a bath temperature of 150° C. for 16 h. The reaction solution is cooled and concentrated, and the residue is purified by column chromatography on silica gel (mobile phase: acetonitrile/water 9:1).

Yield: 1.6 g (47% of theory)

LC-MS (Method 1): $R_t$=0.44 min; MS (ESIpos): m/z=197 [M+H]$^+$.

Example 7A

2-Hydrazino-5-(methylsulfonyl)pyridine

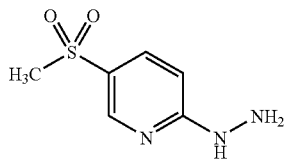

1.7 ml (1.7 g, 34.0 mmol) of hydrazine hydrate are added to 2.0 g (8.5 mmol) of 2,5-bis(methylsulfonyl)pyridine [Woods et al., J. Heterocycl. Chem. 1984, 21, 97-101] in 15 ml of ethanol, and the mixture is stirred under reflux for 4 h. For work-up, the reaction solution is cooled to 15° C., the precipitated solid is filtered off, the filter residue is washed with ethanol and diethyl ether and the product is dried under reduced pressure.

Yield: 1.4 g (89% of theory)

LC-MS (Method 1): $R_t$=0.51 min; MS (ESIpos): m/z=188 [M+H]$^+$;

$^1$H-NMR (400 MHz, DMSO-d$_6$): δ=8.56 (s, 1H), 8.38 (d, 1H), 7.81 (dd, 1H), 6.79 (d, 1H), 4.42 (s, 2H), 3.11 (s, 3H).

Example 8A

Ethyl (5-bromopyridin-3-yl)acetate

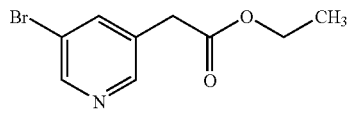

15 drops of concentrated sulfuric acid are added to 5.0 g (23.1 mmol) of (5-bromopyridin-3-yl)acetic acid in 30 ml of ethanol, and the mixture is heated under reflux for 16 h. After cooling to RT, the mixture is concentrated under reduced pressure and the residue is taken up in ethyl acetate and washed with semiconcentrated sodium bicarbonate solution. The organic phase is dried over sodium sulfate, filtered and concentrated under reduced pressure.

Yield: 5.2 g (91% of theory)

LC-MS (Method 2): $R_t$=1.48 min; MS (ESIpos): m/z=244 [M+H]$^+$;

$^1$H-NMR (400 MHz, DMSO-d$_6$): δ=8.61 (d, 1H), 8.48 (d, 1H), 8.00 (dd, 1H), 4.10 (q, 2H), 3.33 (s, 2H), 1.20 (t, 3H).

Example 9A

Ethyl (2Z)-2-(5-bromopyridin-3-yl)-3-(dimethylamino)prop-2-enoate

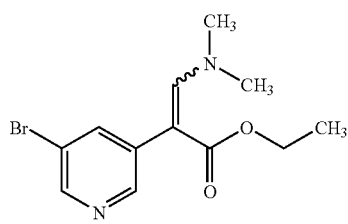 [SMILES: CCOC(=O)C(=CN(C)C)c1cncc(Br)c1]

5.1 g (20.8 mmol) of the compound from Example 8A in 7.1 ml (6.2 g, 41.8 mmol) of dimethylformamide diethyl acetal are heated at 100° C. for 16 h. After cooling, the mixture is concentrated under reduced pressure.

Yield: 6.1 g (73% of theory)

LC-MS (Method 6): $R_t$=1.86 min; MS (ESIpos): m/z=299 [M+H]$^+$.

Example 10A

2-Hydrazino-4-methylpyridine

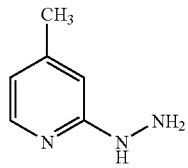

3.3 g (30.0 mmol) of 2-fluoro-4-methylpyridine are initially charged in 40 ml of ethylene glycol monoethyl ether, 14.6 ml (15.0 g, 300 mmol) of hydrazine hydrate are added to the solution and the mixture is stirred at boiling point (bath temperature 150° C.) for 16 h. The reaction solution is then concentrated on a rotary evaporator, and the residue is added to 100 ml of water and extracted with ethyl acetate (three times 100 ml each). The combined organic phases are dried over sodium sulfate, filtered and concentrated. The residue obtained is dried under reduced pressure.

Yield: 1.90 g (51% of theory)

LC-MS (Method 1): $R_t$=0.80 min; MS (ESIpos): m/z=124 [M+H]$^+$;

$^1$H-NMR (400 MHz, DMSO-d$_6$): δ=7.83 (d, 1H), 7.22 (s, 1H), 6.51 (s, 1H), 6.38 (d, 1H), 4.04 (s, 2H), 2.17 (s, 3H).

Example 11A

2-Hydrazino-5-methylpyridine

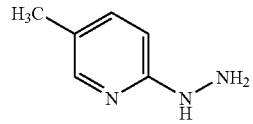

5.7 ml (5.9 g, 117.6 mmol) of hydrazine hydrate are added to 1.0 g (7.8 mmol) of 2-chloro-5-methylpyridine, and the mixture is stirred at boiling point (bath temperature 150° C.) for 16 h. The reaction mixture is cooled and then concentrated on a rotary evaporator, and the residue is co-evaporated three times with in each case 10 ml of ethylene glycol monoethyl ether. The residue is then taken up in dichloromethane, the precipitate is separated off and the filtrate is concentrated under reduced pressure.

Yield: 644 mg (67% of theory)

LC-MS (Method 6): $R_t$=0.35 min; MS (ESIpos): m/z=124 [M+H]$^+$.

Example 12A

2-Chloro-5-(methoxymethyl)pyridine

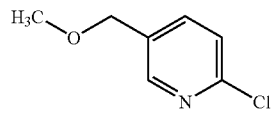

2.6 g (23.0 mmol) of potassium tert-butoxide are dissolved in 50 ml of THF. 3.0 g (20.9 mmol) of (6-chloropyridin-3-yl)methanol are added, and the mixture is stirred at RT for 15 min. 4.4 g (31.3 mmol) of iodomethane are then added slowly, and the mixture is stirred for about 30 min until the slightly exothermic reaction has subsided. The solvent is removed, and the residue is taken up in dichloromethane and washed twice with water. The organic phase is dried over magnesium sulfate and concentrated, and the residue is purified by column chromatography on silica gel (Biotage chromatography, mobile phase: cyclohexane/ethyl acetate 85:15).

Yield: 2.2 g (68% of theory)

LC-MS (Method 1): $R_t$=2.62 min; MS (ESIpos): m/z=158 [M+H]$^+$;

$^1$H-NMR (400 MHz, CDCl$_3$): δ=8.34 (d, 1H), 7.65 (dd, 1H), 7.32 (d, 1H), 4.45 (s, 2H), 3.41 (s, 3H).

Example 13A 5-(tert-Butoxymethyl)-2-chloropyridine

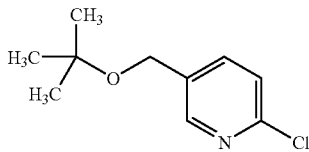

7.2 g (50.0 mmol) of (6-chloropyridin-3-yl)methanol are initially charged in 50 ml of dichloromethane. 25.1 g (115.0 mmol) of di-tert-butyl dicarbonate and 1.1 g (5.0 mmol) of magnesium perchlorate are added, and the mixture is stirred at 40° C. for 24 h. The mixture is then cooled to RT, a further 12.5 g (57.3 mmol) of di-tert-butyl dicarbonate and 600 mg (2.7 mmol) of magnesium perchlorate are added, and the mixture is stirred under reflux for another 2.5 h. Another 12.5 g (57.3 mmol) of di-tert-butyl dicarbonate are added, and the mixture is stirred under reflux for another 3 h. The mixture is then diluted with dichloromethane and washed once with water and once with saturated sodium chloride solution. The mixture is dried over magnesium sulfate and concentrated, and the residue is purified by column chromatography on silica gel (mobile phase: cyclohexane/ethyl acetate 85:15).

Yield: 7.9 g (79% of theory)

LC-MS (Method 5): $R_t$=1.12 min; MS (ESIpos): m/z=200 [M+H]$^+$;

$^1$H-NMR (400 MHz, DMSO-d$_6$): δ=8.35 (d, 1H), 7.78 (dd, 1H), 7.48 (d, 1H), 4.45 (s, 2H), 1.22 (s, 9H).

Example 14A

6-Hydrazinopyridine-3-carbonitrile

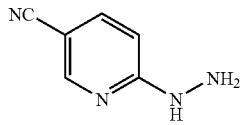

90.3 g (1.8 mol) of hydrazine hydrate are added to 25.0 g (180.0 mmol) of 6-chloronicotinonitrile, and the mixture is stirred at a bath temperature of 100° C. for 15 min. The reaction mixture is cooled to RT, diluted with water and stirred at RT for 30 min. The precipitate formed is filtered off, the filter residue is washed with water and the crystals are air-dried for 24 h and recrystallized once from ethyl acetate.

Yield: 18.7 g (77% of theory)

LC-MS (Method 1): $R_t$=0.51 min; MS (ESIpos): m/z=135 [M+H]$^+$;

$^1$H-NMR (400 MHz, DMSO-d$_6$)=8.58 (s, 1H), 8.33 (s, 1H), 7.74 (d, 1H), 6.76 (br. s, 1H), 4.42 (s, 2H).

Example 15A tert-Butyl 6-hydrazinopyridine-3-carboxylate

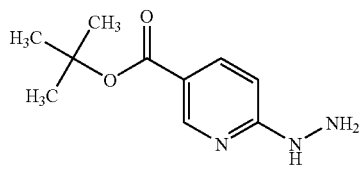

18.0 g (84.2 mmol) of tert-butyl 6-chloropyridine-3-carboxylate are initially charged in 85 ml of ethanol. 42.2 g (842.0 mmol) of hydrazine hydrate are added, and the mixture is stirred at 100° C. for 2 h. The mixture is then concentrated, and the residue is taken up in a mixture of ethyl acetate and water. The phases are separated, and the organic phase is washed once with water and once with saturated sodium chloride solution, dried over magnesium sulfate and concentrated again. The residue is triturated with petroleum ether, and the solid formed is filtered off and dried under high vacuum.

Yield: 16.4 g (78% of theory)

LC-MS (Method 1): $R_t$=2.30 min; MS (ESIpos): m/z=210 [M+H]$^+$;

$^1$H-NMR (400 MHz, DMSO-d$_6$): δ=8.49 (d, 1H), 8.30 (s, 1H), 7.82 (dd, 1H), 6.70 (d, 1H), 4.35 (s, 2H), 1.50 (s, 9H).

Example 16A

2-Hydrazino-5-(methoxymethyl)pyridine

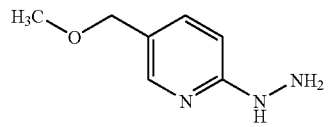

2.2 g (14.0 mmol) of the compound from Example 12A are initially charged in 10 ml of ethanol. 7.0 g (140.0 mmol) of hydrazine hydrate are added, and the mixture is stirred under reflux for 16 h. The reaction mixture is then reacted again in a single-mode microwave oven (CEM Explorer) at 150° C. for 2 h. The mixture is then concentrated on a rotary evaporator, taken up in ethyl acetate, washed once with saturated sodium bicarbonate solution, dried over magnesium sulfate and concentrated again, and the residue is dried under high vacuum.

Yield: 970 mg (45% of theory)

LC-MS (Method 7): $R_t$=0.20 min; MS (ESIpos): m/z=154 [M+H]$^+$;

¹H-NMR (400 MHz, CDCl₃): δ=8.09 (d, 1H), 7.50 (dd, 1H), 6.70 (d, 1H), 6.00 (br. s, 1H), 4.32 (s, 2H), 3.75 (br. s, 2H), 3.35 (s, 3H).

Example 17A 5-(tert-Butoxymethyl)-2-hydrazinopyridine

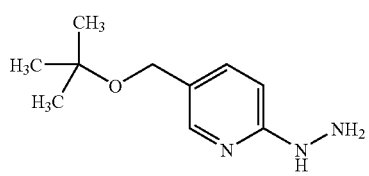

7.9 g (40.0 mmol) of the compound from Example 13A are dissolved in 45 ml of ethanol. The solution is divided into three reaction vessels, and in each case 6.6 g (131.9 mmol) of hydrazine hydrate are added. Each reaction mixture is reacted in each case for 4 h at 170° C. in a single-mode microwave oven (CEM Explorer). The three mixtures are then combined, and the solvent is removed. The residue is taken up in ethyl acetate and washed once with saturated sodium bicarbonate solution. The aqueous phase is reextracted once with ethyl acetate. The two ethyl acetate phases are combined and washed once with saturated sodium chloride solution. The mixture is dried over magnesium sulfate and the solvent is removed. The residue is triturated with petroleum ether, and the solid obtained is filtered off and dried under high vacuum.

Yield: 1.6 g (21% of theory)

LC-MS (Method 5): $R_t$=0.77 min; MS (ESIpos): m/z=196 [M+H]⁺;

¹H-NMR (400 MHz, CDCl₃): δ=8.09 (d, 1H), 7.50 (d, 1H), 6.68 (d, 1H), 5.75 (br. s, 1H), 4.32 (s, 2H), 3.85 (br. s, 2H), 1.28 (s, 9H).

Example 18A (4-Chloro-6-hydrazinopyridin-3-yl)methanol

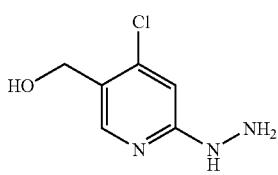 [SMILES: NNc1cc(Cl)c(CO)cn1]

500 mg (2.8 mmol) of (4,6-dichloropyridin-3-yl)methanol are initially charged in 2 ml of ethanol. 7.3 mg (14.0 mmol) of hydrazine hydrate are added, and the mixture is stirred at 100° C. for 20 h. The mixture is then allowed to cool to RT, the solid formed is filtered off and discarded and the mother liquor is concentrated on a rotary evaporator, which gives the title compound as a mixture with about 10% [4,6-bis(hydrazino)pyridin-3-yl]methanol.

Yield: 450 mg (92% of theory)

LC-MS (Method 6): $R_t$=0.25 min; MS (ESIpos): m/z=174 [M+H]⁺;

¹H-NMR (400 MHz, DMSO-d₆): δ=7.75 (s, 1H), 7.41 (s, 1H), 6.90 (s, 1H), 5.20 (br. s, 1H), 4.35 (br. s, 2H).

Example 19A 5-(2,2-Dimethylpropoxy)-2-hydrazinopyridine

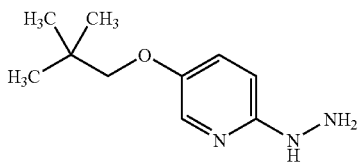

Step a): 2-Chloro-5-(2,2-dimethylpropoxy)pyridine

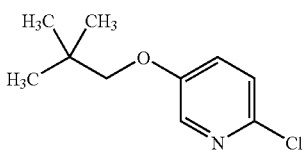

5.2 g (40.0 mmol) of 6-chloropyridin-3-ol, 11.9 g (60.0 mmol) of 1-iodo-2,2-dimethylpropane, 19.6 g (60.0 mmol) of cesium carbonate and 120 ml of diethylene glycol dimethyl ether are divided into five portions of equal size and reacted portion-wise in a single-mode microwave oven (CEM Explorer) at 160° C. for 4 h. The five reaction mixtures obtained are then combined, the solid is filtered off and washed with diethylene glycol dimethyl ether and filtrate and wash solutions are combined. Most of the solvent is removed, and 300 ml of water are added to the concentrated (about 50 ml) solution. The mixture is stirred for 30 min, and the solid obtained is filtered off, washed once with water and dried under high vacuum.

Yield: 7.0 g (88% of theory)

LC-MS (Method 6): $R_t$=2.47 min; MS (ESIpos): m/z=200 [M+H]⁺;

¹H-NMR (400 MHz, CDCl₃): δ=8.05 (d, 1H), 7.25-7.15 (m, 2H), 3.61 (s, 2H), 1.03 (s, 9H).

Step b):
5-(2,2-Dimethylpropoxy)-2-hydrazinopyridine

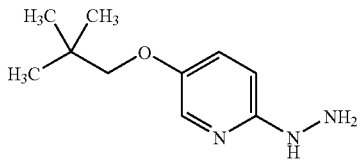

6.2 g (30.8 mmol) of 2-chloro-5-(2,2-dimethylpropoxy)pyridine together with 60 ml (1.2 mol) of hydrazine hydrate are divided into four portions of equal size, and in each case 10 ml of ethanol are added. Each portion is reacted in a single-mode microwave oven (CEM Explorer) at 170° C. (200 Watt) for in each case 12 h. The four mixtures are then combined, and the solvent is removed. The residue is taken up in ethyl acetate and washed in each case once with saturated sodium bicarbonate solution and saturated sodium chloride solution. The mixture is dried over magnesium sulfate and the solvent is removed under reduced pressure.

Yield: 6.0 g (76% of theory)

LC-MS (Method 6): $R_t$=1.28 min; MS (ESIpos): m/z=196 [M+H]$^+$;

$^1$H-NMR (400 MHz, CDCl$_3$): δ=7.84 (s, 1H), 7.17 (dd, 1H), 6.68 (d, 1H), 5.54 (br. s, 1H), 3.80 (br. s, 2H), 3.56 (s, 2H), 1.02 (s, 9H).

Example 20A

2-Bromo-4,5-dimethylpyridine

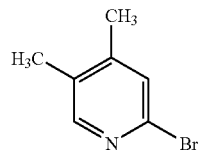

71.3 g (0.8 mol) of 2-(dimethylamino)ethanol are initially charged in 500 ml of n-hexane, and the mixture is cooled to 0° C. 1.0 liter (1.6 mol) of n-butyllithium solution (1.6 M in n-hexane) is added slowly, and the mixture is stirred at 0° C. for 15 min. A solution of 17.9 g (166.7 mmol) of 3,4-lutidine in 500 ml of n-hexane is then added dropwise, and the mixture is stirred at 0° C. for 1 h. The mixture is then cooled to −78° C., and a solution of 331.7 g (1.0 mol) of carbon tetrabromide in 1.0 liter of THF is added. The reaction mixture is stirred at −78° C. for 1 h and then allowed to warm to RT. The mixture is cooled again to 0° C., and 1.5 liters of water are slowly added dropwise. The phases are separated, and the organic phase is washed with water, dried over magnesium sulfate and concentrated under reduced pressure. The residue is initially prepurified on about 1 kg of silica gel (mobile phase: cyclohexane/ethyl acetate 9:1, then 7:3). The product-containing fractions are combined and concentrated under reduced pressure. The residue is then purified again on silica gel (mobile phase: cyclohexane/ethyl acetate 9:1). The product obtained in this manner contains about 10% of the regioisomeric 2-bromo-3,4-dimethylpyridine.

Yield: 6.7 g (20% of theory)

GC-MS (Method 11): $R_t$=4.24 min; MS (ESIpos): m/z=187 [M+H]$^+$;

$^1$H-NMR (400 MHz, CDCl$_3$): δ=8.07 (s, 1H), 7.25 (s, 1H), 2.24 (s, 3H), 2.18 (s, 3H).

Example 21A

2-Hydrazino-4,5-dimethylpyridine

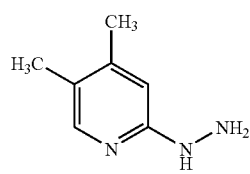

3.8 g (18.4 mmol, purity 90%) of the compound from Example 20A are initially charged in 12.5 ml of ethanol. 8.9 ml (9.2 g, 183.8 mmol) of hydrazine hydrate are added, and the mixture is reacted in a single-mode microwave oven (CEM Explorer) at 170° C. (100 Watt) for 2 h. The reaction solution is then concentrated, and the residue is taken up in ethyl acetate and washed in each case once with saturated sodium bicarbonate solution and saturated sodium chloride solution. The organic phase is dried over sodium sulfate, filtered and concentrated under reduced pressure.

Yield: 2.2 g (86% of theory)

LC-MS (Method 6): $R_t$=0.75 min; MS (ESIpos): m/z=138 [M+H]$^+$;

$^1$H-NMR (400 MHz, CDCl$_3$): δ=7.86 (s, 1H), 6.51 (s, 1H), 5.61 (br. s, 1H), 3.72 (br. s, 2H), 2.20 (s, 3H), 2.12 (s, 3H).

EXEMPLARY EXAMPLES

Example 1

1-(3-Methylcyclohexyl)-3-{[2-(5-oxo-4-pyridin-3-yl-2,5-dihydro-1H-pyrazol-1-yl)pyridin-4-yl]-methyl}urea

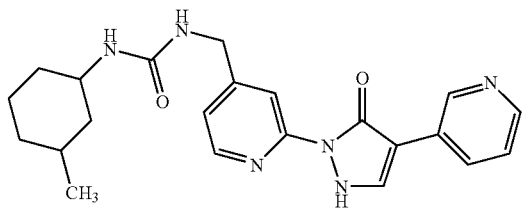 [SMILES: CC1CCCC(NC(=O)NCc2ccnc(-n3[nH]cc(-c4cccnc4)c3=O)c2)C1]

13.9 mg (100 μmol) of 3-methylcyclohexyl isocyanate are initially charged, 34.0 mg (100 mol) of the compound from Example 4A, dissolved in 0.6 ml of 1,2-dichloroethane, and 25.8 mg (200 μmol) of diisopropylethylamine are added and the mixture is stirred at RT overnight. The mixture is then concentrated, the residue is taken up in DMSO, the precipitate is filtered off and the filtrate is purified by preparative HPLC (Method 3).

Yield: 5.7 mg (14% of theory)

LC-MS (Method 3): $R_t$=1.40 min; MS (ESIpos): m/z=407 [M+H]$^+$.

Example 2

Methyl N-({[2-(5-oxo-4-pyridin-3-yl-2,5-dihydro-1H-pyrazol-1-yl)pyridin-4-yl]methyl}carbamoyl)-L-valinate

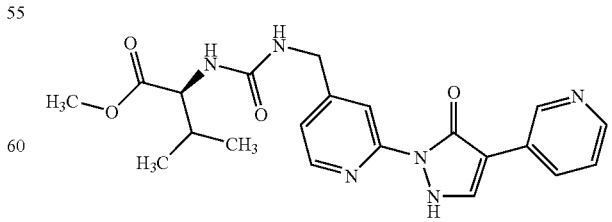

The title compound is obtained analogously to Example 1 starting with Example 4A and the appropriate isocyanate.

Yield: 7% of theory

LC-MS (Method 3): $R_t$=1.22 min; MS (ESIpos): m/z=425 [M+H]⁺.

Example 3

2-(4-{[(Cyclohexylmethyl)amino]methyl}pyridin-2-yl)-4-pyridin-3-yl-1,2-dihydro-3H-pyrazol-3-one

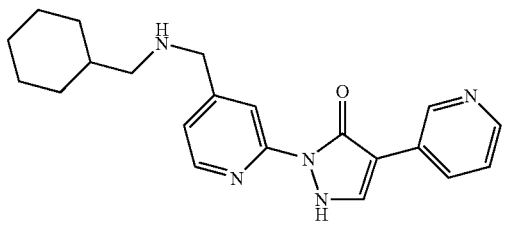 [SMILES: O=c1c(-c2cccnc2)c[nH]n1-c1cc(CNCC2CCCCC2)ccn1]

11.2 mg (100 µmol) of cyclohexanecarbaldehyde are initially charged, 34.0 mg (100 mol) of the compound from Example 4A, dissolved in 0.6 ml of ethanol, and 25.8 mg (200 µmol) of diisopropylethylamine are added and the mixture is stirred at RT overnight. 5.7 mg (150 µmol) of sodium borohydride are then added, and the mixture is shaken at RT for 3 h. 100 µl of water are then added, and the mixture is concentrated. The residue is taken up in DMSO, the precipitate is filtered off and the filtrate is purified by preparative HPLC (Method 4).

Yield: 2.6 mg (7% of theory)

LC-MS (Method 4): $R_t$=1.30 min; MS (ESIpos): m/z=364 [M+H]⁺.

Example 4

2-{5-[(Methylamino)methyl]pyridin-2-yl}-4-pyridin-3-yl-1,2-dihydro-3H-pyrazol-3-one hydrochloride

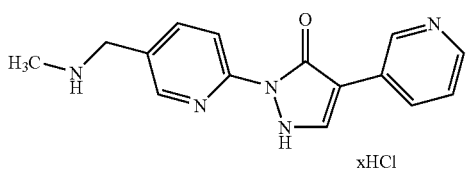 [SMILES: CNCc1ccc(-n2[nH]cc(-c3cccnc3)c2=O)nc1]

300 mg (1.4 mmol) of the compound from Example 2A and 207 mg (1.4 mmol) of the compound from Example 5A are dissolved in 2 ml of ethanol, and 47 mg (0.3 mmol) of p-toluenesulfonic acid are added. The mixture is heated under reflux for 24 h, then cooled to RT and purified directly by preparative HPLC (RP18 column; mobile phase: acetonitrile/water gradient with 0.1% formic acid added to the water). The product-containing fractions are concentrated under reduced pressure, the residue is dissolved in 1.5 ml of ethanol and 0.5 ml of a 4 N solution of hydrogen chloride in dioxane is added. The mixture is stirred at RT for 30 min and then concentrated under reduced pressure, and the residue is dried under high vacuum.

Yield: 25 mg (5% of theory)

LC-MS (Method 1): $R_t$=1.68 min; MS (ESIpos): m/z=282 [M+H]⁺;

¹H-NMR (400 MHz, DMSO-d₆): δ=9.39-9.35 (m, 1H), 8.90 (d, 1H), 8.81 (s, 1H), 8.67 (s, 1H), 8.62 (d, 1H), 8.47 (d, 1H), 8.20 (d, 1H), 7.94 (dd, 1H), 4.23-4.19 (m, 2H), 2.59-2.56 (m, 3H).

Example 5

2-(5-{[(2-Methoxyethyl)amino]methyl}pyridin-2-yl)-4-pyridin-3-yl-1,2-dihydro-3H-pyrazol-3-one hydrochloride

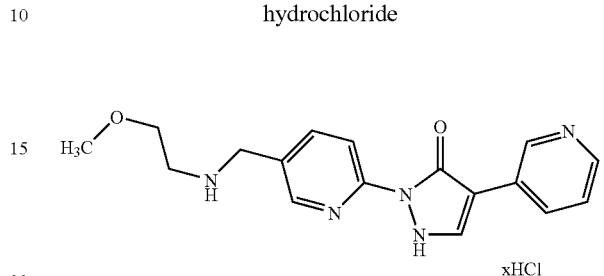

200 mg (0.9 mmol) of the compound from Example 2A and 178 mg (0.9 mmol) of the compound from Example 6A are dissolved in 2 ml of ethanol, and 42 mg (0.2 mmol) of p-toluenesulfonic acid are added. The mixture is heated under reflux for 24 h and then cooled to RT and purified directly by preparative HPLC (RP18 column; mobile phase: acetonitrile/water gradient with 0.1% formic acid added to the water). The product-containing fractions are concentrated under reduced pressure, the residue is dissolved in 1 ml of ethanol and 0.5 ml of a 4 N solution of hydrogen chloride in dioxane is added. The mixture is stirred at RT for 30 min and then concentrated under reduced pressure, and the residue is dried under high vacuum.

Yield: 10 mg (3% of theory)

HPLC (Method 10): $R_t$=2.84 min; MS (ESIpos): m/z=326 [M+H]⁺;

¹H-NMR (400 MHz, DMSO-d₆): δ=9.47 (br. s, NH), 9.40 (s, 1H), 8.96 (d, 1H), 8.84 (s, 1H), 8.67 (s, 1H), 8.65 (d, 1H), 8.47 (d, 1H), 8.24 (d, 1H), 8.00 (dd, 1H), 4.26-4.22 (m, 2H), 3.66-3.62 (m, 2H), 3.31 (s, 3H), 3.15-3.11 (m, 2H).

Example 6

2-[5-(Methylsulfonyl)pyridin-2-yl]-4-pyridin-3-yl-1,2-dihydro-3H-pyrazol-3-one hydrochloride

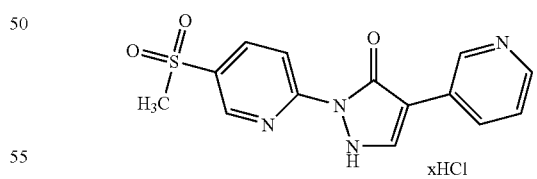

200 mg (0.9 mmol) of the compound from Example 2A and 170 mg (0.9 mmol) of the compound from Example 6A are dissolved in 2 ml of ethanol, and 3 mg (0.2 mmol) of p-toluenesulfonic acid are added. The mixture is heated under reflux for 24 h and then cooled to RT and purified directly by preparative HPLC (RP18 column; mobile phase: acetonitrile/water gradient with 0.1% formic acid added to the water). The product-containing fractions are concentrated under reduced pressure, the residue is dissolved in 1 ml of ethanol and 0.5 ml of a 4 N solution of hydrogen chloride in dioxane is added.

The mixture is stirred at RT for 30 min and then concentrated under reduced pressure, and the residue is dried under high vacuum.

Yield: 224 mg (66% of theory)

LC-MS (Method 1): $R_t$=2.12 min; MS (ESIpos): m/z=317 [M+H]$^+$;

$^1$H-NMR (400 MHz, DMSO-d$_6$): δ=9.41 (s, 1H), 8.99 (s, 1H), 8.98-8.94 (m, 2H), 8.71 (d, 1H), 8.66 (d, 1H), 8.53 (dd, 1H), 8.01 (dd, 1H), 3.37 (s, 3H).

Example 7

4-(5-Bromopyridin-3-yl)-2-(4-methylpyridin-2-yl)-1,2-dihydro-3H-pyrazol-3-one hydrochloride

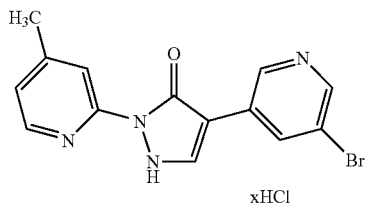 [SMILES: Cc1ccnc(-n2[nH]cc(-c3cncc(Br)c3)c2=O)c1]

1070 mg (3.6 mmol) of the compound from Example 9A and 441 mg (3.6 mmol) of the compound from Example 10A are dissolved in 10 ml of ethanol, and 123 mg (0.7 mmol) of p-toluenesulfonic acid are added. The mixture is heated under reflux for 24 h and then cooled to RT, and the supernatant is decanted off. The residue is dissolved in 10 ml of ethanol, and 1 ml of a 4 N solution of hydrogen chloride in dioxane is added. The mixture is stirred at RT for 30 min and then concentrated under reduced pressure, and the residue is dried under high vacuum.

Yield: 470 mg (36% of theory)

LC-MS (Method 6): $R_t$=1.99 min; MS (ESIpos): m/z=332 [M+H]$^+$;

$^1$H-NMR (400 MHz, DMSO-d$_6$): δ=9.12 (s, 1H), 8.66-8.62 (m, 1H), 8.53 (s, 1H), 8.51 (d, 1H), 8.35 (d, 1H), 8.16 (d, 1H), 7.24 (d, 1H), 2.46 (s, 3H).

Example 8

5-[2-(4-Methylpyridin-2-yl)-3-oxo-2,3-dihydro-1H-pyrazol-4-yl]pyridine-3-carbonitrile hydrochloride

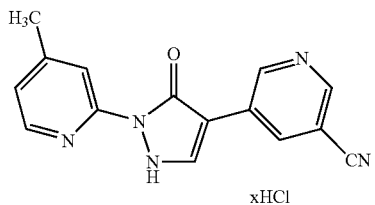 [SMILES: Cc1ccnc(-n2[nH]cc(-c3cncc(C#N)c3)c2=O)c1]

200 mg (0.5 mmol) of the compound from Example 7, 47 mg (0.4 mmol) of zinc cyanide and 19 mg (0.02 mmol) of tetrakis(triphenylphosphine)palladium(0) are reacted in 3 ml of DMF at 220° C. in a single-mode microwave oven (Emrys Optimizer) for 50 min. The reaction mixture is then concentrated under reduced pressure, the residue is taken up in 2 ml of ethanol and the mixture is adjusted with 1 N aqueous sodium hydroxide solution to pH 10. The mixture is extracted with ethyl acetate, the organic phase is dried over sodium sulfate and concentrated under reduced pressure and the residue is purified by preparative HPLC (RP18 column; mobile phase: acetonitrile/water gradient with 0.1% formic acid added to the water). The product-containing fractions are concentrated under reduced pressure, the residue is dissolved in 1 ml of ethanol and 0.5 ml of a 4 N solution of hydrogen chloride in dioxane is added. The mixture is stirred at RT for min and then concentrated under reduced pressure, and the residue is dried under high vacuum.

Yield: 12 mg (7% of theory)

LC-MS (Method 6): $R_t$=1.79 min; MS (ESIpos): m/z=278 [M+H]$^+$;

$^1$H-NMR (400 MHz, DMSO-d$_6$): δ=9.38 (s, 1H), 8.76 (s, 1H), 8.71 (s, 1H), 8.55 (s, 1H), 8.35 (d, 1H), 8.16 (d, 1H), 7.24 (d, 1H), 2.46 (s, 3H).

Example 9 tert-Butyl 6-[4-(5-bromopyridin-3-yl)-5-oxo-2,5-dihydro-1H-pyrazol-1-yl]pyridine-3-carboxylate hydrochloride

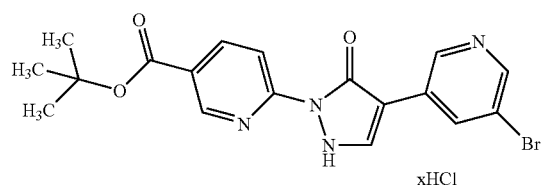 [SMILES: CC(C)(C)OC(=O)c1ccc(-n2[nH]cc(-c3cncc(Br)c3)c2=O)nc1]

500 mg (1.7 mmol) of the compound from Example 9A and 350 mg (1.7 mmol) of the compound from Example 15A are dissolved in 2 ml of ethanol, and 58 mg (0.3 mmol) of p-toluenesulfonic acid are added. The mixture is heated under reflux for 24 h and then cooled to RT, and 0.5 ml of a 4 N solution of hydrogen chloride in dioxane is added. The mixture is stirred at RT for 30 min. The precipitate is filtered off, washed with ethanol and diethyl ether and dried under high vacuum.

Yield: 425 mg (56% of theory)

LC-MS (Method 5): $R_t$=1.47 min; MS (ESIpos): m/z=417 [M+H]$^+$;

$^1$H-NMR (400 MHz, DMSO-d$_6$): δ=9.15 (s, 1H), 8.91 (s, 1H), 8.74 (d, 1H), 8.64 (d, 1H), 8.52-8.49 (m, 2H), 8.43 (d, 1H), 1.58 (s, 9H).

Example 10

6-[4-(5-Bromopyridin-3-yl)-5-oxo-2,5-dihydro-H-pyrazol-1-yl]pyridine-3-carboxylic acid hydrochloride

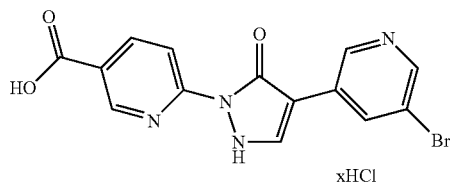 [SMILES: O=C(O)c1ccc(-n2[nH]cc(-c3cncc(Br)c3)c2=O)nc1]

60 mg (0.1 mmol) of the compound from Example 9 are suspended in 2 ml of dichloromethane, and 0.5 ml of TFA is added. The mixture is stirred at RT for 4 h and then concentrated under reduced pressure, and 0.5 ml of a 4 N solution of hydrogen chloride in dioxane is added to the residue. The mixture is stirred at RT for 30 min. The precipitate is filtered off, washed with diethyl ether and dried under high vacuum.

Yield: 37 mg (70% of theory)

LC-MS (Method 6): $R_t$=1.83 min; MS (ESIpos): m/z=361 [M+H]$^+$;

$^1$H-NMR (400 MHz, DMSO-d$_6$): δ=9.16 (s, 1H), 8.97 (s, 1H), 8.75 (d, 1H), 8.66 (d, 1H), 8.52-8.47 (m, 2H), 8.46 (d, 1H).

Example 11

2-(5-Methylpyridin-2-yl)-4-pyridin-3-yl-1,2-dihydro-3H-pyrazol-3-one hydrochloride

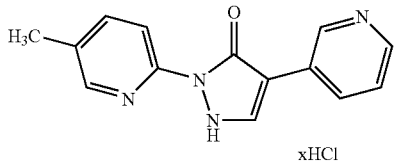 [SMILES: Cc1ccc(-n2[nH]cc(-c3cccnc3)c2=O)nc1]

100 mg (0.5 mmol) of the compound from Example 9A and 62 mg (0.5 mmol) of the compound from Example 11A are dissolved in 1.5 ml of ethanol, and 16 mg (0.1 mmol) of p-toluenesulfonic acid are added. The mixture is heated under reflux for 24 h and then cooled to RT and concentrated under reduced pressure. The residue is taken up in 2 ml of ethanol, and 1 ml of a 4 N solution of hydrogen chloride in dioxane is added. The mixture is stirred at RT for 30 min. The precipitate is filtered of, washed with ethanol and diethyl ether and dried under high vacuum.

Yield: 66 mg (50% of theory)

LC-MS (Method 6): $R_t$=1.07 min; MS (ESIpos): m/z=253 [M+H]$^+$;

$^1$H-NMR (400 MHz, DMSO-d$_6$): δ=9.31 (s, 1H), 8.82 (d, 1H), 8.64 (s, 1H), 8.57 (d, 1H), 8.34 (d, 1H), 8.27 (d, 1H), 7.93 (dd, 1H), 7.89 (dd, 1H), 2.36 (s, 3H).

Example 12

6-(5-Oxo-4-pyridin-3-yl-2,5-dihydro-1H-pyrazol-1-yl)pyridine-3-carbonitrile hydrochloride

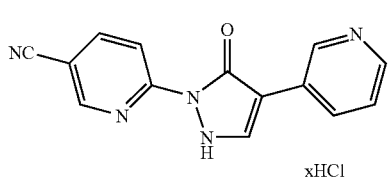

11.8 g (53.7 mmol) of the compound from Example 2A and 7.2 g (53.7 mmol) of the compound from Example 14A are initially charged in 175 ml of ethanol. 2.0 g (10.7 mmol) of p-toluene-sulfonic acid monohydrate are added, and the mixture is stirred under reflux for 16 h. The mixture is then cooled to 0° C., and the solid formed is filtered off and dried under high vacuum. The solid is stirred in a 4 N solution of hydrogen chloride in dioxane for 30 min, and the precipitate is filtered off again and dried under high vacuum.

Yield: 10.8 g (67% of theory)

LC-MS (Method 1): $R_t$=2.22 min; MS (ESIpos): m/z=264 [M+H]$^+$;

$^1$H-NMR (400 MHz, DMSO-d$_6$): δ=9.40 (s, 1H), 9.02-8.96 (m, 3H), 8.68-8.61 (m, 2H), 8.49 (dd, 1H), 8.00 (dd, 1H).

Example 13

2-[5-(Aminomethyl)pyridin-2-yl]-4-pyridin-3-yl-1,2-dihydro-3H-pyrazol-3-one dihydrochloride

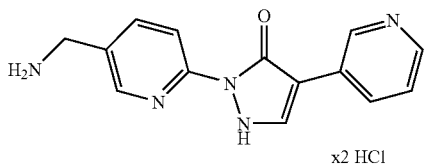 [SMILES: NCc1ccc(-n2[nH]cc(-c3cccnc3)c2=O)nc1]

10.0 g (38.0 mmol) of the compound from Example 12 are initially charged in 300 ml of acetic acid. 20 ml of a 4 N solution of hydrogen chloride in dioxane and 5.0 g (4.7 mmol) of palladium on carbon (10%) are added and the mixture is hydrogenated at RT under atmospheric pressure for 96 h. Water is then added until the organic solid formed has gone back into solution, and the catalyst is filtered off through silica gel. The filtrate is concentrated and the residue is purified by column chromatography on silica gel (mobile phase: cyclohexane/ethyl acetate mixture). The product obtained is then stirred in a 4 N solution of hydrogen chloride in dioxane for 30 min, and the solid is filtered off and dried under high vacuum. The solid is then dissolved in about 300 ml of water, and the solution is lyophilized.

Yield: 8.7 g (67% of theory)

LC-MS (Method 6): $R_t$=0.71 min; MS (ESIpos): m/z=268 [M+H]$^+$;

$^1$H-NMR (400 MHz, DMSO-d$_6$): δ=9.42 (s, 1H), 9.04 (d, 1H), 8.87 (s, 1H), 8.68-8.53 (m, 4H), 8.45 (d, 1H), 8.20 (d, 1H), 8.05 (dd, 1H), 4.12 (d, 2H).

Example 14

2,2-Dimethyl-N-{[6-(5-oxo-4-pyridin-3-yl-2,5-dihydro-1H-pyrazol-1-yl)pyridin-3-yl]methyl}-propanamide hydrochloride

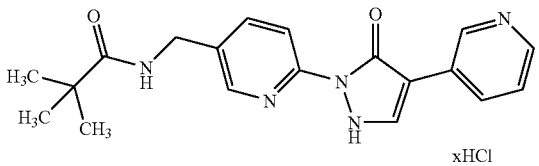 [SMILES: CC(C)(C)C(=O)NCc1ccc(-n2[nH]cc(-c3cccnc3)c2=O)nc1]

100 mg (0.3 mmol) of the compound from Example 13 are suspended in 3 ml of dichloromethane. 152 mg (1.2 mmol) of N,N-diisopropylethylamine (Hünig base) are added, and the mixture is stirred at RT for 5 min. 43 mg (0.4 mmol) of 2,2-dimethylpropanoyl chloride are then added, and the mixture is stirred at RT for 16 h. The mixture is then concentrated on a rotary evaporator, the residue is taken up in 5 ml of dioxane and 1 ml 1 N aqueous sodium hydroxide solution is added. This mixture is then purified by preparativer HPLC (RP18 column; mobile phase: acetonitrile/water gradient with addition of 0.1% TFA to the water). The product-containing fractions are combined and concentrated on a rotary evaporator. The residue is dissolved in 1 N hydrochloric acid, and the solution is lyophilized. The solid is then stirred in tert-butyl methyl ether for 30 min, filtered off and dried under high vacuum.

Yield: 71 mg (62% of theory)

LC-MS (Method 1): $R_t$=2.37 min; MS (ESIpos): m/z=352 [M+H]$^+$;

$^1$H-NMR (400 MHz, DMSO-$d_6$): δ=9.39 (s, 1H), 9.00 (d, 1H), 8.87 (s, 1H), 8.63 (d, 1H), 8.33 (m, 2H), 8.27 (t, 1H), 8.05 (dd, 1H), 7.93 (dd, 1H), 4.33 (d, 2H), 1.12 (s, 9H).

Example 15 tert-Butyl 6-(5-oxo-4-pyridin-3-yl-2,5-dihydro-1H-pyrazol-1-yl)pyridine-3-carboxylate

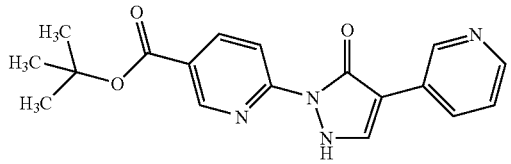 [SMILES: CC(C)(C)OC(=O)c1ccc(-n2[nH]cc(-c3cccnc3)c2=O)nc1]

2.2 g (10.0 mmol) of the compound from Example 2A are initially charged in 50 ml of ethanol. 2.1 g (10.0 mmol) of the compound from Example 15A and 380 mg (2.0 mmol) of p-toluenesulfonic acid are added, and the mixture is stirred under reflux for 16 h. The mixture is then cooled to 0° C., and the solid formed is filtered off and washed once with a little ethanol (batch 1). The mother liquor is concentrated and the residue is triturated with a little ethanol. The solid obtained is filtered off and washed once with ethanol (batch 2). The two solids batches are combined and dried under high vacuum. The solid is then stirred in tert-butyl methyl ether for 30 min, filtered off again and dried under high vacuum.

Yield: 2.7 g (79% of theory)

LC-MS (Method 5): $R_t$=0.93 min; MS (ESIpos): m/z=339 [M+H]$^+$;

$^1$H-NMR (400 MHz, DMSO-$d_6$): δ=9.11 (d, 1H), 8.91 (d, 1H), 8.57 (s, 1H), 8.51-8.49 (m, 1H), 8.40 (dd, 1H), 8.37-8.35 (m, 1H), 8.28 (d, 1H), 7.37 (dd, 1H), 1.58 (s, 9H).

Example 16 tert-Butyl 6-(5-oxo-4-pyridin-3-yl-2,5-dihydro-1H-pyrazol-1-yl)pyridine-3-carboxylate hydrochloride

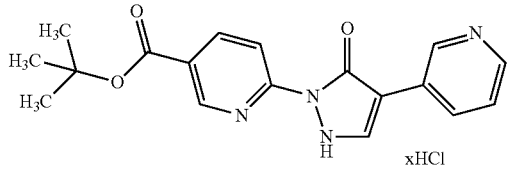 [SMILES: CC(C)(C)OC(=O)c1ccc(-n2[nH]cc(-c3cccnc3)c2=O)nc1]

100 mg (0.3 mmol) of the compound from Example 15 are stirred in a 4 N solution of hydrogen chloride in dioxane at RT for 30 min. The solid is then filtered off and dried under high vacuum.

Yield: 90 mg (81% of theory)

LC-MS (Method 1): $R_t$=3.04 min; MS (ESIpos): m/z=339 [M+H]$^+$;

$^1$H-NMR (400 MHz, DMSO-$d_6$): δ=9.39 (s, 1H), 8.99-8.86 (m, 3H), 8.65 (d, 1H), 8.55 (d, 1H), 8.45 (d, 1H), 8.00 (dd, 1H), 1.57 (s, 9H).

Example 17

6-(5-Oxo-4-pyridin-3-yl-2,5-dihydro-1H-pyrazol-1-yl)pyridine-3-carboxamide hydrochloride

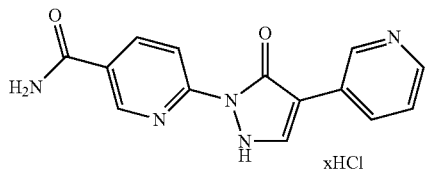 [SMILES: NC(=O)c1ccc(-n2[nH]cc(-c3cccnc3)c2=O)nc1]

Step a 6-(5-Oxo-4-pyridin-3-yl-2,5-dihydro-1H-pyrazol-1-yl)pyridine-3-carbonyl chloride

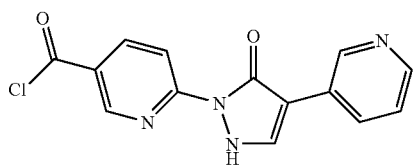 [SMILES: O=C(Cl)c1ccc(-n2[nH]cc(-c3cccnc3)c2=O)nc1]

2.5 g (8.9 mmol) of 6-(5-oxo-4-pyridin-3-yl-2,5-dihydro-1H-pyrazol-1-yl)pyridine-3-carboxylic acid [WO 2006/114213, Example 39] are initially charged in 50 ml of dichloromethane. With stirring, 0.1 ml of DMF and then slowly 2.2 g (17.7 mmol) of oxalyl chloride are added at RT. After the evolution of gas has ceased, the mixture is stirred under reflux for 1 h. The mixture is then concentrated on a rotary evaporator, the residue is dried under high vacuum and the acid chloride obtained in this manner is used directly for the subsequent step.

Step b 6-(5-Oxo-4-pyridin-3-yl-2,5-dihydro-1H-pyrazol-1-yl)pyridine-3-carboxamide hydrochloride

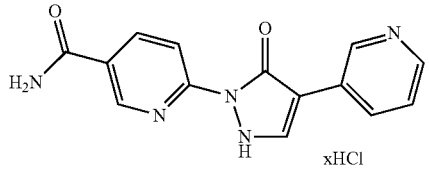 [SMILES: NC(=O)c1ccc(-n2[nH]cc(-c3cccnc3)c2=O)nc1]

337 mg (1.0 mmol) of 6-(5-oxo-4-pyridin-3-yl-2,5-dihydro-1H-pyrazol-1-yl)pyridine-3-carbonyl chloride are suspended in 5 ml of dioxane. Slowly and with stirring, 4 ml of a 5 N solution of ammonia in dioxane are then added, and the mixture is stirred at RT for 16 h. The mixture is then concentrated, and the residue is taken up in DMSO and purified by preparative HPLC (RP18 column; mobile phase: acetonitrile/water gradient with 0.1% TFA added to the water). The product-containing fractions are combined and concentrated on a rotary evaporator. The residue is dissolved in 1 N hydrochloric acid, and the solution is then lyophilized.

Yield: 47 mg (15% of theory)

LC-MS (Method 1): $R_t$=2.01 min; MS (ESIpos): m/z=282 [M+H]$^+$;

$^1$H-NMR (400 MHz, DMSO-d$_6$): δ=9.41 (s, 1H), 9.00-8.95 (m, 2H), 8.48 (s, 1H), 8.65 (d, 1H), 8.56-8.42 (m, 2H), 8.23 (s, 1H), 8.03 (t, 1H), 7.63 (s, 1H).

Example 18

N-tert-Butyl-6-(5-oxo-4-pyridin-3-yl-2,5-dihydro-1H-pyrazol-1-yl)pyridine-3-carboxamide hydrochloride

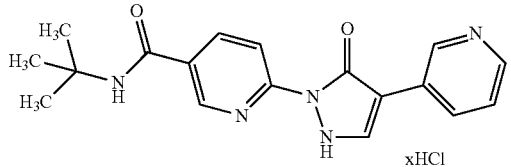 [SMILES: CC(C)(C)NC(=O)c1ccc(-n2[nH]cc(-c3cccnc3)c2=O)nc1]

337 mg (1.0 mmol) of 6-(5-oxo-4-pyridin-3-yl-2,5-dihydro-1H-pyrazol-1-yl)pyridin-3-carbonyl chloride from Example 17 (Step a) are initially charged, a solution of 293 mg (4.0 mmol) of tert-butylamine in 15 ml of THF is added and the mixture is stirred at RT for 1 h. The mixture is then concentrated on a rotary evaporator, and the residue is purified by preparative HPLC (RP18 column; mobile phase: acetonitrile/water gradient with 0.1% TFA added to the water). The product-containing fractions are combined and concentrated. The residue is dissolved in 1 N hydrochloric acid, and the solution is then lyophilized.

Yield: 47 mg (12% of theory)

LC-MS (Method 1): $R_t$=2.50 min; MS (ESIpos): m/z=338 [M+H]$^+$;

$^1$H-NMR (400 MHz, DMSO-d$_6$): δ=9.41 (s, 1H), 8.99 (d, 1H), 8.88 (s, 2H), 8.64 (d, 1H), 8.51-8.39 (m, 2H), 8.09 (s, 1H), 8.03 (t, 1H), 1.40 (s, 9H).

Example 19

2-[5-(Methoxymethyl)pyridin-2-yl]-4-pyridin-3-yl-1,2-dihydro-3H-pyrazol-3-one hydrochloride

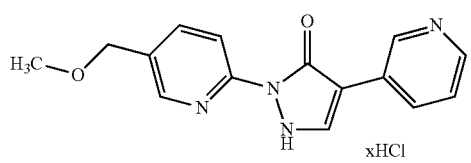 [SMILES: COCc1ccc(-n2[nH]cc(-c3cccnc3)c2=O)nc1]

661 mg (3.0 mmol) of the compound from Example 2A and 460 mg (3.0 mmol) of the compound from Example 16A are initially charged in 10 ml of ethanol. 114 mg (0.6 mmol) of p-toluenesulfonic acid are added, and the mixture is stirred under reflux for 16 h. The mixture is allowed to cool to RT, and the solid formed is filtered off and washed once with ethanol (batch 1). The mother liquor is concentrated and the residue is purified by preparative HPLC (RP18 column; mobile phase: acetonitrile/water gradient with 0.1% TFA added to the water) (batch 2). Both batches are combined and dissolved in 1 N hydrochloric acid, and the solution is then lyophilized.

Yield: 625 mg (65% of theory)

LC-MS (Method 7): $R_t$=1.08 min; MS (ESIpos): m/z=283 [M+H]$^+$;

$^1$H-NMR (400 MHz, DMSO-d$_6$): δ=9.41 (s, 1H), 9.01 (d, 1H), 8.80 (s, 1H), 8.65 (d, 1H), 8.44 (d, 1H), 8.40 (d, 1H), 8.06-8.04 (m, 2H), 4.50 (s, 2H), 3.34 (s, 3H).

Example 20

2-[5-(tert-Butoxymethyl)pyridin-2-yl]-4-pyridin-3-yl-1,2-dihydro-3H-pyrazol-3-one

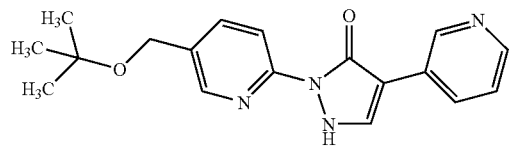 [SMILES: CC(C)(C)OCc1ccc(-n2[nH]cc(-c3cccnc3)c2=O)nc1]

661 mg (3.0 mmol) of the compound from Example 2A and 586 mg (3.0 mmol) of the compound from Example 17A are initially charged in 10 ml of ethanol. 114 mg (0.6 mmol) of p-toluenesulfonic acid are added, and the mixture is stirred under reflux for 16 h. The mixture is then allowed to cool to RT, and the solid formed is filtered off, washed once with ethanol and dried under high vacuum. The solid is then stirred in tert-butyl methyl ether for 30 min, filtered off again and dried under high vacuum (batch 1). The filtrates and wash solutions obtained beforehand are combined and concentrated, and the residue is stirred in saturated sodium bicarbonate solution. The solid obtained is filtered off and washed once with water, and the filter residue is then purified by preparative HPLC (RP18 column; mobile phase: acetonitrile/water gradient with addition of 0.1% TFA to the water). The product fractions are combined and concentrated (batch 2).

Yield: together 487 mg (50% of theory)

LC-MS (Method 5): $R_t$=0.82 min; MS (ESIpos): m/z=325 [M+H]$^+$;

$^1$H-NMR (400 MHz, DMSO-d$_6$): δ=9.08 (s, 1H), 8.41 (s, 2H), 8.37 (d, 1H), 8.24 (d, 2H), 7.98 (d, 1H), 8.38 (dd, 1H), 4.49 (s, 2H), 1.25 (s, 9H).

Example 21

2-[5-(tert-Butoxymethyl)pyridin-2-yl]-4-pyridin-3-yl-1,2-dihydro-3H-pyrazol-3-one hydrochloride

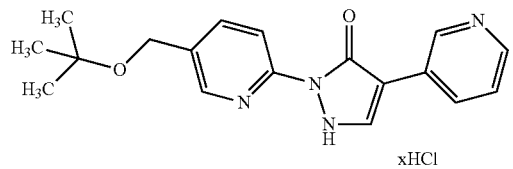 [SMILES: CC(C)(C)OCc1ccc(-n2[nH]cc(-c3cccnc3)c2=O)nc1]

400 mg (1.2 mmol) of the compound from Example 20 are stirred in 20 ml of a 4 N solution of hydrogen chloride in dioxane at RT for 30 min. The solid is filtered off and dried under high vacuum. It is then dissolved in water, and the solution is lyophilized. The lyophilizate is once more stirred with 10 ml of a 4 N solution of hydrogen chloride in dioxane for 30 min. The solid is filtered off, washed once with tert-butyl methyl ether and dried under high vacuum.

Yield: 306 mg (69% of theory)

LC-MS (Method 5): $R_t$=0.81 min; MS (ESIpos): m/z=325 [M+H]$^+$;

$^1$H-NMR (400 MHz, DMSO-d$_6$): δ=9.38 (s, 1H), 8.94 (d, 1H), 8.73 (s, 1H), 8.61 (d, 1H), 8.43 (s, 1H), 4.35 (d, 1H), 8.01-7.99 (m, 2H), 4.49 (s, 2H), 1.25 (s, 9H).

Example 22

4-Pyridin-3-yl-2-[5-(1H-pyrrol-1-ylmethyl)pyridin-2-yl]-1,2-dihydro-3H-pyrazol-3-one hydrochloride

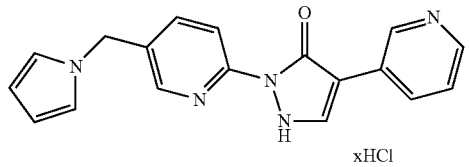 [SMILES: O=c1c(-c2cccnc2)c[nH]n1-c1ccc(Cn2cccc2)cn1]

xHCl 565 mg (9.4 mmol) of acetic acid are initially charged in 0.3 ml of water. 744 mg (9.4 mmol) of pyridine are added slowly. 191 mg (0.6 mmol) of the compound from Example 13 and 74 mg (0.6 mmol) of 2,5-dimethoxytetrahydrofuran are then added, and the mixture is stirred at 100° C. for 16 h. The mixture is then concentrated on a rotary evaporator, 3 ml of acetonitrile and 3 ml of 1 N hydrochloric acid are added and the mixture is stirred at RT for 30 min. The solid formed is filtered off, washed once with water and dried under high vacuum.

Yield: 150 mg (76% of theory)

LC-MS (Method 5): $R_t$=0.74 min; MS (ESIpos): m/z=318 [M+H]$^+$;

$^1$H-NMR (400 MHz, DMSO-d$_6$): δ=9.35 (s, 1H), 8.88 (d, 1H), 8.73 (s, 1H), 8.60 (d, 1H), 8.48 (s, 1H), 8.35 (d, 1H), 7.97-7.86 (m, 2H), 6.90 (s, 2H), 6.05 (s, 2H), 5.70 (s, 2H).

Example 23

2-[4-Chloro-5-(hydroxymethyl)pyridin-2-yl]-4-pyridin-3-yl-1,2-dihydro-3H-pyrazol-3-one trifluoroacetate

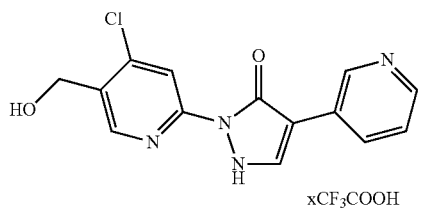 [SMILES: O=c1c(-c2cccnc2)c[nH]n1-c1cc(Cl)c(CO)cn1]

xCF$_3$COOH 345 mg (1.6 mmol) of the compound from 2A, 272 mg (1.6 mmol) of the compound from Example 18A and 60 mg (0.3 mmol) of p-toluenesulfonic acid are initially charged in a mixture of 10 ml of THF and 5 ml of ethanol. The mixture is reacted at 150° C. in a single-mode microwave oven (CEM Explorer) for 3 h. The mixture is then concentrated on a rotary evaporator, and the residue is taken up in a mixture of 5 ml of methanol and 4 ml of 1 N hydrochloric acid. The product is purified twice successively by preparative HPLC (RP18 column; mobile phase: acetonitrile/water gradient with addition of 0.1% TFA to the water).

Yield: 16 mg (2% of theory)

LC-MS (Method 6): $R_t$=1.04 min; MS (ESIpos): m/z=303 [M+H]$^+$;

$^1$H-NMR (400 MHz, DMSO-d$_6$): δ=9.38 (s, 1H), 8.64 (d, 1H), 8.48 (s, 1H), 8.33 (d, 1H), 8.20 (s, 1H), 7.96 (s, 1H), 7.77 (dd, 1H), 4.57 (s, 2H).

Example 24

2-[4-Chloro-5-(hydroxymethyl)pyridin-2-yl]-4-pyridin-3-yl-1,2-dihydro-3H-pyrazol-3-one hydrochloride

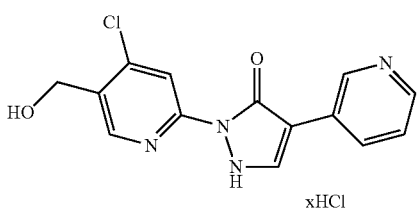 [SMILES: O=c1c(-c2cccnc2)c[nH]n1-c1cc(Cl)c(CO)cn1]

xHCl 12 mg (0.03 mmol) of the compound from Example 23 are stirred in 1.5 ml of a 4 N solution of hydrogen chloride in dioxane for 30 min. The mixture is then decanted, the residue is stirred in tert-butyl methyl ether and decanted off again, and the solid that remains is initially air-dried and then dried under high vacuum.

Yield: 10 mg (95% of theory)

LC-MS (Method 6): $R_t$=1.06 min; MS (ESIpos): m/z=303 [M+H]$^+$;

$^1$H-NMR (400 MHz, DMSO-d$_6$): δ=9.31 (s, 1H), 8.90 (d, 1H), 8.66 (s, 1H), 8.63 (d, 2H), 8.03 (dd, 1H), 7.69 (s, 1H), 4.61 (s, 2H).

Example 25

1-(2,4-Difluorophenyl)-3-{[2-(5-oxo-4-pyridin-3-yl-2,5-dihydro-1H-pyrazol-1-yl)pyridin-4-yl]-methyl}urea

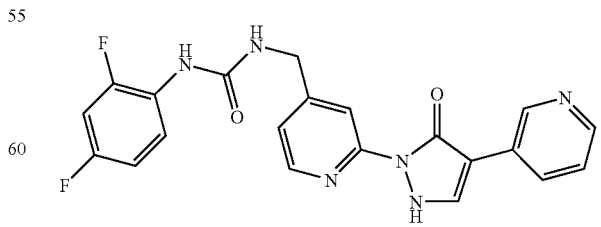

2.7 g (10 mmol) of the compound from Example 4A are dissolved in 60 ml of 1,2-dichloroethane and provided as a stock solution.

16 mg (0.1 mmol) of 2,4-difluoro-1-isocyanatobenzene are initially charged, and 600 μl (0.1 mmol) of the above stock solution and 26 mg (0.2 mmol) of N,N-diisopropylethylamine (Hünig base) are added. The reaction mixture is stirred at RT for 16 h. For work-up, the solvent is removed under reduced pressure, the residue is taken up in DMSO and filtered and the filtrate is purified directly by preparative LC-MS (Method 8). The product fractions are concentrated under reduced pressure and the residue is dried.

Yield: 3 mg (10% of theory)

LC-MS (Method 8): $R_t$=1.33 min; MS (ESIpos): m/z=423 [M+H]$^+$.

The compounds listed in Table 1 are prepared analogously to the procedure of Example 25 from 0.1 mmol of the compound from Example 4A and 0.1 mmol of the appropriate isocyanate:

TABLE 1

| Example No. | Structure | Yield (% of theory) | MS (ESI): [M + H]$^+$; LC-MS: $R_t$ (Method 8) |
|---|---|---|---|
| 26 | 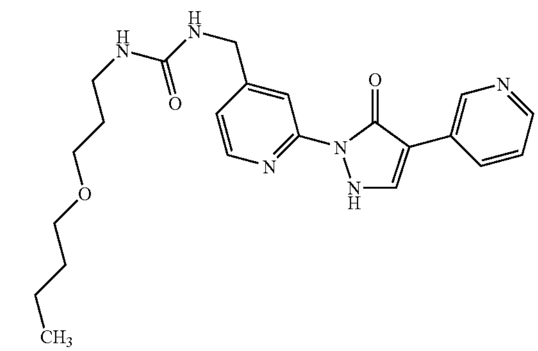 [SMILES: CCCCOCCCNC(=O)NCc1ccnc(-n2[nH]cc(-c3cccnc3)c2=O)c1] | 9% | m/z = 425; 1.32 min |
| 27 | 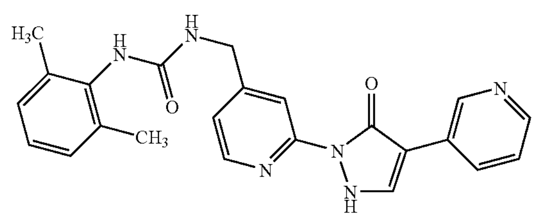 [SMILES: Cc1cccc(C)c1NC(=O)NCc1ccnc(-n2[nH]cc(-c3cccnc3)c2=O)c1] | 7% | m/z = 415; 1.31 min |
| 28 | 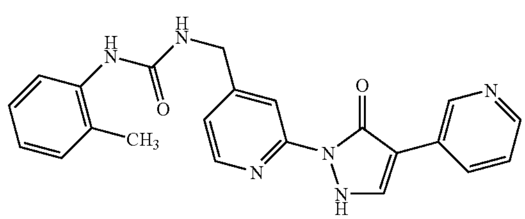 [SMILES: Cc1ccccc1NC(=O)NCc1ccnc(-n2[nH]cc(-c3cccnc3)c2=O)c1] | 11% | m/z = 401; 1.28 min |
| 29 | 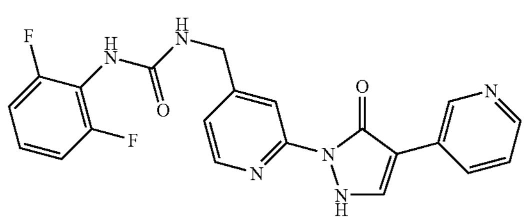 [SMILES: O=C(NCc1ccnc(-n2[nH]cc(-c3cccnc3)c2=O)c1)Nc1c(F)cccc1F] | 10% | m/z = 423; 1.20 min |
| 30 | 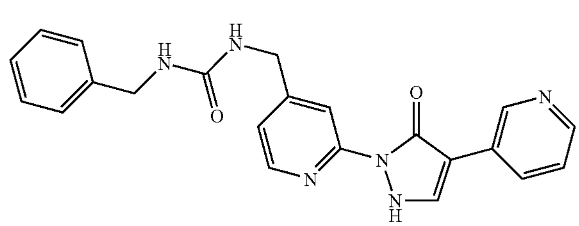 [SMILES: O=C(NCc1ccccc1)NCc1ccnc(-n2[nH]cc(-c3cccnc3)c2=O)c1] | 8% | m/z = 401; 1.25 min |

TABLE 1-continued

| Example No. | Structure | Yield (% of theory) | MS (ESI): [M + H]+; LC-MS: R_t (Method 8) |
|---|---|---|---|
| 31 | 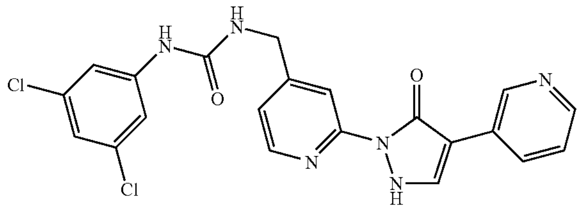 [SMILES: O=C(NCc1ccnc(-n2[nH]cc(-c3cccnc3)c2=O)c1)Nc1cc(Cl)cc(Cl)c1] | 13% | m/z = 456; 1.57 min |
| 32 | 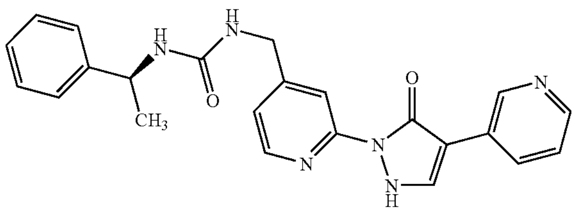 [SMILES: C[C@H](NC(=O)NCc1ccnc(-n2[nH]cc(-c3cccnc3)c2=O)c1)c1ccccc1] | 18% | m/z = 415; 1.30 min |
| 33 | 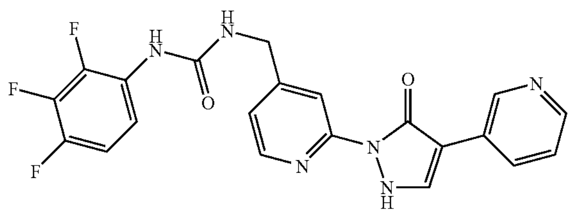 [SMILES: O=C(NCc1ccnc(-n2[nH]cc(-c3cccnc3)c2=O)c1)Nc1ccc(F)c(F)c1F] | 17% | m/z = 441; 1.38 min |
| 34 | 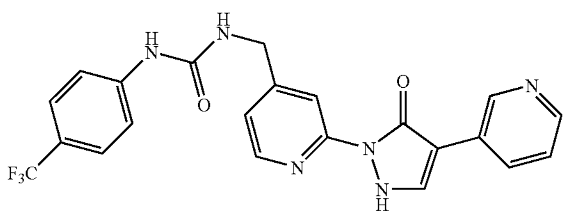 [SMILES: O=C(NCc1ccnc(-n2[nH]cc(-c3cccnc3)c2=O)c1)Nc1ccc(C(F)(F)F)cc1] | 15% | m/z = 455; 1.52 min |
| 35 | 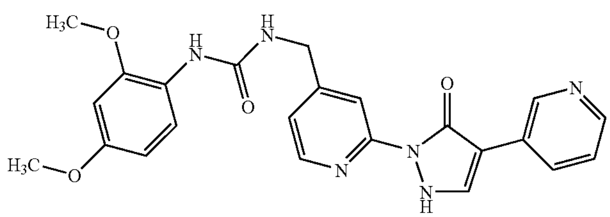 [SMILES: COc1ccc(NC(=O)NCc2ccnc(-n3[nH]cc(-c4cccnc4)c3=O)c2)c(OC)c1] | 10% | m/z = 447; 1.31 min |
| 36 | 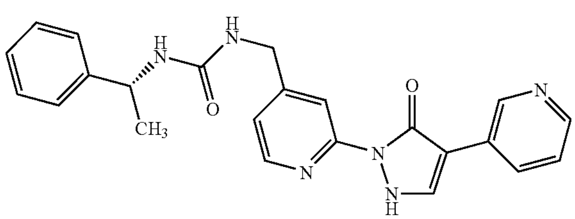 [SMILES: C[C@@H](NC(=O)NCc1ccnc(-n2[nH]cc(-c3cccnc3)c2=O)c1)c1ccccc1] | 16% | m/z = 415; 1.30 min |
| 37 | 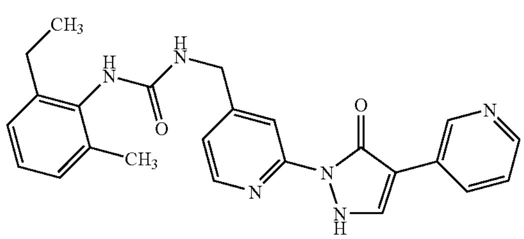 [SMILES: CCc1cccc(C)c1NC(=O)NCc1ccnc(-n2[nH]cc(-c3cccnc3)c2=O)c1] | 7% | m/z = 429; 1.37 min |

TABLE 1-continued

| Example No. | Structure | Yield (% of theory) | MS (ESI): [M + H]+; LC-MS: R_t (Method 8) |
|---|---|---|---|
| 38 | 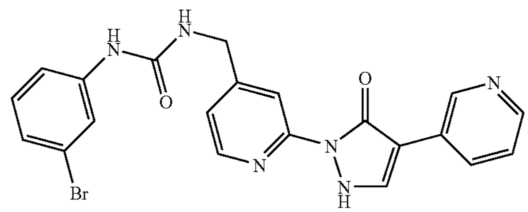 | 18% | m/z = 465; 1.44 min |
| 39 | 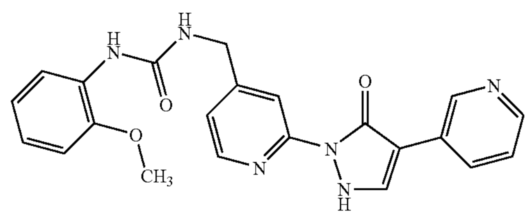 | 11% | m/z = 417; 1.33 min |
| 40 | 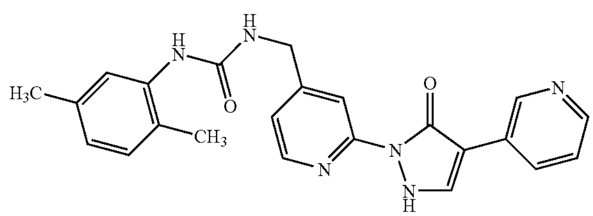 [SMILES: Cc1ccc(C)c(NC(=O)NCc2ccnc(-n3[nH]cc(-c4cccnc4)c3=O)c2)c1] | 8% | m/z = 415; 1.36 min |
| 41 | 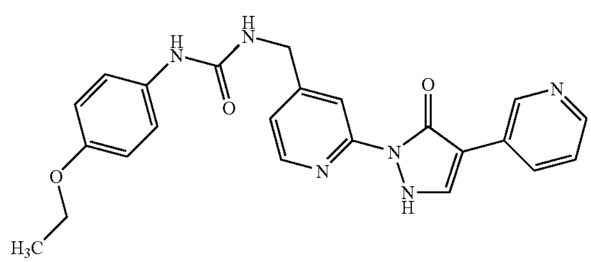 [SMILES: CCOc1ccc(NC(=O)NCc2ccnc(-n3[nH]cc(-c4cccnc4)c3=O)c2)cc1] | 14% | m/z = 431; 1.34 min |
| 42 | 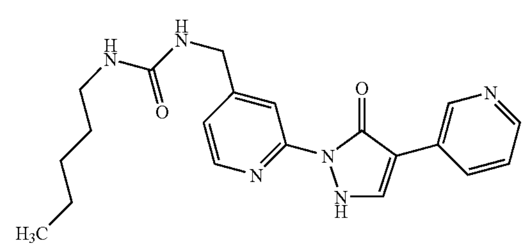 [SMILES: CCCCCNC(=O)NCc1ccnc(-n2[nH]cc(-c3cccnc3)c2=O)c1] | 15% | m/z = 381; 1.31 min |
| 43 | 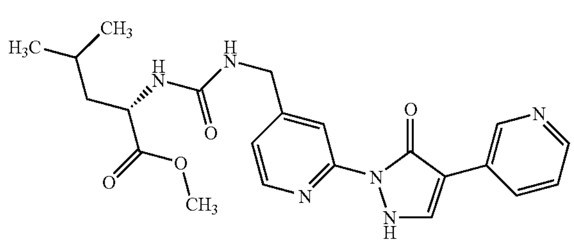 [SMILES: COC(=O)[C@H](CC(C)C)NC(=O)NCc1ccnc(-n2[nH]cc(-c3cccnc3)c2=O)c1] | 11% | m/z = 439; 1.33 min |

TABLE 1-continued

| Example No. | Structure | Yield (% of theory) | MS (ESI): [M + H]+; LC-MS: R_t (Method 8) |
|---|---|---|---|
| 44 | 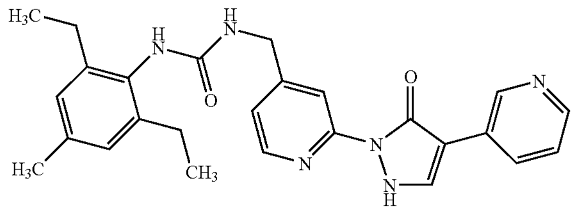 [SMILES: CCc1cc(C)cc(CC)c1NC(=O)NCc1ccnc(-n2[nH]cc(-c3cccnc3)c2=O)c1] | 14% | m/z = 457; 1.51 min |
| 45 | 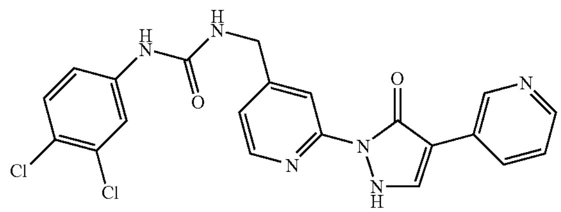 [SMILES: O=C(NCc1ccnc(-n2[nH]cc(-c3cccnc3)c2=O)c1)Nc1ccc(Cl)c(Cl)c1] | 14% | m/z = 455; 1.52 min |
| 46 | 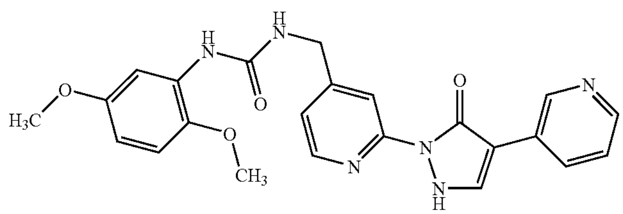 [SMILES: COc1ccc(OC)c(NC(=O)NCc2ccnc(-n3[nH]cc(-c4cccnc4)c3=O)c2)c1] | 10% | m/z = 447; 1.33 min |
| 47 | 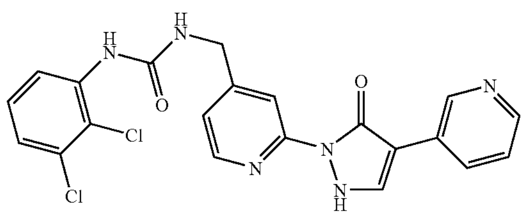 [SMILES: O=C(NCc1ccnc(-n2[nH]cc(-c3cccnc3)c2=O)c1)Nc1cccc(Cl)c1Cl] | 20% | m/z = 455; 1.47 min |
| 48 | 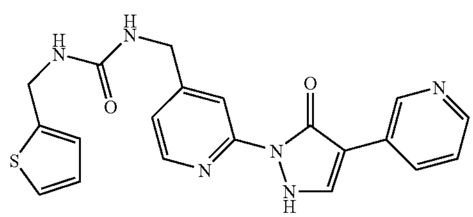 [SMILES: O=C(NCc1ccnc(-n2[nH]cc(-c3cccnc3)c2=O)c1)NCc1cccs1] | 4% | m/z = 407; 1.22 min |
| 49 | 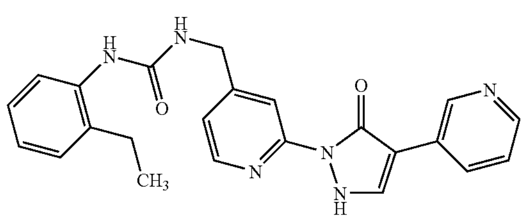 [SMILES: CCc1ccccc1NC(=O)NCc1ccnc(-n2[nH]cc(-c3cccnc3)c2=O)c1] | 15% | m/z = 415; 1.35 min |
| 50 | 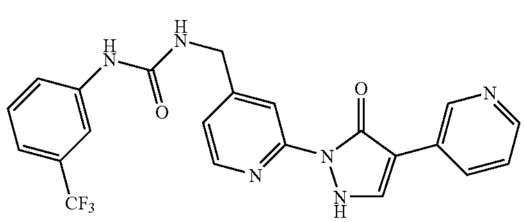 [SMILES: O=C(NCc1ccnc(-n2[nH]cc(-c3cccnc3)c2=O)c1)Nc1cccc(C(F)(F)F)c1] | 15% | m/z = 455; 1.48 min |

TABLE 1-continued

| Example No. | Structure | Yield (% of theory) | MS (ESI): [M + H]+; LC-MS: R_t (Method 8) |
|---|---|---|---|
| 51 | 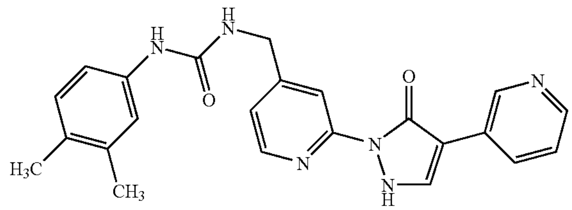 | 17% | m/z = 415; 1.42 min |
| 52 | 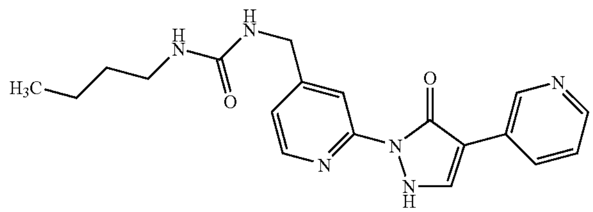 [SMILES: CCCCNC(=O)NCc1ccnc(-n2[nH]cc(-c3cccnc3)c2=O)c1] | 3% | m/z = 367; 1.21 min |
| 53 | 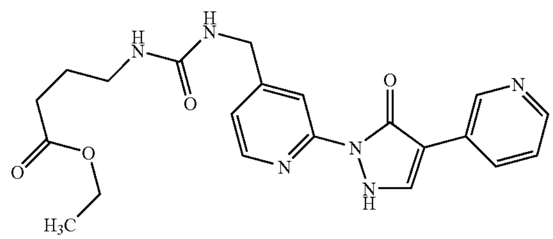 [SMILES: CCOC(=O)CCCNC(=O)NCc1ccnc(-n2[nH]cc(-c3cccnc3)c2=O)c1] | 13% | m/z = 425; 1.19 min |
| 54 | 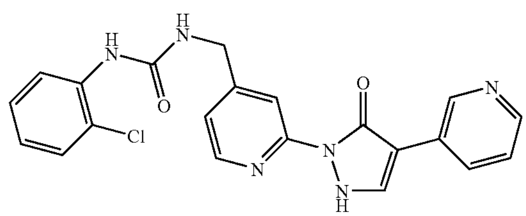 [SMILES: O=C(NCc1ccnc(-n2[nH]cc(-c3cccnc3)c2=O)c1)Nc1ccccc1Cl] | 16% | m/z = 421; 1.36 min |
| 55 | 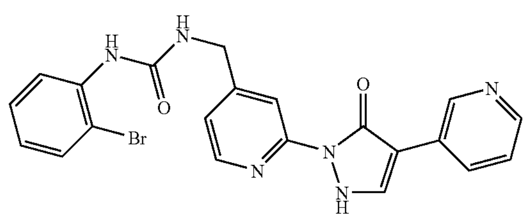 | 12% | m/z = 465; 1.37 min |
| 56 | 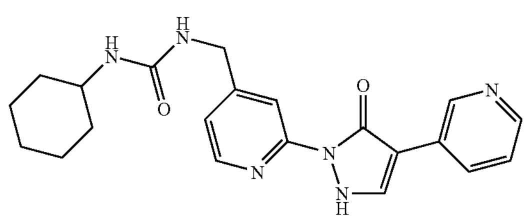 [SMILES: O=C(NCc1ccnc(-n2[nH]cc(-c3cccnc3)c2=O)c1)NC1CCCCC1] | 8% | m/z = 393; 1.29 min |
| 57 | 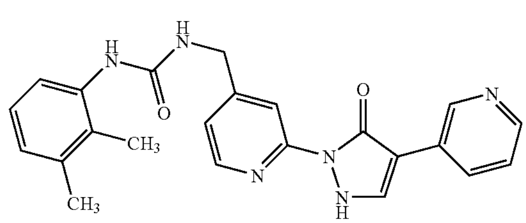 [SMILES: Cc1cccc(NC(=O)NCc2ccnc(-n3[nH]cc(-c4cccnc4)c3=O)c2)c1C] | 10% | m/z = 415; 1.35 min |

TABLE 1-continued

| Example No. | Structure | Yield (% of theory) | MS (ESI): [M + H]+; LC-MS: R_t (Method 8) |
|---|---|---|---|
| 58 | 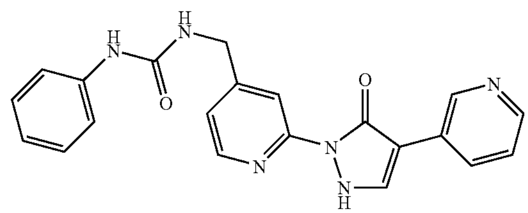 [SMILES: O=C(NCc1ccnc(-n2[nH]cc(-c3cccnc3)c2=O)c1)Nc1ccccc1] | 15% | m/z = 387; 1.28 min |
| 59 | 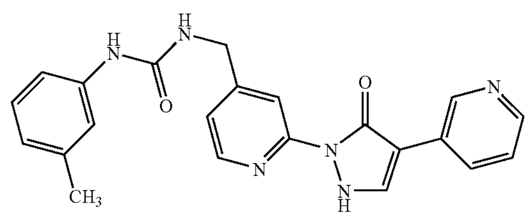 [SMILES: Cc1cccc(NC(=O)NCc2ccnc(-n3[nH]cc(-c4cccnc4)c3=O)c2)c1] | 19% | m/z = 401; 1.35 min |
| 60 | 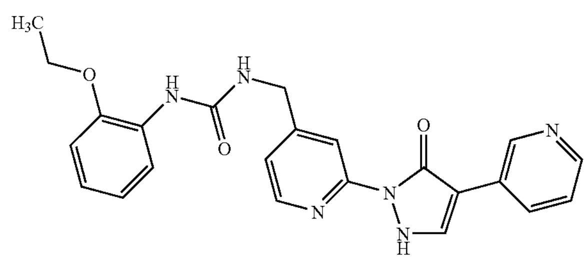 [SMILES: CCOc1ccccc1NC(=O)NCc1ccnc(-n2[nH]cc(-c3cccnc3)c2=O)c1] | 17% | m/z = 431; 1.40 min |
| 61 | 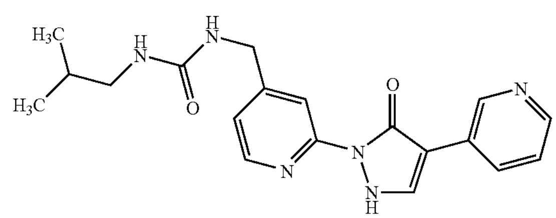 [SMILES: CC(C)CNC(=O)NCc1ccnc(-n2[nH]cc(-c3cccnc3)c2=O)c1] | 14% | m/z = 367; 1.20 min |
| 62 | 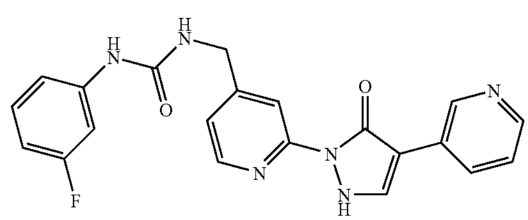 [SMILES: O=C(NCc1ccnc(-n2[nH]cc(-c3cccnc3)c2=O)c1)Nc1cccc(F)c1] | 10% | m/z = 405; 1.33 min |
| 63 | 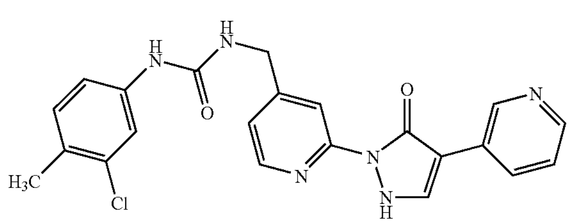 [SMILES: Cc1ccc(NC(=O)NCc2ccnc(-n3[nH]cc(-c4cccnc4)c3=O)c2)cc1Cl] | 26% | m/z = 435; 1.49 min |

TABLE 1-continued

| Example No. | Structure | Yield (% of theory) | MS (ESI): [M + H]+; LC-MS: R_t (Method 8) |
|---|---|---|---|
| 64 | 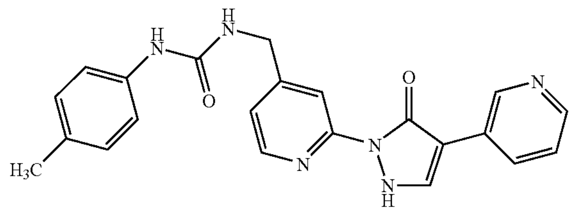 [SMILES: Cc1ccc(NC(=O)NCc2ccnc(-n3[nH]cc(-c4cccnc4)c3=O)c2)cc1] | 22% | m/z = 401; 1.35 min |
| 65 | 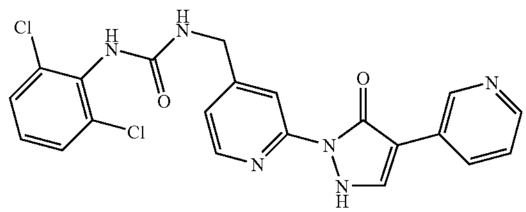 [SMILES: O=C(NCc1ccnc(-n2[nH]cc(-c3cccnc3)c2=O)c1)Nc1c(Cl)cccc1Cl] | 8% | m/z = 455; 1.28 min |
| 66 | 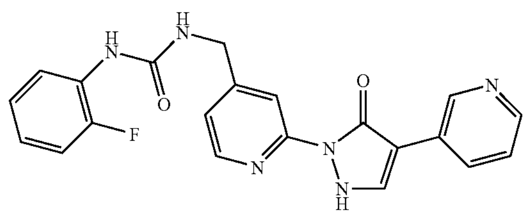 [SMILES: O=C(NCc1ccnc(-n2[nH]cc(-c3cccnc3)c2=O)c1)Nc1ccccc1F] | 12% | m/z = 405; 1.31 min |
| 67 | 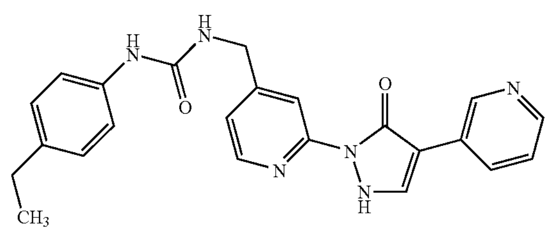 [SMILES: CCc1ccc(NC(=O)NCc2ccnc(-n3[nH]cc(-c4cccnc4)c3=O)c2)cc1] | 6% | m/z = 415; 1.44 min |
| 68 | 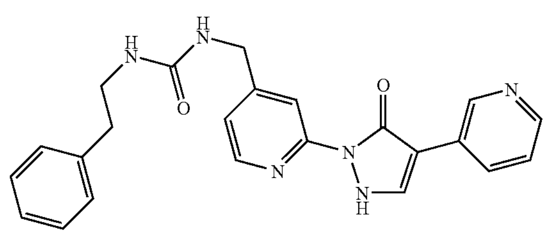 [SMILES: O=C(NCCc1ccccc1)NCc1ccnc(-n2[nH]cc(-c3cccnc3)c2=O)c1] | 13% | m/z = 415; 1.30 min |
| 69 | 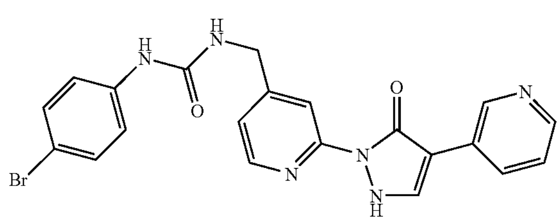 [SMILES: O=C(NCc1ccnc(-n2[nH]cc(-c3cccnc3)c2=O)c1)Nc1ccc(Br)cc1] | 7% | m/z = 465; 1.44 min |

Example 70

[6-(5-Oxo-4-pyridin-3-yl-2,5-dihydro-1H-pyrazol-1-yl)pyridin-3-yl]methyl (2,3-dimethylphenyl)-carbamate

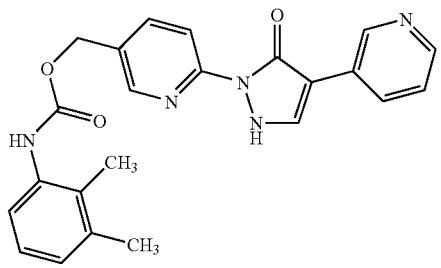 [SMILES: Cc1cccc(NC(=O)OCc2ccc(-n3[nH]cc(-c4cccnc4)c3=O)nc2)c1C]

2.7 g (10 mmol) of 2-[5-(hydroxymethyl)pyridin-2-yl]-4-pyridin-3-yl-1,2-dihydro-3H-pyrazol-3-one [for the preparation, see WO 2006/114213] are dissolved in 60 ml of 1,2-dichloroethane and provided as a stock solution.

15 mg (0.1 mmol) of 1-isocyanato-2,3-dimethylbenzene are initially charged, and 600 µl (0.1 mmol) of the above stock solution and 26 mg (0.2 mmol) of N,N-diisopropylethylamine (Hünig base) are added. The reaction mixture is stirred at RT for 16 h. For work-up, the solvent is removed under reduced pressure, the residue is taken up in DMSO and filtered and the filtrate is purified directly by preparative LC-MS (Method 9). The product fractions are concentrated under reduced pressure, and the residue is dried.

Yield: 0.6 mg (2% of theory)

LC-MS (Method 9): $R_t$=1.58 min; MS (ESIpos): m/z=416 [M+H]$^+$.

The compounds listed in Table 2 are prepared analogously to the procedure of Example 70 from 0.1 mmol of 2-[5-(hydroxymethyl)pyridin-2-yl]-4-pyridin-3-yl-1,2-dihydro-3H-pyrazol-3-one and 0.1 mmol of the appropriate isocyanate:

TABLE 2

| Example No. | Structure | Yield (% of theory) | MS (ESI): [M + H]$^+$; LC-MS: $R_t$ (Method 9) |
|---|---|---|---|
| 71 | 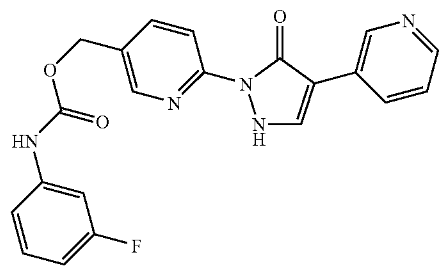 [SMILES: O=C(Nc1cccc(F)c1)OCc1ccc(-n2[nH]cc(-c3cccnc3)c2=O)nc1] | 4% | m/z = 406; 1.55 min |
| 72 | 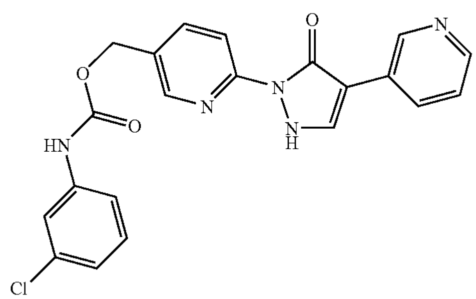 [SMILES: O=C(Nc1cccc(Cl)c1)OCc1ccc(-n2[nH]cc(-c3cccnc3)c2=O)nc1] | 2% | m/z = 422; 1.63 min |
| 73 | 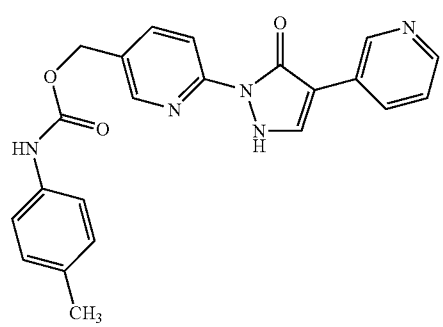 [SMILES: Cc1ccc(NC(=O)OCc2ccc(-n3[nH]cc(-c4cccnc4)c3=O)nc2)cc1] | 1% | m/z = 402; 1.57 min |

TABLE 2-continued

| Example No. | Structure | Yield (% of theory) | MS (ESI): [M + H]+; LC-MS: R$_t$ (Method 9) |
|---|---|---|---|
| 74 | 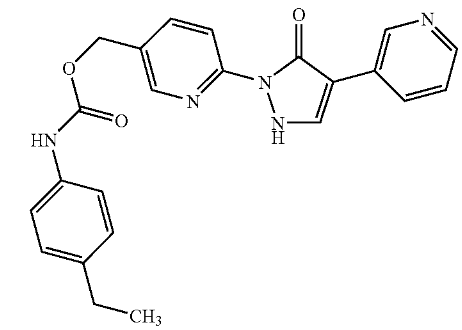 [SMILES: CCc1ccc(NC(=O)OCc2ccc(-n3[nH]cc(-c4cccnc4)c3=O)nc2)cc1] | 3% | m/z = 416; 1.67 min |
| 75 | 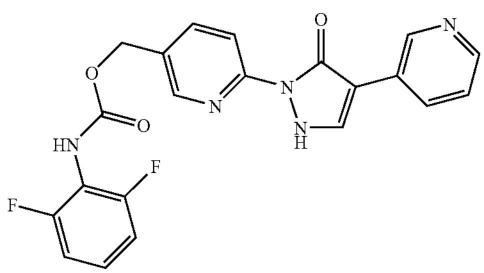 [SMILES: O=C(Nc1c(F)cccc1F)OCc1ccc(-n2[nH]cc(-c3cccnc3)c2=O)nc1] | 2% | m/z = 424; 1.44 min |
| 76 | 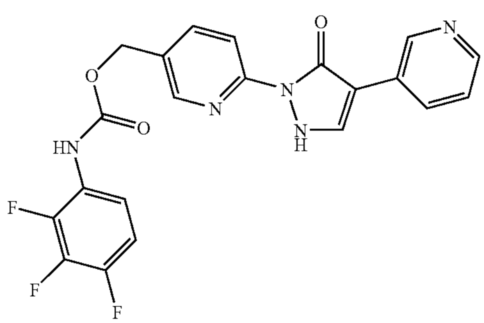 [SMILES: O=C(Nc1ccc(F)c(F)c1F)OCc1ccc(-n2[nH]cc(-c3cccnc3)c2=O)nc1] | 2% | m/z = 442; 1.58 min |
| 77 | 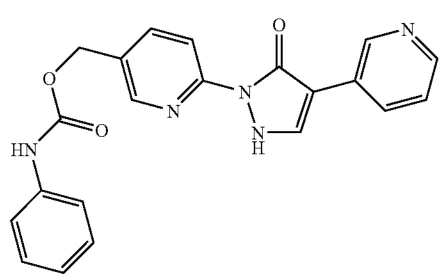 [SMILES: O=C(Nc1ccccc1)OCc1ccc(-n2[nH]cc(-c3cccnc3)c2=O)nc1] | 2% | m/z = 388; 1.48 min |
| 78 | 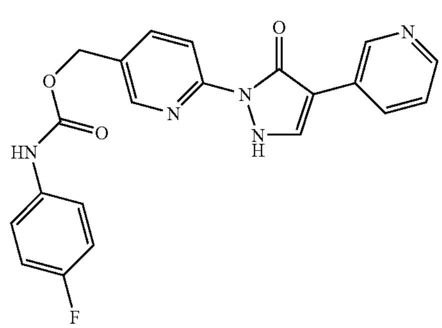 [SMILES: O=C(Nc1ccc(F)cc1)OCc1ccc(-n2[nH]cc(-c3cccnc3)c2=O)nc1] | 4% | m/z = 406; 1.52 min |

TABLE 2-continued

| Example No. | Structure | Yield (% of theory) | MS (ESI): [M + H]+; LC-MS: R$_t$ (Method 9) |
|---|---|---|---|
| 79 | 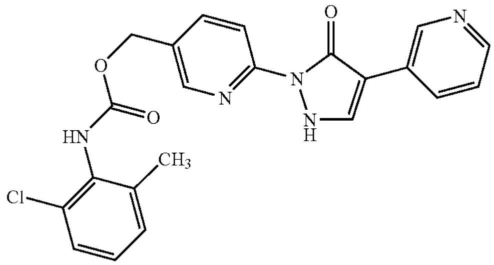 [SMILES: Cc1cccc(Cl)c1NC(=O)OCc1ccc(-n2[nH]cc(-c3cccnc3)c2=O)nc1] | 2% | m/z = 436; 1.53 min |
| 80 | 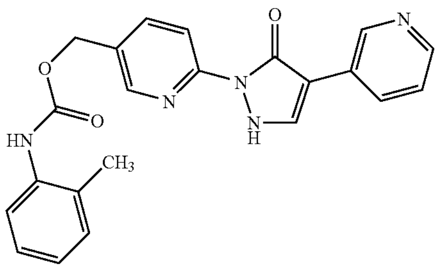 [SMILES: Cc1ccccc1NC(=O)OCc1ccc(-n2[nH]cc(-c3cccnc3)c2=O)nc1] | 1% | m/z = 402; 1.51 min |
| 81 | 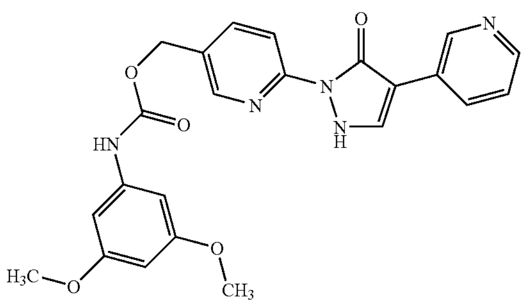 [SMILES: COc1cc(NC(=O)OCc2ccc(-n3[nH]cc(-c4cccnc4)c3=O)nc2)cc(OC)c1] | 2% | m/z = 448; 1.55 min |

Example 82

4-Pyridin-3-yl-2-(4-{[(pyridin-2-ylmethyl)amino]methyl}pyridin-2-yl)-1,2-dihydro-3H-pyrazol-3-one

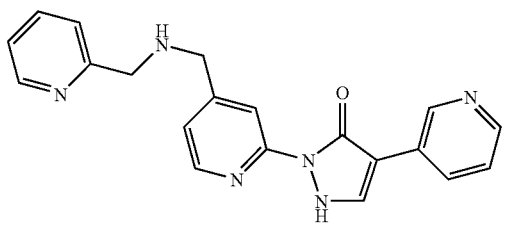 [SMILES: O=c1c(-c2cccnc2)c[nH]n1-c1cc(CNCc2ccccn2)ccn1]

2.7 g (10 mmol) of the compound from Example 4A are dissolved in 60 ml of ethanol and provided as a stock solution.

11 mg (0.1 mmol) of pyridine-2-carbaldehyde are initially charged, and 600 μl (0.1 mmol) of the above stock solution and 26 mg (0.2 mmol) of N,N-diisopropylethylamine (Hünig base) are added. The reaction mixture is stirred at RT for 16 h, 4 mg (0.1 mmol) of sodium borohydride are then added and the mixture is shaken at RT for a further 3 h. For work-up, the mixture is added to 100 μl of water, the solvent is removed under reduced pressure and the residue is dissolved in DMSO. After filtration, the filtrate is purified by preparative LC-MS (Method 9). The product fractions are comcentrated under reduced pressure, and the residue is dried.

Yield: 0.7 mg (2% of theory)

LC-MS (Method 9): R$_t$=1.56 min; MS (ESIpos): m/z=358 [M+H]+.

The compounds listed in Table 3 are prepared analogously to the procedure of Example 82 from 0.1 mmol of the compound from Example 4A and 0.1 mmol of the appropriate aldehyde:

TABLE 3

| Example No. | Structure | Yield (% of theory) | MS (ESI): [M + H]+; LC-MS: R$_t$ (Method 9) |
|---|---|---|---|
| 83 | 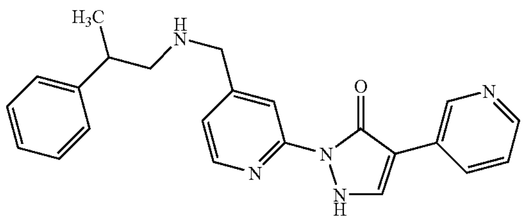 [SMILES: CC(CNCc1ccnc(-n2[nH]cc(-c3cccnc3)c2=O)c1)c1ccccc1] | 2% | m/z = 386; 1.31 min |
| 84 | 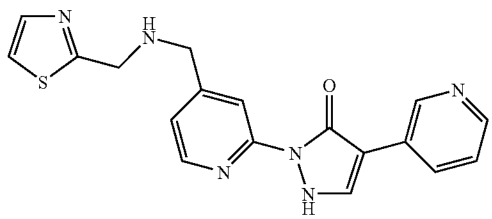 [SMILES: O=c1c(-c2cccnc2)c[nH]n1-c1cc(CNCc2nccs2)ccn1] | 2% | m/z = 364; 1.59 min |
| 85 | 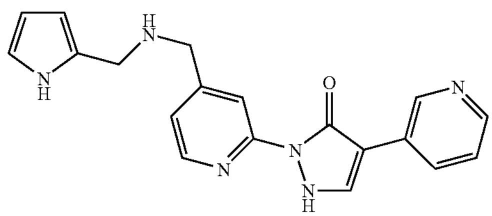 [SMILES: O=c1c(-c2cccnc2)c[nH]n1-c1cc(CNCc2ccc[nH]2)ccn1] | 4% | m/z = 347; 1.36 min |

Example 86

2-(4,5-Dimethylpyridin-2-yl)-4-pyridin-3-yl-1,2-dihydro-3H-pyrazol-3-one

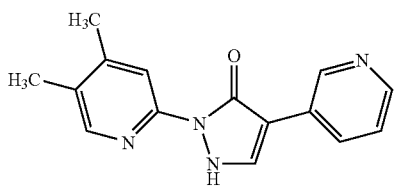 [SMILES: Cc1cnc(-n2[nH]cc(-c3cccnc3)c2=O)cc1C]

220 mg (1.0 mmol) of the compound from Example 2A are initially charged in 5 ml of ethanol. 137 mg (1.0 mmol) of the compound from Example 21A and 38 mg (0.2 mmol) of p-toluenesulfonic acid are added, and the mixture is stirred under reflux for 16 h. The mixture is then allowed to cool to RT, and the solid formed is filtered off, washed with tert-butyl methyl ether and dried under high vacuum. This gives 28 mg of the title compound. The mother liquor is put aside and used for preparing the hydrochloride (see Example 87).

Yield: 28 mg (11% of theory)

LC-MS (Method 6): R$_t$=1.10 min; MS (ESIpos): m/z=267 [M+H]+;

$^1$H-NMR (400 MHz, DMSO-d$_6$): δ=9.05 (s, 1H), 8.37-8.28 (m, 2H), 8.24-8.15 (m, 2H), 8.09-7.95 (s, 1H), 7.36 (dd, 1H), 2.36 (s, 3H), 2.25 (s, 3H).

Example 87

2-(4,5-Dimethylpyridin-2-yl)-4-pyridin-3-yl-1,2-dihydro-3H-pyrazol-3-one hydrochloride

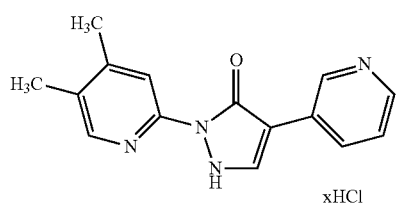 [SMILES: Cc1cnc(-n2[nH]cc(-c3cccnc3)c2=O)cc1C]

The mother liquor obtained during the preparation of Example 86 (see above) is concentrated on a rotary evaporator, and the residue is purified by preparative HPLC (RP18-column; mobile phase: acetonitrile/water-gradient with addition of 0.1% TFA to the water). The residue obtained after the concentration of the product fractions is triturated with 5 ml of a 4 N solution of hydrogen chloride in dioxane for 30 min. The solid is filtered off, washed twice with tert-butyl methyl ether and dried under high vacuum.

Yield: 100 mg (33% of theory, based on 1.0 mmol of the compound from Example 21A)

LC-MS (Method 6): R$_t$=1.12 min; MS (ESIpos): m/z=267 [M+H]+;

$^1$H-NMR (400 MHz, DMSO-d$_6$): δ=9.32 (s, 1H), 8.94 (d, 1H), 8.61 (s, 1H), 8.57 (d, 1H), 8.23 (s, 1H), 8.21 (s, 1H), 8.00 (dd, 1H), 2.41 (s, 3H), 2.28 (s, 3H).

Example 88

2-[5-(2,2-Dimethylpropoxy)pyridin-2-yl]-4-pyridin-3-yl-1,2-dihydro-3H-pyrazol-3-one

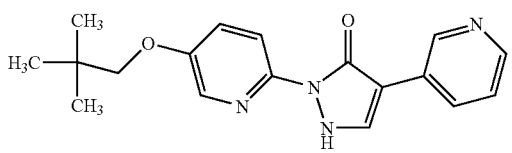 [SMILES: CC(C)(C)COc1ccc(-n2[nH]cc(-c3cccnc3)c2=O)nc1]

220 mg (1.0 mmol) of the compound from Example 2A are initially charged in 5 ml of ethanol. 260 mg (purity 75%, 1.0 mmol) of the compound from Example 19A and 38 mg (0.2 mmol) of p-toluenesulfonic acid are added, and the mixture is stirred under reflux for 16 h. The mixture is then allowed to cool to RT, and the solid formed is filtered off, washed with tert-butyl methyl ether and dried under high vacuum. This gives 37 mg of the title compound. The mother liquor is put aside and used for preparing the hydrochloride (see Example 89).

Yield: 37 mg (11% of theory)

LC-MS (Method 5): $R_t$=1.05 min; MS (ESIpos): m/z=325 [M+H]$^+$;

$^1$H-NMR (400 MHz, DMSO-$d_6$): δ=9.08 (s, 1H), 8.45-8.35 (m, 2H), 8.32-8.15 (m, 3H), 7.70 (dd, 1H), 7.37 (dd, 1H), 3.76 (s, 2H), 1.01 (s, 9H).

Example 89

2-[5-(2,2-Dimethylpropoxy)pyridin-2-yl]-4-pyridin-3-yl-1,2-dihydro-3H-pyrazol-3-one hydrochloride

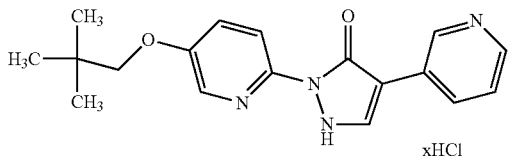 [SMILES: CC(C)(C)COc1ccc(-n2[nH]cc(-c3cccnc3)c2=O)nc1]

The mother liquor obtained during the preparation of Example 88 (see above) is concentrated on a rotary evaporator, and the residue is purified by preparative HPLC (RP18-column; mobile phase: acetonitrile/water-gradient with addition of 0.1% TFA to the water). The residue obtained after the concentration of the product fractions is triturated with 5 ml of a 4 N solution of hydrogen chloride in dioxane for 30 min. The solid is filtered off, washed twice with tert-butyl methyl ether and dried under high vacuum.

Yield: 160 mg (44% of theory, based on 1.0 mmol of the compound from Example 19A)

LC-MS (Method 2): $R_t$=1.52 min; MS (ESIpos): m/z=325 [M+H]$^+$;

$^1$H-NMR (400 MHz, DMSO-$d_6$): δ=9.39 (s, 1H), 8.96 (d, 1H), 8.74 (s, 1H), 8.64 (d, 1H), 8.30 (d, 1H), 8.21 (d, 1H), 8.00 (dd, 1H), 7.70 (dd, 1H), 3.78 (s, 2H), 1.01 (s, 9H).

B. EVALUATION OF THE PHARMACOLOGICAL ACTIVITY

The pharmacological properties of the compounds according to the invention can be demonstrated in the following assays:

Abbreviations

| | |
|---|---|
| DMEM | Dulbecco's modified Eagle medium |
| FCS | fetal calf serum |
| TMB | 3,3',5,5'-tetramethylbenzidine |
| Tris | tris(hydroxymethyl)aminomethane |

1. In Vitro Tests for Determination of the Activity and Selectivity of HIF Prolyl 4-Hydroxylase Inhibitors 1.a) Inhibition of the Activity of HIF Prolyl Hydroxylase:

Hydroxylated HIF bonds specifically to the von Hippel-Lindau protein-elongin B-elongin C complex (VBC complex). This interaction occurs only if HIF is hydroxylated on a conserved prolyl radical. It is the basis for the biochemical determination of HIF prolyl hydroxylase activity.

The test is carried out as described [Oehme F., Jonghaus W., Narouz-Ott L., Huetter J., Flamme I., *Anal. Biochem.* 330 (1), 74-80 (2004)]:

A clear 96-well microtiter plate coated with NeutrAvidin HBC (Pierce) is incubated with blocker casein for 30 minutes. The plate is then washed three times with 200 µl each time of wash buffer (50 mM Tris, pH 7.5, 100 mM NaCl, 10% (v/v) blocker casein, 0.05% (v/v) Tween 20) per well. The peptide biotin-DLDLEMLAPYIPMDDDFQL (Eurogentec, 4102 Seraing, Belgium) is added in a concentration of 400 nM in 100 µl wash buffer. This peptide serves as a substrate for the prolyl hydroxylation and is bonded to the microtiter plate. After incubation for 60 minutes, the plate is washed three times with wash buffer, incubated with 1 mM biotin in blocker casein for 30 minutes and then washed again three times with wash buffer.

To carry out the prolyl hydroxylase reaction, the peptide substrate bonded to the plate is incubated with a cell lysate containing prolyl hydroxylase for 1 to 60 minutes. The reaction takes place in 100 µl reaction buffer (20 mM Tris, pH 7.5, 5 mM KCl, 1.5 mM MgCl2, 1 µM-1 mM 2-oxoglutarate, 10 µM FeSO4, 2 mM ascorbate) at room temperature. The reaction mixture moreover contains various concentrations of the prolyl hydroxylase inhibitor to be tested. The test substance is preferably, but not exclusively, employed at concentrations of between 1 nM and 100 µM. The reaction is stopped by washing the plate three times with wash buffer.

For quantitative determination of the prolyl hydroxylation, a fusion protein which contains both thioredoxin from *E. coli* and the VBC complex in 80 µl bonding buffer (50 mM Tris, pH 7.5, 120 mM NaCl) is added. After 15 minutes, 10 µl of a solution of polyclonal anti-thioredoxin antibodies from rabbit in bonding buffer are added. After a further 30 minutes, 10 µl of a solution of anti-rabbit immunoglobulin coupled to horseradish peroxidase in bonding buffer are added. After incubation at room temperature for 30 minutes, the plate is washed three times with wash buffer in order to remove non-bonded VBC complex and antibodies. To determine the amount of bonded VBC complex, the plate is incubated with TMB for 15 minutes. The color reaction is ended by addition of 100 µl 1 M sulfuric acid. The amount of bonded VBC complex is determined by measurement of the optical density at 450 nm. It is proportional to the amount of hydroxylated proline in the peptide substrate.

Alternatively, a VBC complex coupled to europium (Perkin Elmer) can be used for detection of the prolyl hydroxylation. In this case, the amount of bonded VBC complex is determined by the fluorescence with respect to time. The use of VBC complex labeled with [$^{35}$S]-methionine is moreover possible. For this, the radioactively labeled VBC complex can be prepared by in vitro transcription-translation in reticulocyte lysate.

The embodiment examples inhibit the activity of HIF prolyl hydroxylase in this test with an $IC_{50}$ value of $\leq 30$ μM. Representative $IC_{50}$ values for the embodiment examples are reproduced in the following Table 1:

TABLE 1

| Example No. | $IC_{50}$ [μM] |
|---|---|
| 5 | 6.3 |
| 8 | 5.2 |
| 10 | 0.26 |
| 18 | 0.91 |
| 22 | 3.24 |
| 65 | 0.9 |
| 80 | 1.6 |
| 89 | 3.7 |

1.b) Cellular, Functional In Vitro Test:

The activity of the compounds according to the invention is quantified with the aid of a recombinant cell line. The cell is originally derived from a human lung carcinoma cell line (A549, ATCC: American Type Culture Collection, Manassas, Va. 20108, USA). The test cell line is transfected in a stable manner with a vector which contains the reporter gene of *Photinus pyralis* luciferase (called luciferase in the following) under the control of an artificial minimal promoter. The minimal promoter comprises two hypoxia-responsible elements upstream of a TATA box [Oehme F., Ellinghaus P., Kolkhof P., Smith T. J., Ramakrishnan S., Hütter J., Schramm M., Flamme I., *Biochem. Biophys. Res. Commun.* 296 (2), 343-9 (2002)]. Under the effect of hypoxia (for example culturing in the presence of 1% oxygen for 24 hours) or under the action of non-selective dioxygenase inhibitors (for example desferroxamine in a concentration of 100 μM, cobalt chloride in a concentration of 100 μM or N-oxalylglycine diethyl ester in a concentration of 1 mM), the test cell line produces luciferase, which can be detected and quantified with the aid of suitable bioluminescence reagents (for example Steady-Glo® Luciferase Assay System, Promega Corporation, Madison, Wis. 53711, USA) and a suitable luminometer.

Test procedure: On the day before the test, the cells are plated out in an exactly calculated amount of culture medium (DMEM, 10% FCS, 2 mM glutamine) in 384- or 1536-well microtiter plates and kept in a cell incubator (96% atmospheric humidity, 5% v/v $CO_2$, 37° C.). On the test day, the test substances are added to the culture medium in graduated concentrations. No test substance is added to the cells in batches serving as negative controls. As a positive control for determination of the sensitivity of the cell to inhibitors, desferroxamine for example is added in a final concentration of 100 μM. Six to 24 hours after transfer of the test substances into the wells of the microtiter plates, the resulting light signal is measured in the luminometer. A dose/effect relationship is plotted with the aid of the measurement values, which serves as the basis for determining the half-maximum active concentration (called the $EC_{50}$ value).

1.c) Cellular, Functional In Vitro Test of Modification of the Gene Expression:

To investigate the modification of the expression of specific mRNAs in human cell lines after treatment with test substances, the following cell lines are cultured on 6- or 24-well plates: human hepatoma cells (HUH, JCRB Cell Bank, Japan), human embryonal kidney fibroblasts (HEK/293, ATCC, Manassas, Va. 20108, USA), human cervical carcinoma cells (HeLa, ATCC, Manassas, Va. 20108, USA), human umbilical vein endothelial cells (HUVEC, Cambrex, East Rutherford, N.J. 07073, USA). 24 hours after addition of the test substances, the cells are washed with phosphate-buffered saline and the total RNA is obtained from them using a suitable method (for example Trizol® reagent, Invitrogen GmbH, 76131 Karlsruhe, Germany).

For a typical analysis experiment, 1 μg each of the total RNA obtained in this way is digested with DNase I and translated into a complementary DNA (cDNA) using a suitable reverse transcriptase reaction (ImProm-II Reverse Transcription System, Promega Corporation, Madison, Wis. 53711, USA). 2.5% of the cDNA batch obtained in this way is used in each case for the polymerase chain reaction. The expression level of the mRNA of the genes to be investigated is investigated by means of the real time quantitative polymerase chain reaction [TaqMan-PCR; Heid C. A., Stevens J., Livak K. J., Williams P. M., *Genome Res.* 6 (10), 986-94 (1996)] using an ABI Prism 7700 sequence detection instrument (Applied Biosystems, Inc.). The primer-probe combinations used here are generated by means of Primer Express 1.5 Software (Applied Biosystems, Inc.). Specifically, the mRNAs of erythropoietin, carboanhydrase IX, lactate dehydrogenase A and vascular endothelial cell growth factor are investigated.

Substances according to the present invention lead to a significant dose-dependent increase in the mRNA of hypoxia-induced genes in cells of human origin.

2. In Vivo Tests for Detection of the Action in the Cardiovascular System 2.a) In Vivo Test of Modification of Gene Expression:

The test compounds dissolved in suitable solvents are administered to mice or rats either orally by stomach tube administration, intraperitoneally or intravenously. Typical dosages are 0.1, 0.5, 1, 5, 10, 20, 50, 100 and 300 mg substance per kg of body weight and administration. Control animals receive only solvent. 4, 8 or 24 hours after administration of the test substance the animals are sacrificed with an overdose of isoflurane and a subsequent fracture of the neck and the organs to be investigated are removed. Parts of the organs are shock-frozen in liquid nitrogen. Total RNA is obtained from the organ parts as described under B.1.a) and this is translated into a cDNA. The expression level of the mRNA of the genes to be investigated is investigated by means of the real time quantitative polymerase chain reaction [TaqMan-PCR; Heid C. A., Stevens J., Livak K. J., Williams P. M., *Genome Res.* 6 (10), 986-94 (1996)] using an ABI Prism 7700 sequence detection instrument (Applied Biosystems, Inc.).

Substances according to the present invention lead to a significant dose-dependent increase in the mRNA of erythropoietin in the kidney after oral or parenteral administration compared with the placebo control.

2.b) Determination of the Erythropoietin Level in Serum:

The test substance in a suitable solvent is administered to mice or rats either intraperitoneally or orally once or twice daily. Typical dosages are 0.1, 0.5, 1, 5, 10, 20, 50, 100 and 300 mg substance per kg of body weight and administration. Placebo control animals receive only solvent. Before the administration and four hours after the last administration of substance, 50 μl of blood are taken from the animals from the retroorbital venous plexus or the tail vein under short narcosis. The blood is rendered uncoagulable by addition of lithium heparin. The blood plasma is obtained by centrifugation. The content of erythropoietin in the blood plasma is determined with the aid of an erythropoietin-ELISA (Quantikine® mouse Epo Immunoassay, R&D Systems, Inc., Minneapolis, USA) in accordance with the manufacturer's instructions. The measurement values are converted into pg/ml with the aid of a reference measurement recorded for mouse erythropoietin.

Substances according to the present invention lead to a significant dose-dependent increase in the plasma erythropoietin after oral and parenteral administration compared with the starting value and the placebo control.

2.c) Determination of the Cell Composition of Peripheral Blood:

The test substance in a suitable solvent is administered to mice or rats either intraperitoneally or orally once or twice daily for several days. Typical dosages are for example 0.1, 0.5, 1, 5, 10, 20, 50, 100 and 300 mg substance per kg of body weight and administration. Control animals receive only solvent. At the end of the study, blood is taken from the animals from the venous plexus of the corner of the eye or the tail vein under short narcosis and is rendered uncoagulable by addition of sodium citrate. The concentrations of erythrocytes, leukocytes and thrombocytes are determined in the blood samples in a suitable electronic measuring apparatus. The concentration of the reticulocytes is determined by microscope screening of in each case 1000 erythrocytes with the aid of blood smears stained with a stain solution suitable for this purpose (KABE Labortechnik, Nümbrecht). For determination of the hematocrit, blood is taken from the retroorbital venous plexus by means of a hematocrit capillary and the hematocrit value is read off manually after centrifugation of the capillary in a centrifuge suitable for this purpose.

Substances according to the present invention lead to a significant dose-dependent increase in the hematocrit, the erythrocyte count and the reticulocytes after oral and parenteral administration compared with the starting value and the placebo control.

C. EMBODIMENT EXAMPLES FOR PHARMACEUTICAL COMPOSITIONS

The compounds according to the invention can be converted into pharmaceutical formulations as follows.
Tablet:
Composition:
100 mg of the compound according to the invention, 50 mg lactose (monohydrate), 50 mg maize starch (native), 10 mg polyvinylpyrrolidone (PVP 25) (BASF, Ludwigshafen, Germany) and 2 mg magnesium stearate.

Tablet weight 212 mg. Diameter 8 mm, radius of curvature 12 mm.
Preparation:

The mixture of compound according to the invention, lactose and starch is granulated with a 5% strength solution (w/w) of the PVP in water. After drying, the granules are mixed with the magnesium stearate for 5 minutes. This mixture is pressed with a conventional tablet press (for tablet format see above). A pressing force of 15 kN is used as the recommended value for the pressing.

Suspension for Oral Administration:
Composition:
1000 mg of the compound according to the invention, 1000 mg ethanol (96%), 400 mg Rhodigel® (xanthan gum from FMC, Pennsylvania, USA) and 99 g water.

10 ml of oral suspension correspond to an individual dose of 100 mg of the compound according to the invention.
Preparation:

The Rhodigel is suspended in ethanol and the compound according to the invention is added to the suspension. The water is added with stirring. The mixture is stirred for approx. 6 h until swelling of the Rhodigel has ended.
Solution for Oral Administration:
Composition:

500 mg of the compound according to the invention, 2.5 g polysorbate and 97 g polyethylene glycol 400.20 g of oral solution correspond to an individual dose of 100 mg of the compound according to the invention.
Preparation:

The compound according to the invention is suspended in a mixture of polyethylene glycol and polysorbate, while stirring. The stirring operation is continued until dissolution of the compound according to the invention is complete.
i.v. Solution:

The compound according to the invention is dissolved in a concentration below the saturation solubility in a physiologically acceptable solvent (for example isotonic saline solution, glucose solution 5% and/or PEG 400 solution 30%). The solution is subjected to sterile filtration and is transferred into sterile and pyrogen-free injection containers.

The invention claimed is:
1. A compound of the formula (I)

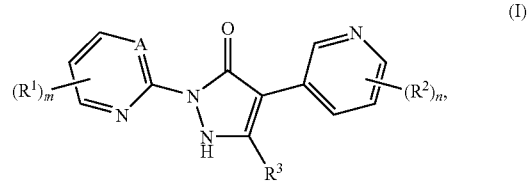

A represents CH,
$R^1$ and $R^2$ are identical or different and for each individual occurrence represent a substituent independently of one another selected from the group consisting of halogen, cyano, nitro, hydroxyl, amino, hydroxycarbonyl, aminocarbonyl, $(C_1-C_6)$-alkyl, $(C_1-C_6)$-alkoxy, $(C_3-C_7)$-cycloalkyl, phenyl, —C(=O)—$R^4$, —C(=O)—$OR^5$, —C(=O)—$NR^6R^7$, —O—C(=O)—$R^8$, —O—C(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2$—$R^{19}$, —$SO_2$—$R^{20}$, —$SO_2$—$NR^{21}R^{22}$, —$OR^{23}$, —$SR^{24}$ and —$NR^{25}R^{26}$ in which (i) $(C_1-C_6)$-alkyl and $(C_1-C_6)$-alkoxy for their part may in each case be mono- to trisubstituted by identical or different radicals selected from the group consisting of halogen, cyano, oxo, hydroxyl, amino, hydroxycarbonyl, aminocarbonyl, $(C_3-C_7)$-cycloalkyl, phenyl, —C(=O)—$R^4$, —C(=O)—$OR^5$, —C(=O)—$NR^6R^7$, —O—C(=O)—$R^8$, —O—C(=O)—$NR^9R^{10}$, $NR^{11}$—C(=O)—$R^{12}$, —$NR^{13}$(=O)—$OR^{14}$, —$NR^{15}$—C(=O)—$NR^{16}R^{17}$, $NR^{18}$—$SO_2$—$R^{19}$, —$SO_2$—$R^{20}$, —$SO_2$—$NR^{21}R^{22}$, —$OR^{23}$, —$SR^{24}$ and —$NR^{25}R^{26}$, where the last-mentioned cycloalkyl, and phenyl radicals for their part may in each case be substituted up to three times by identical or different substituents selected from the group consisting of halogen, cyano, $(C_1$-$C_4)$-alkyl, trifluoromethyl, hydroxyl, $(C_1$-$C_4)$-alkoxy, trifluoromethoxy, oxo, amino, mono-$(C_1$-$C_4)$-alkylamino, di-$(C_1$-$C_4)$-alkylamino, hydroxycarbonyl and $(C_1$-$C_4)$-alkoxycarbonyl, (ii) $(C_3$-$C_7)$-cycloalkyl, and phenyl for their part may in each case be mono- to trisubstituted by identical or different radicals selected from the group consisting of $(C_1$-$C_6)$-alkyl, halogen, cyano, oxo, hydroxyl, amino, hydroxycarbonyl, aminocarbonyl, —C(=O)—$R^4$, —C(=O)—$OR^5$, —C(=O)—$NR^6R^7$, —O—C(=O)—$R^8$, —O—C(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2$—$R^{19}$, —$SO_2$—$R^{20}$, —$SO_2$—$NR^{21}R^{22}$, —$OR^{23}$, —$SR^{24}$ and —$NR^{25}R^{26}$, where the last-mentioned alkyl radical for its part may be substituted up to three times by identical or different substituents from the group consisting of halogen, cyano, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl, $(C_1$-$C_4)$-alkoxycarbonyl, $(C_3$-$C_7)$-cycloalkyl, and phenyl, (iii) $R^4$, $R^5$, $R^6$, $R^8$, $R^9$, $R^{12}$, $R^{14}$, $R^{16}$, $R^{19}$, $R^{20}$, $R^{21}$, $R^{23}$, $R^{24}$ and $R^{25}$ independently of one another for each individual occurrence represent a radical selected from the group consisting of $(C_1$-$C_6)$-alkyl, $(C_3$-$C_7)$-cycloalkyl, and phenyl, where $(C_3$-$C_7)$-cycloalkyl, and phenyl for their part may in each case be substituted up to three times by identical or different substituents selected from the group consisting of halogen, cyano, $(C_1$-$C_4)$-alkyl, trifluoromethyl, hydroxyl, $(C_1$-$C_4)$-alkoxy, trifluoromethoxy, oxo, amino, mono-$(C_1$-$C_4)$-alkylamino, di-$(C_1$-$C_4)$-alkylamino, hydroxycarbonyl and $(C_1$-$C_4)$-alkoxycarbonyl and $(C_1$-$C_6)$-alkyl may be mono- to trisubstituted by identical or different substituents from the group consisting of halogen, cyano, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl, $(C_1$-$C_4)$-alkoxycarbonyl, $(C_3$-$C_7)$-cycloalkyl, and phenyl, and (iv) $R^7$, $R^{10}$, $R^{11}$, $R^{13}$, $R^{15}$, $R^{17}$, $R^{18}$, $R^{22}$ and $R^{26}$ independently of one another for each individual occurrence represent a radical selected from the group consisting of hydrogen and $(C_1$-$C_6)$-alkyl, where $(C_1$-$C_6)$-alkyl may be mono- to trisubstituted by identical or different substituents from the group consisting of halogen, cyano, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl and $(C_1$-$C_4)$-alkoxycarbonyl, m and n independently of one another represent the number 0, 1, 2 or 3, where if $R^1$ or $R^2$ are present more than once, their meanings may in each case be identical or different, and $R^3$ represents hydrogen, $(C_1$-$C_6)$-alkyl or $(C_3$-$C_7)$-cycloalkyl, or a salt thereof.

2. The compound of claim 1 in which

A represents CH, $R^1$ represents a substituent selected from the group consisting of $(C_3$-$C_6)$-cycloalkyl, phenyl, —OC(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2$—$R^{19}$ and —$NR^{25}R^{26}$ in which (i) $(C_3$-$C_6)$-cycloalkyl, and phenyl for their part may in each case be mono- to trisubstituted by identical or different radicals selected from the group consisting of $(C_1$-$C_6)$-alkyl, halogen, cyano, oxo, hydroxyl, amino, hydroxycarbonyl, aminocarbonyl, —C(=O)—$NR^6R^7$, —O—C(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2$—$R^{19}$, —$OR^{23}$ and —$NR^{25}R^{26}$, where the last-mentioned alkyl radical for its part may be substituted up to three times by identical or different substituents from the group consisting of halogen, cyano, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl, $(C_1$-$C_4)$-alkoxycarbonyl, $(C_3$-$C_6)$-cycloalkyl, and phenyl, (ii) $R^6$, $R^9$, $R^{12}$, $R^{14}$, $R^{16}$, $R^{19}$, $R^{23}$ and $R^{25}$ independently of one another for each individual occurrence represent a radical selected from the group consisting of $(C_1$-$C_6)$-alkyl and $(C_3$-$C_6)$-cycloalkyl, where $(C_3$-$C_6)$-cycloalkyl may be substituted up to three times by identical or different substituents selected from the group consisting of halogen, cyano, $(C_1$-$C_4)$-alkyl, trifluoromethyl, hydroxyl, $(C_1$-$C_4)$-alkoxy, trifluoromethoxy, oxo, amino, mono-$(C_1$-$C_4)$-alkylamino, di-$(C_1$-$C_4)$-alkylamino, hydroxycarbonyl and $(C_1$-$C_4)$-alkoxycarbonyl and $(C_1$-$C_6)$-alkyl may be mono- to trisubstituted by identical or different substituents from the group consisting of halogen, cyano, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl, $(C_1$-$C_4)$-alkoxycarbonyl and $(C_3$-$C_6)$-cycloalkyl, and (iii) $R^7$, $R^{10}$, $R^{11}$, $R^{13}$, $R^{15}$, $R^{17}$, $R^{18}$ and $R^{26}$ independently of one another for each individual occurrence represent a radical selected from the group consisting of hydrogen and $(C_1$-$C_6)$-alkyl, where $(C_1$-$C_6)$-alkyl may be mono- to trisubstituted by identical or different substituents from the group consisting of halogen, cyano, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl and $(C_1$-$C_4)$-alkoxycarbonyl, $R^2$ represents a substituent selected from the group consisting of —O—C(=O)—$NR^{9A}R^{10A}$, —$NR^{11A}$—C(=O)—$R^{12A}$, —$NR^{13A}$—C(=O)—$OR^{14A}$, —$NR^{15A}$—C(=O)—$NR^{16A}R^{17A}$, $NR^{18A}$—$SO_2$—$R^{19A}$ and —$NR^{25A}R^{26A}$ in which (i) $R^{9A}$, $R^{12A}$, $R^{14A}$, $R^{16A}$, $R^{19A}$ and $R^{25A}$ independently of one another represent $(C_1$-$C_6)$-alkyl represent $(C_1$-$C_6)$-alkyl which may in each case be substituted by halogen, cyano, trifluoromethyl, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl or $(C_1$-$C_4)$-alkoxycarbonyl, (ii) $R^{10A}$, $R^{11A}$, $R^{13A}$, $R^{15A}$, $R^{17A}$, $R^{18A}$ and $R^{26A}$ independently of one another represent hydrogen or $(C_1$-$C_6)$-alkyl which may in each case be substituted by halogen, cyano, trifluoromethyl, hydroxyl, trifluoromethoxy, $(C_1$-$C_4)$-alkoxy, amino, mono-$(C_1$-$C_4)$-alkylamino, di-$(C_1$-$C_4)$-alkylamino, hydroxycarbonyl or $(C_1$-$C_4)$-alkoxycarbonyl, m represents the number 1, n represents the number 0 or 1 and $R^3$ represents hydrogen, or a salt thereof.

3. The compound of claim 1 in which

A represents CH, $R^1$ represents a substituent selected from the group consisting of ($C_3$-$C_6$)-cycloalkyl, phenyl, —O—C(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2$—$R^{19}$ and —$NR^{25}R^{26}$ in which (i) ($C_3$-$C_6$)-cycloalkyl, and phenyl for their part may in each case be mono- to trisubstituted by identical or different radicals selected from the group consisting of ($C_1$-$C_6$)-alkyl, halogen, cyano, oxo, hydroxyl, amino, hydroxycarbonyl, aminocarbonyl, —C(=O)—$NR^6R^7$, —O—C(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2$—$R^{19}$, —$OR^{23}$ and —$NR^{25}R^{26}$, where the last-mentioned alkyl radical for its part may be substituted up to three times by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, ($C_3$-$C_6$)-cycloalkyl, and phenyl, (ii) $R^6$, $R^9$, $R^{12}$, $R^{14}$, $R^{16}$, $R^{19}$, $R^{23}$ and $R^{25}$ independently of one another for each individual occurrence represent a radical selected from the group consisting of ($C_1$-$C_6$)-alkyl, and ($C_3$-$C_6$)-cycloalkyl, where ($C_3$-$C_6$)-cycloalkyl may be substituted up to three times by identical or different substituents selected from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl and ($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl and ($C_3$-$C_6$)-cycloalkyl, and (iii) $R^7$, $R^{10}$, $R^{11}$, $R^{13}$, $R^{15}$, $R^{17}$, $R^{18}$ and $R^{26}$ independently of one another for each individual occurrence represent a radical selected from the group consisting of hydrogen and ($C_1$-$C_6$)-alkyl, where ($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and ($C_1$-$C_4$)-alkoxycarbonyl, and $R^2$ represents a substituent selected from the group consisting of halogen, cyano, nitro, ($C_1$-$C_6$)-alkyl, trifluoromethyl, hydroxyl, ($C_1$-$C_6$)-alkoxy, trifluoromethoxy, amino, hydroxycarbonyl and —C(=O)—NH—$R^{7A}$ in which ($C_1$-$C_6$)-alkyl and ($C_1$-$C_6$)-alkoxy for their part may be substituted by hydroxyl and $R^{7A}$ represents hydrogen or ($C_1$-$C_4$)-alkyl, m represents the number 1, n represents the number 0 or 1 and $R^3$ represents hydrogen, or a salt thereof.

4. The compound of claim 1 in which

A represents CH, $R^1$ represents a substituent selected from the group consisting of ($C_1$-$C_6$)-alkyl, trifluoromethyl, halogen, cyano, nitro, hydroxyl, ($C_1$-$C_6$)-alkoxy, amino, hydroxycarbonyl, ($C_1$-$C_6$)-alkoxycarbonyl and —C(=O)—NH—$R^7$ in which ($C_1$-$C_6$)-alkyl for its part may be substituted by hydroxyl, ($C_1$-$C_4$)-alkoxy, amino, mono-($C_1$-$C_4$)-alkylamino, di-($C_1$-$C_4$)-alkylamino or a group of the formula —NH—C(=O)—$R^{12}$, —NH—C(=O)—NH—$R^{16}$ or —NH—$SO_2$—$R^{19}$ in which $R^{12}$, $R^{16}$ and $R^{19}$ each represent ($C_1$-$C_6$)-alkyl which may be substituted by hydroxyl or ($C_1$-$C_4$)-alkoxy, and $R^7$ represents hydrogen or ($C_1$-$C_6$)-alkyl which may be substituted by hydroxyl or ($C_1$-$C_4$)-alkoxy, $R^2$ represents a substituent selected from the group consisting of —O—C(=O)—$NR^{9A}R^{10A}$, —$NR^{11A}$—C(=O)—$R^{12A}$, —$NR^{13A}$—C(=O)—$OR^{14A}$, —$NR^{15A}$—C(=O)—$NR^{16A}R^{17A}$, $NR^{18A}$—$SO_2$—$R^{19A}$ and —$NR^{25A}R^{26A}$ in which (i) $R^{9A}$, $R^{12A}$, $R^{14A}$, $R^{16A}$, $R^{19A}$ and $R^{25A}$ independently of one another represent ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, and (ii) $R^{10A}$, $R^{11A}$, $R^{13A}$, $R^{15A}$, $R^{17A}$, $R^{18A}$ and $R^{26A}$ independently of one another represent hydrogen or ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, m represents the number 1, n represents the number 0 or 1 and $R^3$ represents hydrogen, or a salt thereof.

5. The compound of claim 1 in which

A represents CH, $R^1$ represents ($C_1$-$C_6$)-alkyl which (i) is mono- or disubstituted by identical or different radicals from the group consisting of halogen, cyano, trifluoromethyl, ($C_3$-$C_6$)-cyclo-alkyl, hydroxycarbonyl, aminocarbonyl, —C(=O)—$NR^6R^7$, —O—C(=O)—$NR^9R^{10}$, —$NR^{11}$—C(=O)—$R^{12}$, —$NR^{13}$—C(=O)—$OR^{14}$, —$NR^{15}$—C(=O)—$NR^{16}R^{17}$, —$NR^{18}$—$SO_2$—$R^{19}$, —$OR^{23}$ and —$NR^{25}R^{26}$ and additionally may be substituted by hydroxyl, ($C_1$-$C_4$)-alkoxy, amino, mono-($C_1$-$C_4$)-alkylamino, di-($C_1$-$C_4$)-alkylamino or ($C_1$-$C_4$)-acylamino, or (ii) is disubstituted by identical or different radicals from the group consisting of hydroxyl, ($C_1$-$C_4$)-alkoxy, amino, mono-($C_1$-$C_4$)-alkylamino, di-($C_1$-$C_4$)-alkylamino and ($C_1$-$C_4$)-acylamino in which (a) the abovementioned cycloalkyl radical may be substituted up to three times by identical or different substituents selected from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl, (b) $R^7$, $R^{10}$, $R^{11}$, $R^{13}$, $R^{15}$, $R^{17}$, $R^{18}$ and $R^{26}$ independently of one another for each individual occurrence represent a radical selected from the group consisting of hydrogen and $(C_1-C_6)$-alkyl, where $(C_1-C_6)$-alkyl may be mono- to trisubstituted by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl and $(C_1-C_4)$-alkoxycarbonyl, (c) $R^6$, $R^9$ and $R^{14}$ independently of one another for each individual occurrence represent a radical selected from the group consisting of $(C_1-C_6)$-alkyl, and $(C_3-C_6)$-cycloalkyl, where $(C_3-C_6)$-cycloalkyl may be substituted up to three times by identical or different substituents selected from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl and $(C_1-C_6)$-alkyl may be mono- to trisubstituted by identical or different substituents from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, and $(C_3-C_6)$-cycloalkyl, (d) $R^{12}$, $R^{16}$ and $R^{19}$ independently of one another for each individual occurrence represent a radical selected from the group consisting of $(C_1-C_6)$-alkyl, and $(C_3-C_6)$-cycloalkyl, where $(C_3-C_6)$-cycloalkyl may be substituted up to three times by identical or different substituents selected from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl and $(C_1-C_6)$-alkyl is mono- to trisubstituted by identical or different radicals selected from the group consisting of halogen, cyano, amino, mono-$(C_1-C_4)$-alkylamino, di-$(C_1-C_4)$-alkylamino, hydroxycarbonyl, $(C_1-C_4)$-alkoxycarbonyl, and $(C_3-C_6)$-cyclo-alkyl, (e) $R^{23}$ and $R^{25}$ independently of one another for each individual occurrence represent a radical selected from the group consisting of $(C_1-C_6)$-alkyl, and $(C_3-C_6)$-cycloalkyl, where $(C_3-C_6)$-cycloalkyl may be substituted up to three times by identical or different substituents selected from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl and $(C_1-C_6)$-alkyl is mono- to trisubstituted by identical or different radicals selected from the group consisting of halogen, cyano, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, and $(C_3-C_6)$-cycloalkyl, $R^2$ represents a substituent selected from the group consisting of halogen, cyano, $(C_1-C_6)$-alkyl, trifluoromethyl, hydroxyl, trifluoromethoxy, amino, hydroxycarbonyl, aminocarbonyl, —C(=O)—$NR^{6A}R^{7A}$, —O—C(=O)—$NR^{9A}R^{10A}$, —$NR^{11A}$—C(=O)—$R^{12A}$, —$NR^{13A}$—C(=O)—$OR^{14A}$, —$NR^{15A}$—C(=O)—$NR^{16A}R^{17A}$, —$NR^{18A}$—$SO_2$—$R^{19A}$—$OR^{23A}$ and —$NR^{25A}R^{26A}$ in which (i) $(C_1-C_6)$-alkyl may be substituted by halogen, cyano, trifluoromethyl, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl or $(C_1-C_4)$-alkoxycarbonyl, (ii) $R^{6A}$, $R^{9A}$, $R^{12A}$, $R^{14A}$, $R^{16A}$, $R^{19A}$, $R^{23A}$ and $R^{25A}$ independently of one another represent $(C_1-C_6)$-alkyl which may in each case be substituted by halogen, cyano, trifluoromethyl, hydroxyl, trifluoromethoxy, $(C_1-C_4)$-alkoxy, amino, mono-$(C_1-C_4)$-alkyl amino, di-$(C_1-C_4)$-alkyl amino, hydroxycarbonyl or $(C_1-C_4)$-alkoxycarbonyl, (III) $R^{7A}$, $R^{10A}$, $R^{11A}$, $R^{13A}$, $R^{15A}$, $R^{17A}$, $R^{18A}$ and $R^{26A}$ independently of one another represent hydrogen or $(C_1-C_6)$-alkyl which may in each case be substituted by halogen, cyano, trifluoromethyl, hydroxyl, trifluoromethoxy, $(C_1-C_4)$-alkoxy, amino, mono-$(C_1-C_4)$-alkylamino, di-$(C_1-C_4)$-alkylamino, hydroxycarbonyl or $(C_1-C_4)$-alkoxycarbonyl, m represents the number 1,
n represents the number 0 or 1
and
$R^3$ represents hydrogen,
or a salt thereof.

6. The compound of claim 1 in which

A represents CH, $R^1$ represents $(C_1-C_6)$-alkoxy which is mono- or disubstituted by identical or different radicals selected from the group consisting of halogen, cyano, trifluoromethyl, $(C_3-C_6)$-cycloalkyl, hydroxyl, amino, hydroxycarbonyl, aminocarbonyl, —C(=O)—$NR^6R^7$, —O—C(=O)—$NR^9R^{10}$, $NR^{11}$—C(=O)—$R^{12}$, —$NR^{13}$—C(=O)—$OR^{14}$, —$NR^{15}$—C(=O)—$NR^{16}R^{17}$, $NR^{18}$—$SO_2$—$R^{19}$, —$OR^{23}$ and —$NR^{25}R^{26}$ in which (i) $(C_3-C_6)$-cycloalkyl may be mono- to trisubstituted by identical or different substituents from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-C_4)$-alkylamino, di-$(C_1-C_4)$-alkylamino, hydroxycarbonyl and $(C_1-C_4)$-alkoxycarbonyl, (ii) $R^6$, $R^9$, $R^{12}$, $R^{14}$, $R^{16}$, $R^{19}$, $R^{23}$ and $R^{25}$ independently of one another for each individual occurrence represent a radical selected from the group consisting of $(C_1-C_6)$-alkyl, and $(C_3-C_6)$-cycloalkyl, where $(C_3-C_6)$-cycloalkyl may be substituted up to three times by identical or different substituents selected from the group consisting of halogen, cyano, $(C_1-C_4)$-alkyl, trifluoromethyl, hydroxyl, $(C_1-C_4)$-alkoxy, trifluoromethoxy, oxo, amino, mono-$(C_1-$ $C_4$)-alkylamino, di-($C_1$-$C_4$)-alkylamino, hydroxycarbonyl and ($C_1$-$C_4$)-alkoxycarbonyl and ($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, and ($C_3$-$C_6$)-cycloalkyl, (iii) $R^7$, $R^{10}$, $R^{11}$, $R^{13}$, $R^{15}$, $R^{17}$, $R^{18}$ and $R^{26}$ independently of one another for each individual occurrence represent a radical selected from the group consisting of hydrogen and ($C_1$-$C_6$)-alkyl, where ($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and ($C_1$-$C_4$)-alkoxycarbonyl, $R^2$ represents a substituent selected from the group consisting of halogen, cyano, ($C_1$-$C_6$)-alkyl, trifluoromethyl, hydroxyl, trifluoromethoxy, amino, hydroxycarbonyl, aminocarbonyl, —C(=O)—$NR^{6A}R^{7A}$, —O—C(=O)—$NR^{9A}R^{10A}$, $NR^{11A}$—C(=O)—$R^{12A}$, —$NR^{13A}$—C(=O)—$OR^{14A}$, —$NR^{15A}$—C(=O)—$NR^{16A}R^{17A}$, —$NR^{18A}$—$SO_2$—$R^{19A}$, —$OR^{23A}$ and —$NR^{25A}R^{26A}$ in which (i) ($C_1$-$C_6$)-alkyl may be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, (ii) $R^{6A}$, $R^{9A}$, $R^{12A}$, $R^{14A}$, $R^{16A}$, $R^{19A}$, $R^{23A}$ and $R^{25A}$ independently of one another represent ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkyl amino, di-($C_1$-$C_4$)-alkyl amino, hydroxycarbonyl or ($C_1$-$C_4$)-alkoxycarbonyl, (iii) $R^{7A}$, $R^{10A}$, $R^{11A}$, $R^{13A}$, $R^{15A}$, $R^{17A}$, $R^{18A}$ and $R^{26A}$ independently of one another represent hydrogen or ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, m represents the number 1,
n represents the number 0 or 1
and
$R^3$ represents hydrogen,
or a salt thereof.

7. The compound of claim 1 in which
A represents CH,
$R^1$ represents the group —C(=O)—$NR^6R^7$
in which (i)
$R^6$ represents ($C_3$-$C_6$)-cycloalkyl which may be mono- to trisubstituted by identical or different substituents from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl,
or
represents ($C_1$-$C_6$)-alkyl which
(a) is mono- or disubstituted by identical or different radicals selected from the group consisting of halogen, cyano, trifluoromethyl, amino, mono-($C_1$-$C_4$)-alkylamino, di-($C_1$-$C_4$)-alkylamino, hydroxycarbonyl, ($C_1$-$C_4$)-alkoxycarbonyl, and ($C_3$-$C_6$)-cycloalkyl and may additionally be substituted by hydroxyl or ($C_1$-$C_4$)-alkoxy,
or
(b) is disubstituted by hydroxyl and/or ($C_1$-$C_4$)-alkoxy,
and
$R^7$ represents hydrogen,
or in which (ii)
$R^6$ represents ($C_1$-$C_6$)-alkyl or ($C_3$-$C_6$)-cycloalkyl,
where
($C_3$-$C_6$)-cycloalkyl may be substituted up to three times by identical or different substituents selected from the group consisting of halogen, cyano, ($C_1$-$C_4$)-alkyl, trifluoromethyl, hydroxyl, ($C_1$-$C_4$)-alkoxy, trifluoromethoxy, oxo, amino, mono-($C_1$-$C_4$)-alkylamino, di-($C_1$-$C_4$)-alkylamino, hydroxycarbonyl and ($C_1$-$C_4$)-alkoxycarbonyl
and
($C_1$-$C_6$)-alkyl may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, and ($C_3$-$C_6$)-cycloalkyl and
and
$R^7$ represents ($C_1$-$C_6$)-alkyl which may be mono- to trisubstituted by identical or different substituents from the group consisting of halogen, cyano, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl and ($C_1$-$C_4$)-alkoxycarbonyl,
$R^2$ represents a substituent selected from the group consisting of halogen, cyano, ($C_1$-$C_6$)-alkyl, trifluoromethyl, hydroxyl, trifluoromethoxy, amino, hydroxycarbonyl, aminocarbonyl, —C(=O)—$NR^{6A}R^{7A}$, —O—C(=O)—$NR^{9A}R^{10A}$, $NR^{11A}$—C(=O)—$R^{12A}$, $NR^{13A}$—C(=O)—$OR^{14A}$, —$NR^{15A}$—C(=O)—$NR^{16A}R^{17A}$, —$NR^{18A}$—$SO_2$—$R^{19A}$, —$OR^{23A}$ and —$NR^{25A}R^{26A}$ in which (i) ($C_1$-$C_6$)-alkyl may be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, (ii) $R^{6A}$, $R^{9A}$, $R^{12A}$, $R^{14A}$, $R^{16A}$, $R^{19A}$, $R^{23A}$ and $R^{25A}$ independently of one another represent ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, (iii) $R^{7A}$, $R^{10A}$, $R^{11A}$, $R^{13A}$, $R^{15A}$, $R^{17A}$, $R^{18A}$ and $R^{26A}$ independently of one another represent hydrogen or ($C_1$-$C_6$)-alkyl which may in each case be substituted by halogen, cyano, trifluoromethyl, hydroxyl, trifluoromethoxy, ($C_1$-$C_4$)-alkoxy, amino, mono-($C_1$-$C_4$)-alkylamino, di-($C_1$-$C_4$)-alkylamino, hydroxycarbonyl or ($C_1$-$C_4$)-alkoxycarbonyl, m represents the number 1,
n represents the number 0 or 1
and
$R^3$ represents hydrogen,
and salts thereof.

8. The compound as claimed in claim 1 of the formula (I-A) or (I-B)

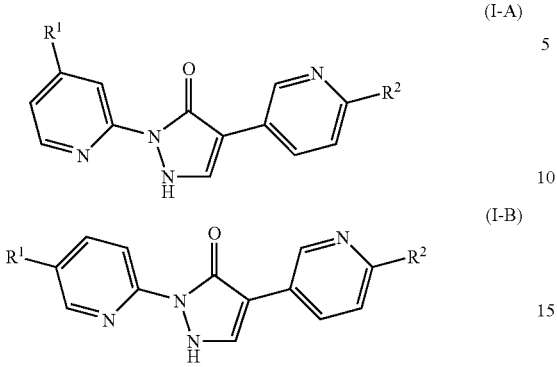

in which
R¹ represents phenyl which may be mono- or disubstituted by identical or different radicals selected from the group consisting of fluorine, chlorine, bromine, cyano, $(C_1-C_4)$-alkyl, hydroxyl, amino, hydroxycarbonyl, —OR²³ and —NR²⁵R²⁶ in which
  $(C_1-C_4)$-alkyl for its part may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino, hydroxycarbonyl, $(C_3-C_6)$-cycloalkyl, and phenyl,
  R²³ and R²⁵ independently of one another for each individual occurrence represent $(C_1-C_4)$-alkyl which may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino, hydroxycarbonyl, and $(C_3-C_6)$-cycloalkyl, and
  R²⁶ for each individual occurrence represents hydrogen or $(C_1-C_4)$-alkyl which may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino and hydroxycarbonyl,
and
R² represents hydrogen, fluorine, chlorine, cyano, $(C_1-C_4)$-alkyl, trifluoromethyl, hydroxymethyl, $(C_1-C_4)$-alkoxy, trifluoromethoxy, amino or hydroxycarbonyl,
or a salt thereof.

9. The compound as claimed in claim 1 of the formula (I-A) or (I-B)

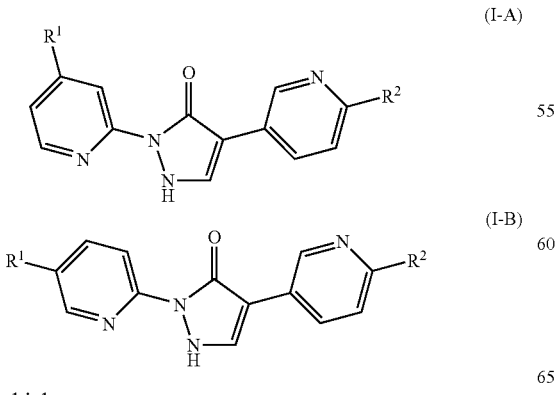

in which
R¹ represents $(C_1-C_6)$-alkyl which (i) is mono- or disubstituted by identical or different radicals selected from the group consisting of fluorine, chlorine, cyano, trifluoromethyl, $(C_3-C_6)$-cycloalkyl, hydroxycarbonyl, —C(=O)—NR⁶R⁷, —O—C(=O)—NR⁹R¹⁰, NR¹¹—C(=O)—R¹², NR¹³—C(=O)—OR¹⁴, —NR¹⁵—C(=O)—NR¹⁶R¹⁷, —NR¹⁸—SO₂—R¹⁹, —OR²³ and —NR²⁵R²⁶
and may additionally be substituted by hydroxyl, $(C_1-C_4)$-alkoxy, amino, mono-$(C_1-C_4)$-alkylamino, di-$(C_1-C_4)$-alkylamino or $(C_1-C_4)$-acylamino,
or
(ii) is disubstituted by identical or different radicals selected from the group consisting of hydroxyl, $(C_1-C_4)$-alkoxy, amino, mono-$(C_1-C_4)$-alkylamino, di-$(C_1-C_4)$-alkylamino and $(C_1-C_4)$-acylamino in which
  (a) the above-mentioned cycloalkyl radical may be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl,
  (b) R⁷, R¹⁰, R¹¹, R¹³, R¹⁵, R¹⁷, R¹⁸ and R²⁶ independently of one another for each individual occurrence represent a radical selected from the group consisting of hydrogen and $(C_1-C_4)$-alkyl, where $(C_1-C_4)$-alkyl may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino and hydroxycarbonyl,
  (c) R⁶, R⁹ and R¹⁴ independently of one another for each individual occurrence represent a radical selected from the group consisting of $(C_1-C_4)$-alkyl, and $(C_3-C_6)$-cycloalkyl, where
    $(C_3-C_6)$-cycloalkyl may in each case be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl
    and
    $(C_1-C_4)$-alkyl may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino, hydroxycarbonyl, and $(C_3-C_6)$-cycloalkyl,
  (d) R¹², R¹⁶ and R¹⁹ independently of one another for each individual occurrence represent a radical selected from the group consisting of $(C_1-C_4)$-alkyl and $(C_3-C_6)$-cycloalkyl, where
    $(C_3-C_6)$-cycloalkyl may be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl
    and
    $(C_1-C_4)$-alkyl is mono- to trisubstituted by identical or different radicals selected from the group consisting of fluorine, chlorine, cyano, amino, mono-$(C_1-C_4)$-alkylamino, di-$(C_1-C_4)$-alkylamino, hydroxycarbonyl, $(C_1-C_4)$-alkoxycarbonyl, and $(C_3-C_6)$-cyclo-alkyl, (e) $R^{23}$ and $R^{25}$ independently of one another for each individual occurrence represent a radical selected from the group consisting of $(C_1-C_4)$-alkyl, and $(C_3-C_6)$-cycloalkyl, where $(C_3-C_6)$-cycloalkyl may be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl and $(C_1-C_4)$-alkyl is mono- to trisubstituted by identical or different radicals selected from the group consisting of fluorine, chlorine, cyano, hydroxyl, $(C_1-C_4)$-alkoxy, amino, mono-$(C_1-C_4)$-alkyl-amino, di-$(C_1-C_4)$-alkylamino, hydroxycarbonyl, and $(C_3-C_6)$-cycloalkyl, and $R^2$ represents hydrogen, fluorine, chlorine, cyano, trifluoromethyl, hydroxymethyl, $(C_1-C_4)$-alkoxy, trifluoromethoxy, amino or hydroxycarbonyl, or a salt thereof.

10. The compound as claimed in claim 1 of the formula (I-A) or (I-B)

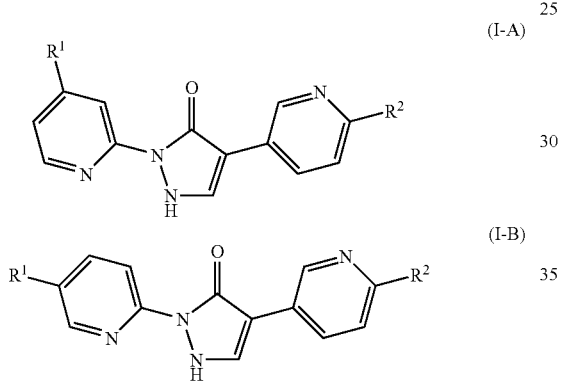

in which $R^1$ represents $(C_1-C_6)$-alkoxy which is mono- or disubstituted by identical or different radicals selected from the group consisting of fluorine, chlorine, cyano, trifluoromethyl, $(C_3-C_6)$-cycloalkyl, hydroxyl, amino, hydroxycarbonyl, —C(=O)—NR$^6$R$^7$, —O—C(=O)—NR$^9$R$^{10}$, NR$^{11}$C—C(=O)R$^{12}$, NR$^{13}$—C(=O)—OR$^{14}$, —NR$^{15}$—C(=O)—NR$^{16}$R$^{17}$, —NR$^{18}$—SO$_2$—R$^{19}$, —OR$^{23}$ and —NR$^{25}$R$^{26}$ in which (i) $(C_3-C_6)$-cycloalkyl may be mono- to trisubstituted by identical or different substituents from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl, (ii) $R^6$, $R^9$, $R^{12}$, $R^{14}$, $R^{16}$, $R^{19}$, $R^{23}$ and $R^{25}$ independently of one another for each individual occurrence represent a radical selected from the group consisting of $(C_1-C_4)$-alkyl, and $(C_3-C_6)$-cycloalkyl, where $(C_3-C_6)$-cycloalkyl may be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl and $(C_1-C_4)$-alkyl may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino, hydroxycarbonyl, and $(C_3-C_6)$-cycloalkyl, (iii) $R^7$, $R^{10}$, $R^{11}$, $R^{13}$, $R^{15}$, $R^{17}$, $R^{18}$ and $R^{26}$ independently of one another for each individual occurrence represent a radical selected from the group consisting of hydrogen and $(C_1-C_4)$-alkyl, where $(C_1-C_4)$-alkyl may be mono- to trisubstituted by identical or different substituents from the group consisting of fluorine, chlorine, cyano, hydroxyl, $(C_1-C_4)$-alkoxy, amino, mono-$(C_1-C_4)$-alkylamino, di-$(C_1-C_4)$-alkylamino and hydroxycarbonyl, and $R^2$ represents hydrogen, fluorine, chlorine, cyano, $(C_1-C_4)$-alkyl, trifluoromethyl, hydroxymethyl, $(C_1-C_4)$-alkoxy, trifluoromethoxy, amino or hydroxycarbonyl, or a salt thereof.

11. The compound as claimed in claim 1 of the formula (I-A) or (I-B)

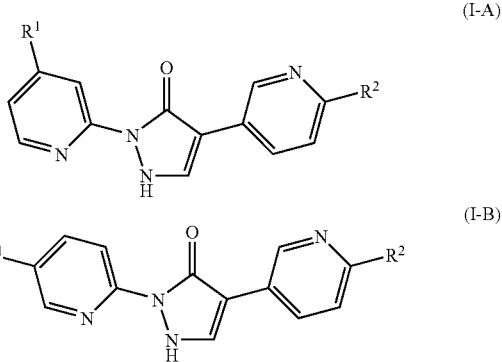

in which $R^1$ represents the group —C(=O)—NR$^6$R$^7$ in which (i)

$R^6$ represents $(C_3-C_6)$-cycloalkyl which may be mono- to trisubstituted by identical or different substituents from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl, or represents $(C_1-C_6)$-alkyl which (a) is mono- or disubstituted by identical or different radicals selected from the group consisting of fluorine, chlorine, cyano, trifluoromethyl, amino, mono-$(C_1-C_4)$-alkylamino, di-$(C_1-C_4)$-alkylamino, hydroxycarbonyl, and $(C_3-C_6)$-cycloalkyl and may additionally be substituted by hydroxyl or $(C_1-C_4)$-alkoxy, or (b) is disubstituted by hydroxyl and/or $(C_1-C_4)$-alkoxy, and $R^7$ represents hydrogen, or in which (ii)

$R^6$ represents $(C_1-C_6)$-alkyl, or $(C_3-C_6)$-cycloalkyl, where $(C_3-C_6)$-cycloalkyl may be substituted up to three times by identical or different substituents selected from the group consisting of fluorine, chlorine, cyano, $(C_1-C_4)$-alkyl, trifluoromethyl, hydroxyl, $(C_1-C_4)$-alkoxy, oxo, amino, mono-$(C_1-C_4)$-alkylamino, di-$(C_1-C_4)$-alkylamino and hydroxycarbonyl and
(C$_1$-C$_6$)-alkyl may be mono- to trisubstituted by identical or different substituents from the group consisting of fluorine, chlorine, cyano, hydroxyl, (C$_1$-C$_4$)-alkoxy, amino, mono-(C$_1$-C$_4$)-alkylamino, di-(C$_1$-C$_4$)-alkylamino, hydroxycarbonyl, and (C$_3$-C$_6$)-cycloalkyl,
and
R$^7$ represents (C$_1$-C$_4$)-alkyl which may be mono- to trisubstituted by identical or different substituents from the group consisting of fluorine, chlorine, cyano, hydroxyl, (C$_1$-C$_4$)-alkoxy, amino, mono-(C$_1$-C$_4$)-alkylamino, di-(C$_1$-C$_4$)-alkylamino and hydroxycarbonyl,
and
R$^2$ represents hydrogen, fluorine, chlorine, cyano, (C$_1$-C$_4$)-alkyl, trifluoromethyl, hydroxymethyl, (C$_1$-C$_4$)-alkoxy, trifluoromethoxy, amino or hydroxycarbonyl,
or a salt thereof.

12. A method of making a compound of the formula (I) as defined in claim 1, comprising:
reacting a compound of the formula (II)

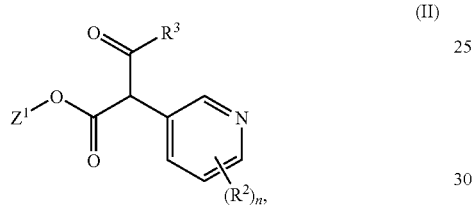

(II)

in which R$^2$, R$^3$ and n have the meanings given in claim 1
and
Z$^1$ represents methyl or ethyl,
in an inert solvent, optionally, in the presence of an acid, with a compound of the formula (III)

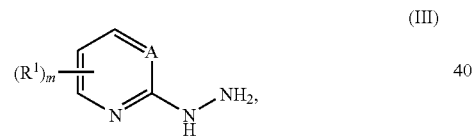

(III)

in which A, R$^1$ and m have the meanings given in claim 1, to give compounds of the formula (IV)

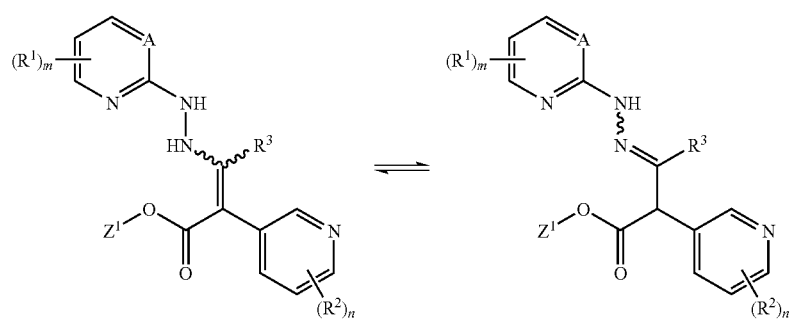

in which Z$^1$, A, R$^1$, R$^2$, R$^3$, m and n have the meanings given in claim 1, which, already under these reaction conditions or in a subsequent reaction step under the influence of a base, cyclize to give at least one compound of formula (I),
and optionally converting the compound of formula (I) with an appropriate (i) solvent and/or (ii) base or acid, into a salt thereof.

13. A method of making a compound of the formula (I) as defined in claim 1 in which R$^3$ represents hydrogen, comprising
condensing a compound of the formula (V)

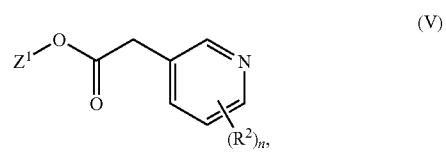

(V)

in which R$^2$ and n have the meanings given in claim 1
and
Z$^1$ represents methyl or ethyl,
with a compound of the formula (VI)

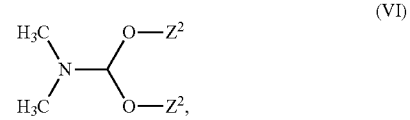

(VI)

in which
Z$^2$ represents methyl or ethyl,
to give a compounds of the formula (VII)

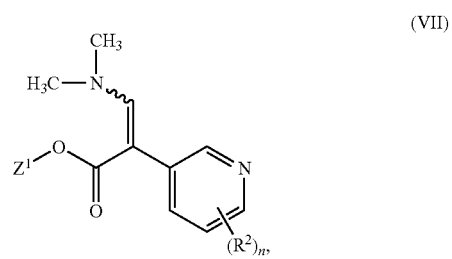

(VII)

in which Z$^1$, R$^2$ and n have the meanings given above,
and reacting the compound of formula (VII) in the presence of an acid with a compound of the formula (III)

(IV)

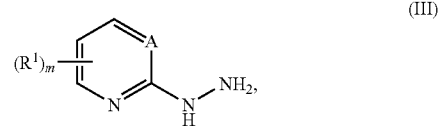

(III)

in which A, $R^1$ and m have the meanings given in claim 1, to give compounds of the formula (IV-A)

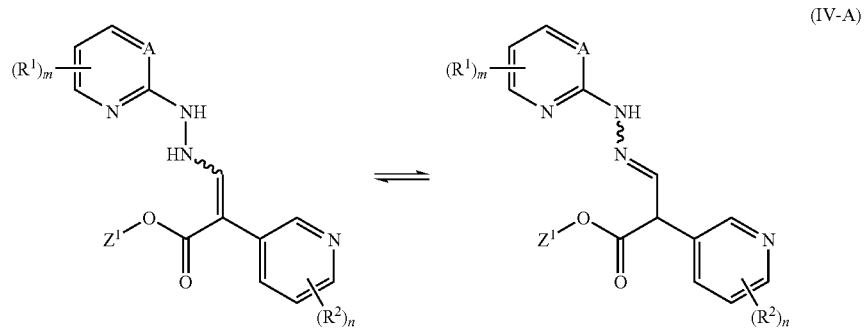

(IV-A)

in which $Z^1$, A, $R^1$, $R^2$, m and n have the meanings given above, which, already under these reaction conditions or in a subsequent reaction step under the influence of a base, cyclize to give the compounds of the formula (I) in which $R^3$ represents hydrogen.

14. A pharmaceutical composition comprising a compound of claim 1 in combination with an inert, non-toxic, pharmaceutically suitable auxiliary.

\* \* \* \* \*